United States Patent
Behrens et al.

(10) Patent No.: US 9,546,217 B2
(45) Date of Patent: Jan. 17, 2017

(54) RECOMBINANT ANTI-MUC1 ANTIBODIES

(75) Inventors: Christian Behrens, Palaiseau (DE); Holger Thie, Braunschweig (DE); Michael Hust, Hannover (DE); Lars Toleikis, Kleinniedesheim (DE); Thomas Schirrmann, Berlin (DE); Stefan Dübel, Braunschweig (DE); Christophe De Romeuf, Lambersart (FR)

(73) Assignee: MAB FACTORY GMBH, Braunschweig (DE)

( * ) Notice: Subject to any disclaimer, the term of this patent is extended or adjusted under 35 U.S.C. 154(b) by 1553 days.

(21) Appl. No.: 13/054,612

(22) PCT Filed: Jul. 17, 2009

(86) PCT No.: PCT/EP2009/005218
§ 371 (c)(1),
(2), (4) Date: Sep. 8, 2011

(87) PCT Pub. No.: WO2010/006810
PCT Pub. Date: Jan. 21, 2010

(65) Prior Publication Data
US 2011/0318757 A1 Dec. 29, 2011

(30) Foreign Application Priority Data
Jul. 18, 2008 (EP) .................... 08160727

(51) Int. Cl.
*C07K 16/00* (2006.01)
*C07K 16/30* (2006.01)

(52) U.S. Cl.
CPC ....... *C07K 16/3092* (2013.01); *C07K 2317/21* (2013.01); *C07K 2317/34* (2013.01); *C07K 2317/565* (2013.01); *C07K 2317/622* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| EP | 0534742 A1 | 3/1993 |
| WO | 01/75110 A2 | 10/2001 |
| WO | 02/44217 A2 | 6/2002 |

OTHER PUBLICATIONS

International Search Report for PCT/EP2009/005218 dated Nov. 20, 2009 (Form PCT/ISA/210).

*Primary Examiner* — Brad Duffy
(74) *Attorney, Agent, or Firm* — Buchanan Ingersoll & Rooney PC

(57) ABSTRACT

Antibodies having a high specificity and high affinity towards the human gene product MUC1, which in specific variants is associated with neoplastic cells, i.e. tumor tissue, to the use of the antibodies for medical purposes, i.e. for tumor treatment, and for analytical purposes, e.g. for tumor diagnosis. Compositions comprising the antibodies, e.g. for use in the analytical processes and analysis, to pharmaceutical compositions comprising the antibodies, and to use of the antibodies in the manufacture of pharmaceutical compositions for tumor treatment or for diagnostic purposes.

15 Claims, 43 Drawing Sheets

Fig. 1A

| VH | FR1 | CDR1 | FR2 | CDR2 | FR3 | CDR3 | FR4 |
|---|---|---|---|---|---|---|---|
| HT186-D11 | (Seq.-ID No. 37) QMQLVQSEAELKKP GASVKVSCKAS | (Seq.-ID No. 1) GYSFT GHY | (Seq.-ID No. 43) MHWVRQAP GQGLEWMG W | (Seq.-ID No. 7) IDPVTG GT | (Seq.-ID No. 49) KYAQNFQGWVTMTRDTS IRTAYLELSRLRSDDTAM YYC | (Seq.-ID No. 13) AREVTGD RGQFDK | (Seq.-ID No. 55) WGQGTL VTVAS |
| HT200-3A-C1 | (Seq.-ID No. 38) QMQLVQSGAEVKK PGASVKVSCKAS | (Seq.-ID No. 2) GYTFT GHY | (Seq.-ID No. 44) MHWVRQAP GQGLEWMG W | (Seq.-ID No. 8) IDPVTG GT | (Seq.-ID No. 50) KYAQNFQGWVTMTRDTS IRTAYMELSRLRSDDTAM YYC | (Seq.-ID No. 14) AREVTGD RGQFDK | (Seq.-ID No. 56) WGQGTL VTVAS |
| HT220-M-D1 | (Seq.-ID No. 39) QMLLVQSGAEAKK PGASVKVSCKAS | (Seq.-ID No. 3) GYTFT GHY | (Seq.-ID No. 45) MHWVRQAP GQGLEWMG W | (Seq.-ID No. 9) IDPVTG GT | (Seq.-ID No. 51) KYAQNFQGWVTMTRDTS IRTAYMELSRLRPDDTAM YYC | (Seq.-ID No. 15) AREVTGD RGQFDK | (Seq.-ID No. 57) WGQGTL VTVAS |
| HT220-M-G8 | (Seq.-ID No. 40) QMQLVQSGAEVMK PGASVKVSCKAS | (Seq.-ID No. 4) GYSFT GHY | (Seq.-ID No. 46) MHWVRHAP GQGLEWMG W | (Seq.-ID No. 10) IDPVTGS T | (Seq.-ID No. 52) KYAQNFQGWVTMTRDTS ISTAYMELSRLRSDDTAM YYC | (Seq.-ID No. 16) AREVTGD RGQFDK | (Seq.-ID No. 58) WGQGTL VTVAS |
| HT186-B7 | (Seq.-ID No. 41) QMQLVQSGAEVKK PGASVKVSCKAS | (Seq.-ID No. 5) GYTFT GHY | (Seq.-ID No. 47) MHWVRQAP GQGLEWMG W | (Seq.-ID No. 11) IDPVTG GT | (Seq.-ID No. 53) KYAQNFQGWVTMTRDTS IRTAYMELSRLRSDDTAM YYC | (Seq.-ID No. 17) AREVTGD RGQFDK | (Seq.-ID No. 59) WGQGTL VTVAS |
| HT186-G2 | (Seq.-ID No. 42) RMQLVQSGAEVKK PGASVKLSCKAS | (Seq.-ID No. 6) GYTFA GHY | (Seq.-ID No. 48) MHWVRQAP GRGLEWMG W | (Seq.-ID No. 12) IDPVTG GT | (Seq.-ID No. 54) KYAQNFQGWVTMTRDTS IRTAYMELSRLRSDDTAM YYC | (Seq.-ID No. 18) AREVTGD RGQFDK | (Seq.-ID No. 60) WGQGTL VTVAS |

Fig. 1 A (cont.)

| VL | FR1 | CDR1 | FR2 | CDR2 | FR3 | CDR3 | FR4 |
|---|---|---|---|---|---|---|---|
| HT186-D11 | (Seq.-ID No. 61) QSVLTQPPSVSVAPGK TARITCGGN | (Seq.-ID No. 19) NIGSKS | (Seq.-ID No. 67) VHWYQQKPG QAPALVIY | (Seq.-ID No. 25) YGS | (Seq.-ID No. 73) NRPSGIPERFSGSNSGNTAT LTISRVEAGDEADYYC | (Seq.-ID No. 31) QVWDSSSD WV | (Seq.-ID No. 79) FGGGTKL TVL |
| HT200-3A-C1 | (Seq.-ID No. 62) QSVLTQPPSVSVSMAPG ETARITCGGN | (Seq.-ID No. 20) NIGSKS | (Seq.-ID No. 68) VHWYQQKPG QAPVLVIY | (Seq.-ID No. 26) NDS | (Seq.-ID No. 74) DRPSGIPERFSGSNSGKTAT LTISRVEAGDEADYYC | (Seq.-ID No. 32) QVWDSSID WV | (Seq.-ID No. 80) FGGGTKL TVL |
| HT220-M-D1 | (Seq.-ID No. 63) QSVLTQPPSVSVVPGK TARIICGGN | (Seq.-ID No. 21) NIGSKS | (Seq.-ID No. 69) VHWYQQKPG QAPALVIY | (Seq.-ID No. 27) NNS | (Seq.-ID No. 75) DRPSGIPERFSGSNSGNMAT LTISRVEAGDESDYYC | (Seq.-ID No. 33) QVWDSSSD WV | (Seq.-ID No. 81) FGGGTRL TIL |
| HT220-M-G8 | (Seq.-ID No. 64) QSVLTQPPSVSVAPGK TARITCGGN | (Seq.-ID No. 22) NIGSKS | (Seq.-ID No. 70) VHWYQQKPG QAPVLVIY | (Seq.-ID No. 28) YGS | (Seq.-ID No. 76) DRPSGIPERFSGSNTGNMAT LTISRVEAGDEADYYC | (Seq.-ID No. 34) QVWDSSSD WV | (Seq.-ID No. 82) FGGGTKL TVL |
| HT186-B7 | (Seq.-ID No. 65) QSVLTQPPSVSVAPGK TARITCGGN | (Seq.-ID No. 23) NIGSKS | (Seq.-ID No. 71) VHWYQQKPG QAPALVIY | (Seq.-ID No. 29) YGS | (Seq.-ID No. 77) YRPSGIPERFSGSNYGNTAT LTIRRVEAGDEADYYC | (Seq.-ID No. 35) QVWDSSSD WV | (Seq.-ID No. 83) FGGGTKL TVL |
| HT186-G2 | (Seq.-ID No. 66) QSVLTQPPSVSVAPGK TARITCGGN | (Seq.-ID No. 24) NIGSKS | (Seq.-ID No. 72) VHWYQQKPG QAPVLVIY | (Seq.-ID No. 30) YGS | (Seq.-ID No. 78) DRSSGIPERFSGSNSGNTAT LTISRVEAGDEADYYC | (Seq.-ID No. 36) QVWDSSSD WV | (Seq.-ID No. 84) FGGGTKL TVL |

Fig. 1 B

| | VH |
|---|---|
| HT186-D11 | (Seq.-ID No. 85)<br>QMQLVQSEAELKKPGASVKVSCKAS GYSFTGHY MHWVRQAPGQGLEWMGW IDPVTGGT KYAQNFQGWVTMTRDTSIRTAYLELSRLRSDDTAMYYC AREVTGDRGQFDK WGQGTLVTVAS |
| HT200-3A-C1 | (Seq.-ID No. 86)<br>QMQLVQSGAEVKKPGASVKVSCKAS GYTFTGHY MHWVRQAPGQGLEWMGW IDPVTGGT KYAQNFQGWVTMTRDTSIRTAYMELSRLRSDDTAMYYC AREVTGDRGQFDK WGQGTLVTVAS |
| HT220-M-D1 | (Seq.-ID No. 87)<br>QMLLVQSGAEAKKPGASVKVSCKAS GYTFTGHY MHWVRQAPGQGLEWMGW IDPVTGGT KYAQNFQGWVTMTRDTSIRTAYMELSRLRPDDTAMYYC AREVTGDRGQFDK WGQGTLVTVAS |
| HT220-M-G8 | (Seq.-ID No. 88)<br>QMQLVQSGAEVMKPGASVKVSCKAS GYSFTGHY MHWVRHAPGQGLEWMGW IDPVTGST KYAQNFQGWVTMTRDTSISTAYMELSRLRSDDTAMYYC AREVTGDRGQFDK WGQGTLVTVAS |
| HT186-B7 | (Seq.-ID No. 89)<br>QMQLVQSGAEVKKPGASVKVSCKAS GYTFTGHY MHWVRQAPGQGLEWMGW IDPVTGGT KYAQNFQGWVTMTRDTSIRTAYMELSRLRSDDTAMYYC AREVTGDRGQFDK WGQGTLVTVAS |
| HT186-G2 | (Seq.-ID No. 90)<br>RMQLVQSGAEVKKPGASVKLSCKAS GYTFAGHY MHWVRQAPGRGLEWMGW IDPVTGGT KYAQNFQGWVTMTRDTSIRTAYMELSRLRSDDTAMYYC AREVTGDRGQFDK WGQGTLVTVAS |

Fig. 1 B (cont.)

| | VL |
|---|---|
| HT186-D11 | (Seq.-ID No. 91)<br>QSVLTQPPSVSVAPGKTARITCGGN NIGSKS VHWYQQKPGQAPAL VIY YGS NRPSGIPERFSGSNSGNTATLTISRVEAGDEADYYC QVWDSSSIDWV FGGGTKLTVL |
| HT200-3A-C1 | (Seq.-ID No. 92)<br>QSVLTQPPSVSVSMAPGETARITCGGN NIGSKS VHWYQQKPGQAPVL VIY NDS DRPSGIPERFSGSNSGKTATLTISRVEAGDEADYYC QVWDSSSIDWV FGGGTKLTVL |
| HT220-M-D1 | (Seq.-ID No. 93)<br>QSVLTQPPSVSVVPGKTARIICGGN NIGSKS VHWYQQKPGQAPVL VIY NNS DRPSGIPERFSGSNSGNMATLTISRVEAGDESDYYC QVWDSSSSDWV FGGGTRLTIL |
| HT220-M-G8 | (Seq.-ID No. 94)<br>QSVLTQPPSVSVAPGKTARITCGGN NIGSKS VHWYQQKPGQAPVL VIY YGS DRPSGIPERFSGSNTGNMATLTIRRVEAGDEADYYC QVWDSSSSDWV FGGGTKLTVL |
| HT186-B7 | (Seq.-ID No. 95)<br>QSVLTQPPSVSVAPGKTARITCGGN NIGSKS VHWYQQKPGQAPAL VIY YGS YRPSGIPERFSGSNYGNTATLTIRRVEAGDEADYYC QVWDSSSSDWV FGGGTKLTVL |
| HT186-G2 | (Seq.-ID No. 96)<br>QSVLTQPPSVSVAPGKTARITCGGN NIGSKS VHWYQQKPGQAPVL VIY YGS DRSSGIPERFSGSNSGNTATLTISRVEAGDEADYYC QVWDSSSSDWV FGGGTKLTVL |

Fig. 1 C

| | VH | N'IgG1 CH1 | YOL-Linker | VL | N' IgG1 CL can one speak about IgG1 CL? Normally one has VL-CL that can combine with all antibody heavy chains incl. IgD, IgA etc. |
|---|---|---|---|---|---|
| HT186-D11 | Seq.-ID No. 85 | (Seq.-ID No. 97) SSTKGPSVKL | (Seq.-ID No. 103) EEGEFSEARV | Seq.-ID No. 91 | (Seq.-ID No. 109) GQPKAAPSVTLFPSS |
| HT200-3A-C1 | Seq.-ID No. 86 | (Seq.-ID No. 98) ASTKGPSAKL | (Seq.-ID No. 104) EEGEFSEARV | Seq.-ID No. 92 | (Seq.-ID No. 110) GQPKAAPSVTLFPPS |
| HT220-M-D1 | Seq.-ID No. 87 | (Seq.-ID No. 99) ASTKGPSVKL | (Seq.-ID No. 105) EEGEFSEARV | Seq.-ID No. 93 | (Seq.-ID No. 111) GQSKAAPSVTLFPPS |
| HT220-M-G8 | Seq.-ID No. 88 | (Seq.-ID No. 100) ASTKGPSVKL | (Seq.-ID No. 106) EEGEFSEARV | Seq.-ID No. 94 | (Seq.-ID No. 112) GQPKAAPSVTLFPPS |
| HT186-B7 | Seq.-ID No. 89 | (Seq.-ID No. 101) ASTKGPSVKL | (Seq.-ID No. 107) EEGEFSEARV | Seq.-ID No. 95 | (Seq.-ID No. 113) GQPKAAPSVTLFPPS |
| HT186-G2 | Seq.-ID No. 90 | (Seq.-ID No. 102) ASTKGPSVKL | (Seq.-ID No. 108) EEGKFLEAHV | Seq.-ID No. 96 | (Seq.-ID No. 114) GQPKAAPSVTLFPPS |

N' IgG1 CH1 and N' IgG1 CL mean that only the first N-terminal amino acids of the CH1 or CL region respectively were present in the scFv. This is due to cloning and stabilization reasons.

Maybe it is more precise if it will be mentioned as "N-terminal amino acids of CH1 / CL region present in scFv"?

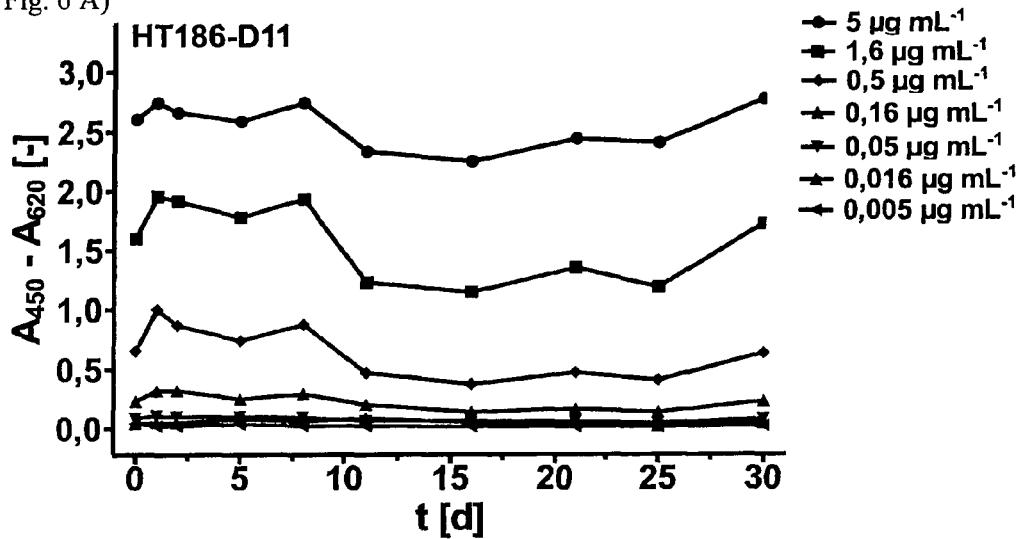
Fig. 6 A) HT186-D11
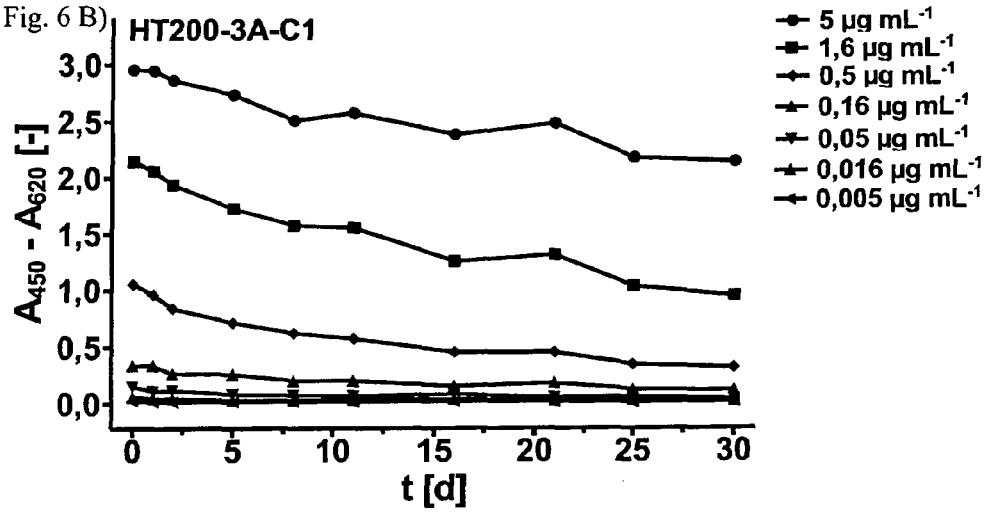
Fig. 6 B) HT200-3A-C1
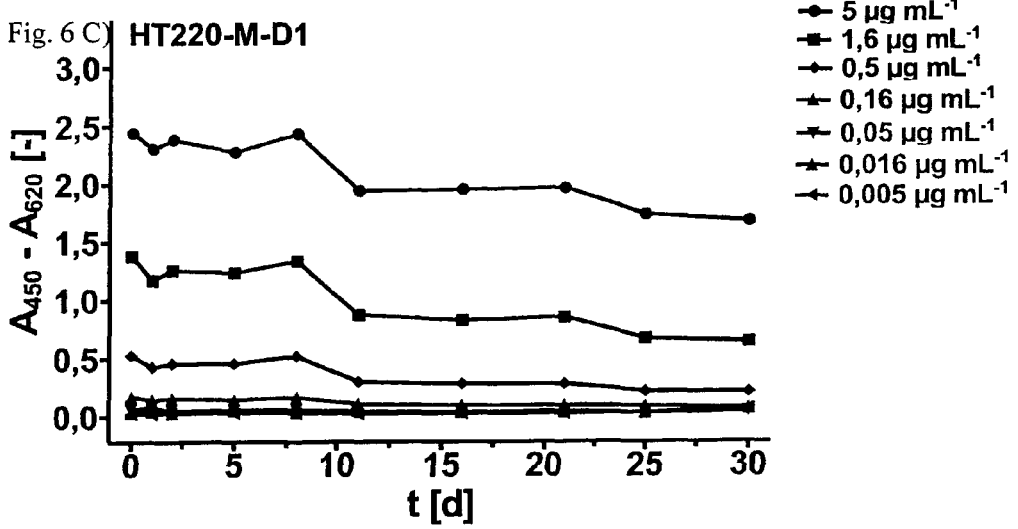
Fig. 6 C) HT220-M-D1

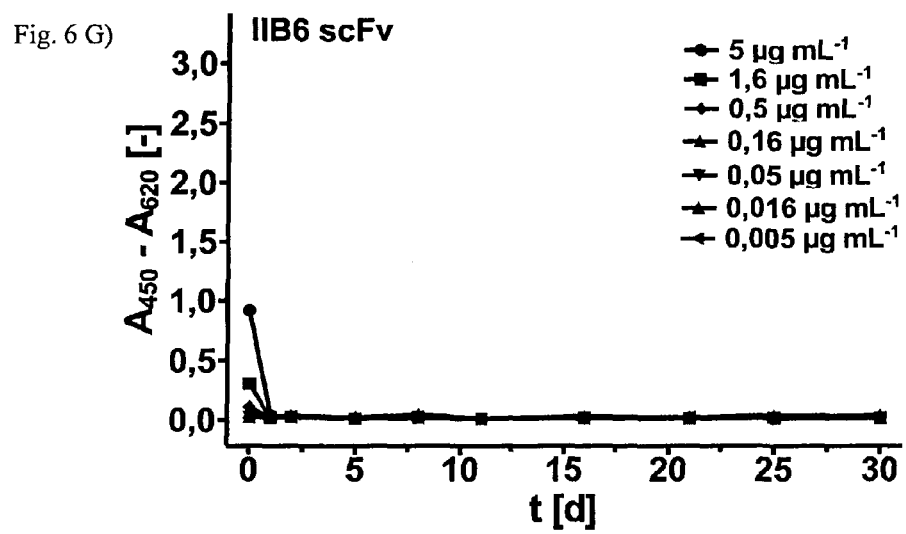

```
                              SEQUENCE LISTING

<160> NUMBER OF SEQ ID NOS: 138

<210> SEQ ID NO 1
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 1

Gly Tyr Ser Phe Thr Gly His Tyr
1               5

<210> SEQ ID NO 2
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 2

Gly Tyr Thr Phe Thr Gly His Tyr
1               5

<210> SEQ ID NO 3
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 3

Gly Tyr Thr Phe Thr Gly His Tyr
1               5

<210> SEQ ID NO 4
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 4

Gly Tyr Ser Phe Thr Gly His Tyr
1               5

<210> SEQ ID NO 5
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 5

Gly Tyr Thr Phe Thr Gly His Tyr
1               5

<210> SEQ ID NO 6
```

```
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 6

Gly Tyr Thr Phe Ala Gly His Tyr
1               5

<210> SEQ ID NO 7
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 7

Ile Asp Pro Val Thr Gly Gly Thr
1               5

<210> SEQ ID NO 8
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 8

Ile Asp Pro Val Thr Gly Gly Thr
1               5

<210> SEQ ID NO 9
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 9

Ile Asp Pro Val Thr Gly Gly Thr
1               5

<210> SEQ ID NO 10
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 10

Ile Asp Pro Val Thr Gly Ser Thr
1               5

<210> SEQ ID NO 11
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 11
```

Ile Asp Pro Val Thr Gly Gly Thr
1               5

<210> SEQ ID NO 12
<211> LENGTH: 8
<212> TYPE: PRT
<213> ORGANISM: Artificial sequence
<220> FEATURE:
<223> OTHER INFORMATION: antigene specific peptide against the human
      gene product MUC 1

<400> SEQUENCE: 12

Ile Asp Pro Val Thr Gly Gly Thr
1               5

<210> SEQ ID NO 13
<211> LENGTH: 13
<212> TYPE: PRT
<213> ORGANISM: Artificial sequence
<220> FEATURE:
<223> OTHER INFORMATION: antigene specific peptide against the human
      gene product MUC 1

<400> SEQUENCE: 13

Ala Arg Glu Val Thr Gly Asp Arg Gly Gln Phe Asp Lys
1               5                   10

<210> SEQ ID NO 14
<211> LENGTH: 13
<212> TYPE: PRT
<213> ORGANISM: Artificial sequence
<220> FEATURE:
<223> OTHER INFORMATION: antigene specific peptide against the human
      gene product MUC 1

<400> SEQUENCE: 14

Ala Arg Glu Val Thr Gly Asp Arg Gly Gln Phe Asp Lys
1               5                   10

<210> SEQ ID NO 15
<211> LENGTH: 13
<212> TYPE: PRT
<213> ORGANISM: Artificial sequence
<220> FEATURE:
<223> OTHER INFORMATION: antigene specific peptide against the human
      gene product MUC 1

<400> SEQUENCE: 15

Ala Arg Glu Val Thr Gly Asp Arg Gly Gln Phe Asp Lys
1               5                   10

<210> SEQ ID NO 16
<211> LENGTH: 13
<212> TYPE: PRT
<213> ORGANISM: Artificial sequence
<220> FEATURE:
<223> OTHER INFORMATION: antigene specific peptide against the human
      gene product MUC 1

<400> SEQUENCE: 16

Ala Arg Glu Val Thr Gly Asp Arg Gly Gln Phe Asp Lys
1               5                   10

<210> SEQ ID NO 17
<211> LENGTH: 13
<212> TYPE: PRT
<213> ORGANISM: Artificial sequence
<220> FEATURE:

```
<223> OTHER INFORMATION: antigene specific peptide against the human
      gene product MUC 1

<400> SEQUENCE: 17

Ala Arg Glu Val Thr Gly Asp Arg Gly Gln Phe Asp Lys
1               5                   10

<210> SEQ ID NO 18
<211> LENGTH: 13
<212> TYPE: PRT
<213> ORGANISM: Artificial sequence
<220> FEATURE:
<223> OTHER INFORMATION: antigene specific peptide against the human
      gene product MUC 1

<400> SEQUENCE: 18

Ala Arg Glu Val Thr Gly Asp Arg Gly Gln Phe Asp Lys
1               5                   10

<210> SEQ ID NO 19
<211> LENGTH: 6
<212> TYPE: PRT
<213> ORGANISM: Artificial sequence
<220> FEATURE:
<223> OTHER INFORMATION: antigene specific peptide against the human
      gene product MUC 1

<400> SEQUENCE: 19

Asn Ile Gly Ser Lys Ser
1               5

<210> SEQ ID NO 20
<211> LENGTH: 6
<212> TYPE: PRT
<213> ORGANISM: Artificial sequence
<220> FEATURE:
<223> OTHER INFORMATION: antigene specific peptide against the human
      gene product MUC 1

<400> SEQUENCE: 20

Asn Ile Gly Ser Lys Ser
1               5

<210> SEQ ID NO 21
<211> LENGTH: 6
<212> TYPE: PRT
<213> ORGANISM: Artificial sequence
<220> FEATURE:
<223> OTHER INFORMATION: antigene specific peptide against the human
      gene product MUC 1

<400> SEQUENCE: 21

Asn Ile Gly Ser Lys Ser
1               5

<210> SEQ ID NO 22
<211> LENGTH: 6
<212> TYPE: PRT
<213> ORGANISM: Artificial sequence
<220> FEATURE:
<223> OTHER INFORMATION: antigene specific peptide against the human
      gene product MUC 1

<400> SEQUENCE: 22

Asn Ile Gly Ser Lys Ser
1               5
```

```
<210> SEQ ID NO 23
<211> LENGTH: 6
<212> TYPE: PRT
<213> ORGANISM: Artificial sequence
<220> FEATURE:
<223> OTHER INFORMATION: antigene specific peptide against the human
      gene product MUC 1

<400> SEQUENCE: 23

Asn Ile Gly Ser Lys Ser
1               5

<210> SEQ ID NO 24
<211> LENGTH: 6
<212> TYPE: PRT
<213> ORGANISM: Artificial sequence
<220> FEATURE:
<223> OTHER INFORMATION: antigene specific peptide against the human
      gene product MUC 1

<400> SEQUENCE: 24

Asn Ile Gly Ser Lys Ser
1               5

<210> SEQ ID NO 25
<211> LENGTH: 3
<212> TYPE: PRT
<213> ORGANISM: Artificial sequence
<220> FEATURE:
<223> OTHER INFORMATION: antigene specific peptide against the human
      gene product MUC 1

<400> SEQUENCE: 25

Tyr Gly Ser
1

<210> SEQ ID NO 26
<211> LENGTH: 3
<212> TYPE: PRT
<213> ORGANISM: Artificial sequence
<220> FEATURE:
<223> OTHER INFORMATION: antigene specific peptide against the human
      gene product MUC 1

<400> SEQUENCE: 26

Asn Asp Ser
1

<210> SEQ ID NO 27
<211> LENGTH: 3
<212> TYPE: PRT
<213> ORGANISM: Artificial sequence
<220> FEATURE:
<223> OTHER INFORMATION: antigene specific peptide against the human
      gene product MUC 1

<400> SEQUENCE: 27

Asn Asn Ser
1

<210> SEQ ID NO 28
<211> LENGTH: 3
<212> TYPE: PRT
<213> ORGANISM: Artificial sequence
<220> FEATURE:
<223> OTHER INFORMATION: antigene specific peptide against the human
      gene product MUC 1

<400> SEQUENCE: 28
```

Tyr Gly Ser
1

<210> SEQ ID NO 29
<211> LENGTH: 3
<212> TYPE: PRT
<213> ORGANISM: Artificial sequence
<220> FEATURE:
<223> OTHER INFORMATION: antigene specific peptide against the human
      gene product MUC 1

<400> SEQUENCE: 29

Tyr Gly Ser
1

<210> SEQ ID NO 30
<211> LENGTH: 3
<212> TYPE: PRT
<213> ORGANISM: Artificial sequence
<220> FEATURE:
<223> OTHER INFORMATION: antigene specific peptide against the human
      gene product MUC 1

<400> SEQUENCE: 30

Tyr Gly Ser
1

<210> SEQ ID NO 31
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 31

Gln Val Trp Asp Ser Ser Ser Asp Trp Val
1               5                   10

<210> SEQ ID NO 32
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 32

Gln Val Trp Asp Ser Ser Ile Asp Trp Val
1               5                   10

<210> SEQ ID NO 33
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 33

Gln Val Trp Asp Ser Ser Ser Asp Trp Val
1               5                   10

<210> SEQ ID NO 34
<211> LENGTH: 10
<212> TYPE: PRT
<213> ORGANISM: Artificial sequence

```
<220> FEATURE:
<223> OTHER INFORMATION: antigene specific peptide against the human
      gene product MUC 1

<400> SEQUENCE: 34

Gln Val Trp Asp Ser Ser Ser Asp Trp Val
1               5                   10

<210> SEQ ID NO 35
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 35

Gln Val Trp Asp Ser Ser Ser Asp Trp Val
1               5                   10

<210> SEQ ID NO 36
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 36

Gln Val Trp Asp Ser Ser Ser Asp Trp Val
1               5                   10

<210> SEQ ID NO 37
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 37

Gln Met Gln Leu Val Gln Ser Glu Ala Glu Leu Lys Lys Pro Gly Ala
1               5                   10                  15

Ser Val Lys Val Ser Cys Lys Ala Ser
            20                  25

<210> SEQ ID NO 38
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 38

Gln Met Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 39
<211> LENGTH: 25
<212> TYPE: PRT
<213> ORGANISM: Artificial sequence
<220> FEATURE:
<223> OTHER INFORMATION: antigene specific peptide against the human
      gene product MUC 1
```

<400> SEQUENCE: 39

Gln Met Leu Leu Val Gln Ser Gly Ala Glu Ala Lys Lys Pro Gly Ala
1               5                   10                  15

Ser Val Lys Val Ser Cys Lys Ala Ser
            20                  25

<210> SEQ ID NO 40
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 40

Gln Met Gln Leu Val Gln Ser Gly Ala Glu Val Met Lys Pro Gly Ala
1               5                   10                  15

Ser Val Lys Val Ser Cys Lys Ala Ser
            20                  25

<210> SEQ ID NO 41
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 41

Gln Met Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 42
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 42

Arg Met Gln Leu Val Gln Ser Gly Ala Glu Val Lys Lys Pro Gly Ala
1               5                   10                  15

Ser Val Lys Leu Ser Cys Lys Ala Ser
            20                  25

<210> SEQ ID NO 43
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 43

Met His Trp Val Arg Gln Ala Pro Gly Gln Gly Leu Glu Trp Met Gly
1               5                   10                  15

Trp

<210> SEQ ID NO 44
<211> LENGTH: 17

```
<212> TYPE: PRT
<213> ORGANISM: Artificial sequence
<220> FEATURE:
<223> OTHER INFORMATION: antigene specific peptide against the human
      gene product MUC 1

<400> SEQUENCE: 44

Met His Trp Val Arg Gln Ala Pro Gly Gln Gly Leu Glu Trp Met Gly
1               5                   10                  15

Trp

<210> SEQ ID NO 45
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 45

Met His Trp Val Arg Gln Ala Pro Gly Gln Gly Leu Glu Trp Met Gly
1               5                   10                  15

Trp

<210> SEQ ID NO 46
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 46

Met His Trp Val Arg His Ala Pro Gly Gln Gly Leu Glu Trp Met Gly
1               5                   10                  15

Trp

<210> SEQ ID NO 47
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 47

Met His Trp Val Arg Gln Ala Pro Gly Gln Gly Leu Glu Trp Met Gly
1               5                   10                  15

Trp

<210> SEQ ID NO 48
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 48

Met His Trp Val Arg Gln Ala Pro Gly Arg Gly Leu Glu Trp Met Gly
1               5                   10                  15

Trp

<210> SEQ ID NO 49
```

```
<211> LENGTH: 38
<212> TYPE: PRT
<213> ORGANISM: Artificial sequence
<220> FEATURE:
<223> OTHER INFORMATION: antigene specific peptide against the human
      gene product MUC 1

<400> SEQUENCE: 49

Lys Tyr Ala Gln Asn Phe Gln Gly Trp Val Thr Met Thr Arg Asp Thr
1               5                   10                  15

Ser Ile Arg Thr Ala Tyr Leu Glu Leu Ser Arg Leu Arg Ser Asp Asp
            20                  25                  30

Thr Ala Met Tyr Tyr Cys
        35

<210> SEQ ID NO 50
<211> LENGTH: 38
<212> TYPE: PRT
<213> ORGANISM: Artificial sequence
<220> FEATURE:
<223> OTHER INFORMATION: antigene specific peptide against the human
      gene product MUC 1

<400> SEQUENCE: 50

Lys Tyr Ala Gln Asn Phe Gln Gly Trp Val Thr Met Thr Arg Asp Thr
1               5                   10                  15

Ser Ile Arg Thr Ala Tyr Met Glu Leu Ser Arg Leu Arg Ser Asp Asp
            20                  25                  30

Thr Ala Met Tyr Tyr Cys
        35

<210> SEQ ID NO 51
<211> LENGTH: 38
<212> TYPE: PRT
<213> ORGANISM: Artificial sequence
<220> FEATURE:
<223> OTHER INFORMATION: antigene specific peptide against the human
      gene product MUC 1

<400> SEQUENCE: 51

Lys Tyr Ala Gln Asn Phe Gln Gly Trp Val Thr Met Thr Arg Asp Thr
1               5                   10                  15

Ser Ile Arg Thr Ala Tyr Met Glu Leu Ser Arg Leu Arg Pro Asp Asp
            20                  25                  30

Thr Ala Met Tyr Tyr Cys
        35

<210> SEQ ID NO 52
<211> LENGTH: 38
<212> TYPE: PRT
<213> ORGANISM: Artificial sequence
<220> FEATURE:
<223> OTHER INFORMATION: antigene specific peptide against the human
      gene product MUC 1

<400> SEQUENCE: 52

Lys Tyr Ala Gln Asn Phe Gln Gly Trp Val Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Met Tyr Tyr Cys
        35
```

```
<210> SEQ ID NO 53
<211> LENGTH: 38
<212> TYPE: PRT
<213> ORGANISM: Artificial sequence
<220> FEATURE:
<223> OTHER INFORMATION: antigene specific peptide against the human
      gene product MUC 1

<400> SEQUENCE: 53

Lys Tyr Ala Gln Asn Phe Gln Gly Trp Val Thr Met Thr Arg Asp Thr
1               5                   10                  15

Ser Ile Arg Thr Ala Tyr Met Glu Leu Ser Arg Leu Arg Ser Asp Asp
                20                  25                  30

Thr Ala Met Tyr Tyr Cys
        35

<210> SEQ ID NO 54
<211> LENGTH: 38
<212> TYPE: PRT
<213> ORGANISM: Artificial sequence
<220> FEATURE:
<223> OTHER INFORMATION: antigene specific peptide against the human
      gene product MUC 1

<400> SEQUENCE: 54

Lys Tyr Ala Gln Asn Phe Gln Gly Trp Val Thr Met Thr Arg Asp Thr
1               5                   10                  15

Ser Ile Arg Thr Ala Tyr Met Glu Leu Ser Arg Leu Arg Ser Asp Asp
                20                  25                  30

Thr Ala Met Tyr Tyr Cys
        35

<210> SEQ ID NO 55
<211> LENGTH: 11
<212> TYPE: PRT
<213> ORGANISM: Artificial sequence
<220> FEATURE:
<223> OTHER INFORMATION: antigene specific peptide against the human
      gene product MUC 1

<400> SEQUENCE: 55

Trp Gly Gln Gly Thr Leu Val Thr Val Ala Ser
1               5                   10

<210> SEQ ID NO 56
<211> LENGTH: 11
<212> TYPE: PRT
<213> ORGANISM: Artificial sequence
<220> FEATURE:
<223> OTHER INFORMATION: antigene specific peptide against the human
      gene product MUC 1

<400> SEQUENCE: 56

Trp Gly Gln Gly Thr Leu Val Thr Val Ala Ser
1               5                   10

<210> SEQ ID NO 57
<211> LENGTH: 11
<212> TYPE: PRT
<213> ORGANISM: Artificial sequence
<220> FEATURE:
<223> OTHER INFORMATION: antigene specific peptide against the human
      gene product MUC 1

<400> SEQUENCE: 57

Trp Gly Gln Gly Thr Leu Val Thr Val Ala Ser
```

```
<210> SEQ ID NO 58
<211> LENGTH: 11
<212> TYPE: PRT
<213> ORGANISM: Artificial sequence
<220> FEATURE:
<223> OTHER INFORMATION: antigene specific peptide against the human
      gene product MUC 1

<400> SEQUENCE: 58

Trp Gly Gln Gly Thr Leu Val Thr Val Ala Ser
1               5                   10

<210> SEQ ID NO 59
<211> LENGTH: 11
<212> TYPE: PRT
<213> ORGANISM: Artificial sequence
<220> FEATURE:
<223> OTHER INFORMATION: antigene specific peptide against the human
      gene product MUC 1

<400> SEQUENCE: 59

Trp Gly Gln Gly Thr Leu Val Thr Val Ala Ser
1               5                   10

<210> SEQ ID NO 60
<211> LENGTH: 11
<212> TYPE: PRT
<213> ORGANISM: Artificial sequence
<220> FEATURE:
<223> OTHER INFORMATION: antigene specific peptide against the human
      gene product MUC 1

<400> SEQUENCE: 60

Trp Gly Gln Gly Thr Leu Val Thr Val Ala Ser
1               5                   10

<210> SEQ ID NO 61
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 61

Gln Ser Val Leu Thr Gln Pro Pro Ser Val Ser Val Ala Pro Gly Lys
1               5                   10                  15

Thr Ala Arg Ile Thr Cys Gly Gly Asn
            20                  25

<210> SEQ ID NO 62
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 62

Gln Ser Val Leu Thr Gln Pro Pro Ser Val Ser Met Ala Pro Gly Glu
1               5                   10                  15

Thr Ala Arg Ile Thr Cys Gly Gly Asn
            20                  25
```

```
<210> SEQ ID NO 63
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 63

Gln Ser Val Leu Thr Gln Pro Pro Ser Val Ser Val Val Pro Gly Lys
1               5                   10                  15

Thr Ala Arg Ile Ile Cys Gly Gly Asn
            20                  25

<210> SEQ ID NO 64
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 64

Gln Ser Val Leu Thr Gln Pro Pro Ser Val Ser Val Ala Pro Gly Lys
1               5                   10                  15

Thr Ala Arg Ile Thr Cys Gly Gly Asn
            20                  25

<210> SEQ ID NO 65
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 65

Gln Ser Val Leu Thr Gln Pro Pro Ser Val Ser Val Ala Pro Gly Lys
1               5                   10                  15

Thr Ala Arg Ile Thr Cys Gly Gly Asn
            20                  25

<210> SEQ ID NO 66
<211> LENGTH: 25
<212> TYPE: PRT
<213> ORGANISM: Artificial sequence
<220> FEATURE:
<223> OTHER INFORMATION: antigene specific peptide against the human
      gene product MUC 1

<400> SEQUENCE: 66

Gln Ser Val Leu Thr Gln Pro Pro Ser Val Ser Val Ala Pro Gly Lys
1               5                   10                  15

Thr Ala Arg Ile Thr Cys Gly Gly Asn
            20                  25

<210> SEQ ID NO 67
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 67

Val His Trp Tyr Gln Gln Lys Pro Gly Gln Ala Pro Ala Leu Val Ile
```

```
1               5                   10                  15
Tyr

<210> SEQ ID NO 68
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 68

Val His Trp Tyr Gln Gln Lys Pro Gly Gln Ala Pro Val Leu Val Ile
1               5                   10                  15

Tyr

<210> SEQ ID NO 69
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 69

Val His Trp Tyr Gln Gln Lys Pro Gly Gln Ala Pro Val Leu Val Ile
1               5                   10                  15

Tyr

<210> SEQ ID NO 70
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 70

Val His Trp Tyr Gln Gln Lys Pro Gly Gln Ala Pro Val Leu Val Ile
1               5                   10                  15

Tyr

<210> SEQ ID NO 71
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 71

Val His Trp Tyr Gln Gln Lys Pro Gly Gln Ala Pro Ala Leu Val Ile
1               5                   10                  15

Tyr

<210> SEQ ID NO 72
<211> LENGTH: 17
<212> TYPE: PRT
<213> ORGANISM: Artificial sequence
<220> FEATURE:
<223> OTHER INFORMATION: antigene specific peptide against the human
      gene product MUC 1

<400> SEQUENCE: 72
```

```
Val His Trp Tyr Gln Gln Lys Pro Gly Gln Ala Pro Val Leu Val Ile
1               5                   10                  15

Tyr

<210> SEQ ID NO 73
<211> LENGTH: 36
<212> TYPE: PRT
<213> ORGANISM: Artificial sequence
<220> FEATURE:
<223> OTHER INFORMATION: antigene specific peptide against the human
      gene product MUC 1

<400> SEQUENCE: 73

Asn Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
            35

<210> SEQ ID NO 74
<211> LENGTH: 36
<212> TYPE: PRT
<213> ORGANISM: Artificial sequence
<220> FEATURE:
<223> OTHER INFORMATION: antigene specific peptide against the human
      gene product MUC 1

<400> SEQUENCE: 74

Asp Arg Pro Ser Gly Ile Pro Glu Arg Phe Ser Gly Ser Asn Ser Gly
1               5                   10                  15

Lys Thr Ala Thr Leu Thr Ile Ser Arg Val Glu Ala Gly Asp Glu Ala
            20                  25                  30

Asp Tyr Tyr Cys
            35

<210> SEQ ID NO 75
<211> LENGTH: 36
<212> TYPE: PRT
<213> ORGANISM: Artificial sequence
<220> FEATURE:
<223> OTHER INFORMATION: antigene specific peptide against the human
      gene product MUC 1

<400> SEQUENCE: 75

Asp Arg Pro Ser Gly Ile Pro Glu Arg Phe Ser Gly Ser Asn Ser Gly
1               5                   10                  15

Asn Met Ala Thr Leu Thr Ile Ser Arg Val Glu Ala Gly Asp Glu Ser
            20                  25                  30

Asp Tyr Tyr Cys
            35

<210> SEQ ID NO 76
<211> LENGTH: 36
<212> TYPE: PRT
<213> ORGANISM: Artificial sequence
<220> FEATURE:
<223> OTHER INFORMATION: antigene specific peptide against the human
      gene product MUC 1

<400> SEQUENCE: 76

Asp Arg Pro Ser Gly Ile Pro Glu Arg Phe Ser Gly Ser Asn Thr Gly
1               5                   10                  15
```

Asn Met Ala Thr Leu Thr Ile Ser Arg Val Glu Ala Gly Asp Glu Ala
            20                  25                  30

Asp Tyr Tyr Cys
        35

<210> SEQ ID NO 77
<211> LENGTH: 36
<212> TYPE: PRT
<213> ORGANISM: Artificial sequence
<220> FEATURE:
<223> OTHER INFORMATION: antigene specific peptide against the human
      gene product MUC 1

<400> SEQUENCE: 77

Tyr Arg Pro Ser Gly Ile Pro Glu Arg Phe Ser Gly Ser Asn Tyr Gly
1               5                   10                  15

Asn Thr Ala Thr Leu Thr Ile Arg Arg Val Glu Ala Gly Asp Glu Ala
            20                  25                  30

Asp Tyr Tyr Cys
        35

<210> SEQ ID NO 78
<211> LENGTH: 36
<212> TYPE: PRT
<213> ORGANISM: Artificial sequence
<220> FEATURE:
<223> OTHER INFORMATION: antigene specific peptide against the human
      gene product MUC 1

<400> SEQUENCE: 78

Asp Arg Ser Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
        35

<210> SEQ ID NO 79
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 79

Phe Gly Gly Gly Thr Lys Leu Thr Val Leu
1               5                   10

<210> SEQ ID NO 80
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 80

Phe Gly Gly Gly Thr Lys Leu Thr Val Leu
1               5                   10

<210> SEQ ID NO 81
<211> LENGTH: 10
<212> TYPE: PRT
<213> ORGANISM: Artificial sequence

```
<220> FEATURE:
<223> OTHER INFORMATION: antigene specific peptide against the human
      gene product MUC 1

<400> SEQUENCE: 81

Phe Gly Gly Gly Thr Arg Leu Thr Ile Leu
1               5                   10

<210> SEQ ID NO 82
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 82

Phe Gly Gly Gly Thr Lys Leu Thr Val Leu
1               5                   10

<210> SEQ ID NO 83
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 83

Phe Gly Gly Gly Thr Lys Leu Thr Val Leu
1               5                   10

<210> SEQ ID NO 84
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 84

Phe Gly Gly Gly Thr Lys Leu Thr Val Leu
1               5                   10

<210> SEQ ID NO 85
<211> LENGTH: 120
<212> TYPE: PRT
<213> ORGANISM: Artificial sequence
<220> FEATURE:
<223> OTHER INFORMATION: antigene specific peptide against the human
      gene product MUC 1

<400> SEQUENCE: 85

Gln Met Gln Leu Val Gln Ser Glu Ala Glu Leu Lys Lys Pro Gly Ala
1               5                   10                  15

Ser Val Lys Val Ser Cys Lys Ala Ser Gly Tyr Ser Phe Thr Gly His
                20                  25                  30

Tyr Met His Trp Val Arg Gln Ala Pro Gly Gln Gly Leu Glu Trp Met
            35                  40                  45

Gly Trp Ile Asp Pro Val Thr Gly Gly Thr Lys Tyr Ala Gln Asn Phe
        50                  55                  60

Gln Gly Trp Val Thr Met Thr Arg Asp Thr Ser Ile Arg Thr Ala Tyr
65                  70                  75                  80

Leu Glu Leu Ser Arg Leu Arg Ser Asp Asp Thr Ala Met Tyr Tyr Cys
                85                  90                  95
```

Ala Arg Glu Val Thr Gly Asp Arg Gly Gln Phe Asp Lys Trp Gly Gln
            100                 105                 110

Gly Thr Leu Val Thr Val Ala Ser
        115                 120

<210> SEQ ID NO 86
<211> LENGTH: 120
<212> TYPE: PRT
<213> ORGANISM: Artificial sequence
<220> FEATURE:
<223> OTHER INFORMATION: antigene specific peptide against the human
      gene product MUC 1

<400> SEQUENCE: 86

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Asp Pro Val Thr Gly Gly Thr Lys Tyr Ala Gln Asn Phe
    50                  55                  60

Gln Gly Trp Val Thr Met Thr Arg Asp Thr Ser Ile Arg Thr Ala Tyr
65                  70                  75                  80

Met Glu Leu Ser Arg Leu Arg Ser Asp Asp Thr Ala Met Tyr Tyr Cys
                85                  90                  95

Ala Arg Glu Val Thr Gly Asp Arg Gly Gln Phe Asp Lys Trp Gly Gln
            100                 105                 110

Gly Thr Leu Val Thr Val Ala Ser
        115                 120

<210> SEQ ID NO 87
<211> LENGTH: 120
<212> TYPE: PRT
<213> ORGANISM: Artificial sequence
<220> FEATURE:
<223> OTHER INFORMATION: antigene specific peptide against the human
      gene product MUC 1

<400> SEQUENCE: 87

Gln Met Leu Leu Val Gln Ser Gly Ala Glu Ala Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Asp Pro Val Thr Gly Gly Thr Lys Tyr Ala Gln Asn Phe
    50                  55                  60

Gln Gly Trp Val Thr Met Thr Arg Asp Thr Ser Ile Arg Thr Ala Tyr
65                  70                  75                  80

Met Glu Leu Ser Arg Leu Arg Pro Asp Asp Thr Ala Met Tyr Tyr Cys
                85                  90                  95

Ala Arg Glu Val Thr Gly Asp Arg Gly Gln Phe Asp Lys Trp Gly Gln
            100                 105                 110

Gly Thr Leu Val Thr Val Ala Ser
        115                 120

<210> SEQ ID NO 88

```
<211> LENGTH: 120
<212> TYPE: PRT
<213> ORGANISM: Artificial sequence
<220> FEATURE:
<223> OTHER INFORMATION: antigene specific peptide against the human
      gene product MUC 1

<400> SEQUENCE: 88
```

| Gln | Met | Gln | Leu | Val | Gln | Ser | Gly | Ala | Glu | Val | Met | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Ser | Phe | Thr | Gly | His |
|---|---|---|---|---|---|---|---|---|---|---|---|---|---|---|---|
| | | | 20 | | | | | 25 | | | | | 30 | | |

| Tyr | Met | His | Trp | Val | Arg | His | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Trp | Ile | Asp | Pro | Val | Thr | Gly | Ser | Thr | Lys | Tyr | Ala | Gln | Asn | Phe |
|---|---|---|---|---|---|---|---|---|---|---|---|---|---|---|---|
| 50 | | | | | 55 | | | | | 60 | | | | | |

| Gln | Gly | Trp | Val | Thr | Met | Thr | Arg | Asp | Thr | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Arg | Leu | Arg | Ser | Asp | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Val | Thr | Gly | Asp | Arg | Gly | Gln | Phe | Asp | Lys | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ala | Ser |
|---|---|---|---|---|---|---|---|
| | | 115 | | | | 120 | |

```
<210> SEQ ID NO 89
<211> LENGTH: 120
<212> TYPE: PRT
<213> ORGANISM: Artificial sequence
<220> FEATURE:
<223> OTHER INFORMATION: antigene specific peptide against the human
      gene product MUC 1

<400> SEQUENCE: 89
```

| Gln | Met | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Gly | His |
|---|---|---|---|---|---|---|---|---|---|---|---|---|---|---|---|
| | | | 20 | | | | | 25 | | | | | 30 | | |

| Tyr | Met | His | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Trp | Ile | Asp | Pro | Val | Thr | Gly | Gly | Thr | Lys | Tyr | Ala | Gln | Asn | Phe |
|---|---|---|---|---|---|---|---|---|---|---|---|---|---|---|---|
| 50 | | | | | 55 | | | | | 60 | | | | | |

| Gln | Gly | Trp | Val | Thr | Met | Thr | Arg | Asp | Thr | Ser | Ile | Arg | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Arg | Leu | Arg | Ser | Asp | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Val | Thr | Gly | Asp | Arg | Gly | Gln | Phe | Asp | Lys | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ala | Ser |
|---|---|---|---|---|---|---|---|
| | | 115 | | | | 120 | |

```
<210> SEQ ID NO 90
<211> LENGTH: 120
<212> TYPE: PRT
<213> ORGANISM: Artificial sequence
<220> FEATURE:
<223> OTHER INFORMATION: antigene specific peptide against the human
      gene product MUC 1

<400> SEQUENCE: 90
```

```
Arg Met Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ala Gly His
            20                  25                  30

Tyr Met His Trp Val Arg Gln Ala Pro Gly Arg Gly Leu Glu Trp Met
        35                  40                  45

Gly Trp Ile Asp Pro Val Thr Gly Gly Thr Lys Tyr Ala Gln Asn Phe
50                  55                  60

Gln Gly Trp Val Thr Met Thr Arg Asp Thr Ser Ile Arg Thr Ala Tyr
65                  70                  75                  80

Met Glu Leu Ser Arg Leu Arg Ser Asp Asp Thr Ala Met Tyr Tyr Cys
            85                  90                  95

Ala Arg Glu Val Thr Gly Asp Arg Gly Gln Phe Asp Lys Trp Gly Gln
        100                 105                 110

Gly Thr Leu Val Thr Val Ala Ser
        115                 120
```

<210> SEQ ID NO 91
<211> LENGTH: 107
<212> TYPE: PRT
<213> ORGANISM: Artificial sequence
<220> FEATURE:
<223> OTHER INFORMATION: antigene specific peptide against the human
      gene product MUC 1

<400> SEQUENCE: 91

```
Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Ala Leu Val Ile Tyr
        35                  40                  45

Tyr Gly Ser Asn Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Trp
            85                  90                  95

Val Phe Gly Gly Gly Thr Lys Leu Thr Val Leu
        100                 105
```

<210> SEQ ID NO 92
<211> LENGTH: 107
<212> TYPE: PRT
<213> ORGANISM: Artificial sequence
<220> FEATURE:
<223> OTHER INFORMATION: antigene specific peptide against the human
      gene product MUC 1

<400> SEQUENCE: 92

```
Gln Ser Val Leu Thr Gln Pro Pro Ser Val Ser Met Ala Pro Gly Glu
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Asn Asp Ser Asp Arg Pro Ser Gly Ile Pro Glu Arg Phe Ser Gly Ser
50                  55                  60
```

```
Asn Ser Gly Lys Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ile Asp Trp
                 85                  90                  95

Val Phe Gly Gly Gly Thr Lys Leu Thr Val Leu
                100                 105
```

<210> SEQ ID NO 93
<211> LENGTH: 107
<212> TYPE: PRT
<213> ORGANISM: Artificial sequence
<220> FEATURE:
<223> OTHER INFORMATION: antigene specific peptide against the human
      gene product MUC 1

<400> SEQUENCE: 93

```
Gln Ser Val Leu Thr Gln Pro Pro Ser Val Ser Val Pro Gly Lys
 1               5                  10                  15

Thr Ala Arg Ile Ile Cys Gly Gly Asn Asn Ile Gly Ser Lys Ser Val
                 20                  25                  30

His Trp Tyr Gln Gln Lys Pro Gly Gln Ala Pro Val Leu Val Ile Tyr
             35                  40                  45

Asn Asn Ser Asp Arg Pro Ser Gly Ile Pro Glu Arg Phe Ser Gly Ser
 50                  55                  60

Asn Ser Gly Asn Met Ala Thr Leu Thr Ile Ser Arg Val Glu Ala Gly
 65                  70                  75                  80

Asp Glu Ser Asp Tyr Tyr Cys Gln Val Trp Asp Ser Ser Ser Asp Trp
                 85                  90                  95

Val Phe Gly Gly Gly Thr Arg Leu Thr Ile Leu
                100                 105
```

<210> SEQ ID NO 94
<211> LENGTH: 107
<212> TYPE: PRT
<213> ORGANISM: Artificial sequence
<220> FEATURE:
<223> OTHER INFORMATION: antigene specific peptide against the human
      gene product MUC 1

<400> SEQUENCE: 94

```
Gln Ser Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Ile Tyr
             35                  40                  45

Tyr Gly Ser Asp Arg Pro Ser Gly Ile Pro Glu Arg Phe Ser Gly Ser
 50                  55                  60

Asn Thr Gly Asn Met Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp Trp
                 85                  90                  95

Val Phe Gly Gly Gly Thr Lys Leu Thr Val Leu
                100                 105
```

<210> SEQ ID NO 95
<211> LENGTH: 107
<212> TYPE: PRT
<213> ORGANISM: Artificial sequence
<220> FEATURE:

<223> OTHER INFORMATION: antigene specific peptide against the human
      gene product MUC 1

<400> SEQUENCE: 95

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Ala Leu Val Ile Tyr
        35                  40                  45

Tyr Gly Ser Tyr Arg Pro Ser Gly Ile Pro Glu Arg Phe Ser Gly Ser
    50                  55                  60

Asn Tyr Gly Asn Thr Ala Thr Leu Thr Ile Arg Arg Val Glu Ala Gly
65                  70                  75                  80

Asp Glu Ala Asp Tyr Tyr Cys Gln Val Trp Asp Ser Ser Ser Asp Trp
                85                  90                  95

Val Phe Gly Gly Gly Thr Lys Leu Thr Val Leu
            100                 105

<210> SEQ ID NO 96
<211> LENGTH: 107
<212> TYPE: PRT
<213> ORGANISM: Artificial sequence
<220> FEATURE:
<223> OTHER INFORMATION: antigene specific peptide against the human
      gene product MUC 1

<400> SEQUENCE: 96

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Gly Ser Asp Arg Ser Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Trp
                85                  90                  95

Val Phe Gly Gly Gly Thr Lys Leu Thr Val Leu
            100                 105

<210> SEQ ID NO 97
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 97

Ser Ser Thr Lys Gly Pro Ser Val Lys Leu
1               5                   10

<210> SEQ ID NO 98
<211> LENGTH: 10
<212> TYPE: PRT
<213> ORGANISM: Artificial sequence
<220> FEATURE:
<223> OTHER INFORMATION: antigene specific peptide against the human gene product MUC 1

<400> SEQUENCE: 98

Ala Ser Thr Lys Gly Pro Ser Ala Lys Leu
1               5                   10

<210> SEQ ID NO 99
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 99

Ala Ser Thr Lys Gly Pro Ser Val Lys Leu
1               5                   10

<210> SEQ ID NO 100
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 100

Ala Ser Thr Lys Gly Pro Ser Val Lys Leu
1               5                   10

<210> SEQ ID NO 101
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 101

Ala Ser Thr Lys Gly Pro Ser Val Lys Leu
1               5                   10

<210> SEQ ID NO 102
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 102

Ala Ser Thr Lys Gly Pro Ser Val Lys Leu
1               5                   10

<210> SEQ ID NO 103
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 103

Glu Glu Gly Glu Phe Ser Glu Ala Arg Val
1               5                   10

<210> SEQ ID NO 104

<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 104

Glu Glu Gly Glu Phe Ser Glu Ala Arg Val
1               5                   10

<210> SEQ ID NO 105
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 105

Glu Glu Gly Glu Phe Ser Glu Ala Arg Val
1               5                   10

<210> SEQ ID NO 106
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 106

Glu Glu Gly Glu Phe Ser Glu Ala Arg Val
1               5                   10

<210> SEQ ID NO 107
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 107

Glu Glu Gly Glu Phe Ser Glu Ala Arg Val
1               5                   10

<210> SEQ ID NO 108
<211> LENGTH: 10
<212> TYPE: PRT
<213> ORGANISM: Artificial sequence
<220> FEATURE:
<223> OTHER INFORMATION: antigene specific peptide against the human
      gene product MUC 1

<400> SEQUENCE: 108

Glu Glu Gly Lys Phe Leu Glu Ala His Val
1               5                   10

<210> SEQ ID NO 109
<211> LENGTH: 15
<212> TYPE: PRT
<213> ORGANISM: Artificial sequence
<220> FEATURE:
<223> OTHER INFORMATION: antigene specific peptide against the human
      gene product MUC 1

<400> SEQUENCE: 109

Gly Gln Pro Lys Ala Ala Pro Ser Val Thr Leu Phe Pro Ser Ser
1               5                   10                  15

<210> SEQ ID NO 110
<211> LENGTH: 15
<212> TYPE: PRT
<213> ORGANISM: Artificial sequence
<220> FEATURE:
<223> OTHER INFORMATION: antigene specific peptide against the human
      gene product MUC 1

<400> SEQUENCE: 110

Gly Gln Pro Lys Ala Ala Pro Ser Val Thr Leu Phe Pro Pro Ser
1               5                   10                  15

<210> SEQ ID NO 111
<211> LENGTH: 15
<212> TYPE: PRT
<213> ORGANISM: Artificial sequence
<220> FEATURE:
<223> OTHER INFORMATION: antigene specific peptide against the human
      gene product MUC 1

<400> SEQUENCE: 111

Gly Gln Ser Lys Ala Ala Pro Ser Val Thr Leu Phe Pro Pro Ser
1               5                   10                  15

<210> SEQ ID NO 112
<211> LENGTH: 15
<212> TYPE: PRT
<213> ORGANISM: Artificial sequence
<220> FEATURE:
<223> OTHER INFORMATION: antigene specific peptide against the human
      gene product MUC 1

<400> SEQUENCE: 112

Gly Gln Pro Lys Ala Ala Pro Ser Val Thr Leu Phe Pro Pro Ser
1               5                   10                  15

<210> SEQ ID NO 113
<211> LENGTH: 15
<212> TYPE: PRT
<213> ORGANISM: Artificial sequence
<220> FEATURE:
<223> OTHER INFORMATION: antigene specific peptide against the human
      gene product MUC 1

<400> SEQUENCE: 113

Gly Gln Pro Lys Ala Ala Pro Ser Val Thr Leu Phe Pro Pro Ser
1               5                   10                  15

<210> SEQ ID NO 114
<211> LENGTH: 15
<212> TYPE: PRT
<213> ORGANISM: Artificial sequence
<220> FEATURE:
<223> OTHER INFORMATION: antigene specific peptide against the human
      gene product MUC 1

<400> SEQUENCE: 114

Gly Gln Pro Lys Ala Ala Pro Ser Val Thr Leu Phe Pro Pro Ser
1               5                   10                  15

<210> SEQ ID NO 115
<211> LENGTH: 16
<212> TYPE: PRT
<213> ORGANISM: Artificial sequence
<220> FEATURE:

<223> OTHER INFORMATION: antigene specific peptide against the human
      gene product MUC 1

<400> SEQUENCE: 115

Ala Pro Asp Thr Arg Pro Ala Pro Gly Ser Thr Ala Pro Pro Ala Cys
1               5                   10                  15

<210> SEQ ID NO 116
<211> LENGTH: 32
<212> TYPE: PRT
<213> ORGANISM: Artificial sequence
<220> FEATURE:
<223> OTHER INFORMATION: antigene specific peptide against the human
      gene product MUC 1

<400> SEQUENCE: 116

Ala Pro Asp Thr Arg Pro Ala Pro Gly Ser Thr Ala Pro Pro Ala His
1               5                   10                  15

Gly Val Thr Ser Ala Pro Asp Thr Arg Pro Ala Pro Gly Ser Thr Ala
            20                  25                  30

<210> SEQ ID NO 117
<211> LENGTH: 33
<212> TYPE: PRT
<213> ORGANISM: Artificial sequence
<220> FEATURE:
<223> OTHER INFORMATION: biotinylated beta-Alanin

<400> SEQUENCE: 117

Ala Ala Pro Asp Thr Arg Pro Ala Pro Gly Ser Thr Ala Pro Pro Ala
1               5                   10                  15

His Gly Val Thr Ser Ala Pro Asp Thr Arg Pro Ala Pro Gly Ser Thr
            20                  25                  30

Ala

<210> SEQ ID NO 118
<211> LENGTH: 33
<212> TYPE: PRT
<213> ORGANISM: Artificial sequence
<220> FEATURE:
<223> OTHER INFORMATION: antigene specific peptide against the human
      gene product MUC 1

<400> SEQUENCE: 118

Ala Pro Asp Thr Arg Pro Ala Pro Gly Ser Thr Ala Pro Pro Ala His
1               5                   10                  15

Gly Val Thr Ser Ala Pro Asp Thr Arg Pro Ala Pro Gly Ser Thr Ala
            20                  25                  30

Cys

<210> SEQ ID NO 119
<211> LENGTH: 21
<212> TYPE: DNA
<213> ORGANISM: Artificial sequence
<220> FEATURE:
<223> OTHER INFORMATION: Primer forward 5for amplification of lambda-CL

<400> SEQUENCE: 119
tggctgcacc aagtgtcact c                                           21

<210> SEQ ID NO 120
<211> LENGTH: 22
<212> TYPE: DNA
<213> ORGANISM: Artificial sequence

```
<220> FEATURE:
<223> OTHER INFORMATION: Primer revers 5for amplification of lambda-CL

<400> SEQUENCE: 120
ccgggatcct ctctagagtt ta                                              22

<210> SEQ ID NO 121
<211> LENGTH: 23
<212> TYPE: DNA
<213> ORGANISM: Artificial sequence
<220> FEATURE:
<223> OTHER INFORMATION: Primer revers seq 5for sequencing of lambda-CL

<400> SEQUENCE: 121
gggaggggca aacaacagat ggc                                             23

<210> SEQ ID NO 122
<211> LENGTH: 262
<212> TYPE: PRT
<213> ORGANISM: Artificial sequence
<220> FEATURE:
<223> OTHER INFORMATION: antigene specific peptide against the human
      gene product MUC 1

<400> SEQUENCE: 122
```

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Asp Pro Val Thr Gly Gly Thr Lys Tyr Ala Gln Asn Phe
    50                  55                  60

Gln Gly Trp Val Thr Met Thr Arg Asp Thr Ser Ile Arg Thr Ala Tyr
65                  70                  75                  80

Met Glu Leu Ser Arg Leu Arg Ser Asp Asp Thr Ala Met Tyr Tyr Cys
                85                  90                  95

Ala Arg Glu Val Thr Gly Asp Arg Gly Gln Phe Asp Lys Trp Gly Gln
            100                 105                 110

Gly Thr Leu Val Thr Val Ala Ser Ala Ser Thr Lys Gly Pro Ser Val
        115                 120                 125

Lys Leu Glu Glu Gly Glu Phe Ser Glu Ala Arg Val Gln Ser Val Leu
    130                 135                 140

Thr Gln Pro Pro Ser Val Ser Val Ala Pro Gly Lys Thr Ala Arg Ile
145                 150                 155                 160

Thr Cys Gly Gly Asn Asn Ile Gly Ser Lys Ser Val His Trp Tyr Gln
                165                 170                 175

Gln Lys Pro Gly Gln Ala Pro Ala Leu Val Ile Tyr Tyr Gly Ser Tyr
            180                 185                 190

Arg Pro Ser Gly Ile Pro Glu Arg Phe Ser Gly Ser Asn Tyr Gly Asn
        195                 200                 205

Thr Ala Thr Leu Thr Ile Arg Arg Val Glu Ala Gly Asp Glu Ala Asp
    210                 215                 220

Tyr Tyr Cys Gln Val Trp Asp Ser Ser Asp Trp Val Phe Gly Gly
225                 230                 235                 240

Gly Thr Lys Leu Thr Val Leu Gly Gln Pro Lys Ala Ala Pro Ser Val
                245                 250                 255

Thr Leu Phe Pro Pro Ser

<210> SEQ ID NO 123
<211> LENGTH: 262
<212> TYPE: PRT
<213> ORGANISM: Artificial sequence
<220> FEATURE:
<223> OTHER INFORMATION: antigene specific peptide against the human gene product MUC 1

<400> SEQUENCE: 123

Gln Met Gln Leu Val Gln Ser Glu Ala Glu Leu Lys Lys Pro Gly Ala
1               5                   10                  15

Ser Val Lys Val Ser Cys Lys Ala Ser Gly Tyr Ser Phe Thr Gly His
            20                  25                  30

Tyr Met His Trp Val Arg Gln Ala Pro Gly Gln Gly Leu Glu Trp Met
        35                  40                  45

Gly Trp Ile Asp Pro Val Thr Gly Thr Lys Tyr Ala Gln Asn Phe
    50                  55                  60

Gln Gly Trp Val Thr Met Thr Arg Asp Thr Ser Ile Arg Thr Ala Tyr
65                  70                  75                  80

Leu Glu Leu Ser Arg Leu Arg Ser Asp Asp Thr Ala Met Tyr Tyr Cys
                85                  90                  95

Ala Arg Glu Val Thr Gly Asp Arg Gly Gln Phe Asp Lys Trp Gly Gln
            100                 105                 110

Gly Thr Leu Val Thr Val Ala Ser Ser Thr Lys Gly Pro Ser Val
        115                 120                 125

Lys Leu Glu Glu Gly Glu Phe Ser Glu Ala Arg Val Gln Ser Val Leu
130                 135                 140

Thr Gln Pro Pro Ser Val Ser Val Ala Pro Gly Lys Thr Ala Arg Ile
145                 150                 155                 160

Thr Cys Gly Gly Asn Asn Ile Gly Ser Lys Ser Val His Trp Tyr Gln
                165                 170                 175

Gln Lys Pro Gly Gln Ala Pro Ala Leu Val Ile Tyr Tyr Gly Ser Asn
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Arg Val Glu Ala Gly Asp Glu Ala Asp
    210                 215                 220

Tyr Tyr Cys Gln Val Trp Asp Ser Ser Asp Trp Val Phe Gly Gly
225                 230                 235                 240

Gly Thr Lys Leu Thr Val Leu Gly Gln Pro Lys Ala Ala Pro Ser Val
                245                 250                 255

Thr Leu Phe Pro Ser Ser
            260

<210> SEQ ID NO 124
<211> LENGTH: 262
<212> TYPE: PRT
<213> ORGANISM: Artificial sequence
<220> FEATURE:
<223> OTHER INFORMATION: antigene specific peptide against the human gene product MUC 1

<400> SEQUENCE: 124

Arg Met Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ala Gly His

```
                20                  25                  30
Tyr Met His Trp Val Arg Gln Ala Pro Gly Arg Gly Leu Glu Trp Met
            35                  40                  45
Gly Trp Ile Asp Pro Val Thr Gly Gly Thr Lys Tyr Ala Gln Asn Phe
         50                  55                  60
Gln Gly Trp Val Thr Met Thr Arg Asp Thr Ser Ile Arg Thr Ala Tyr
 65                  70                  75                  80
Met Glu Leu Ser Arg Leu Arg Ser Asp Asp Thr Ala Met Tyr Tyr Cys
                 85                  90                  95
Ala Arg Glu Val Thr Gly Asp Arg Gly Gln Phe Asp Lys Trp Gly Gln
            100                 105                 110
Gly Thr Leu Val Thr Val Ala Ser Ala Ser Thr Lys Gly Pro Ser Val
            115                 120                 125
Lys Leu Glu Glu Gly Lys Phe Leu Glu Ala His Val Gln Ser Val Leu
            130                 135                 140
Thr Gln Pro Pro Ser Val Ser Val Ala Pro Gly Lys Thr Ala Arg Ile
145                 150                 155                 160
Thr Cys Gly Gly Asn Asn Ile Gly Ser Lys Ser Val His Trp Tyr Gln
                165                 170                 175
Gln Lys Pro Gly Gln Ala Pro Val Leu Val Ile Tyr Tyr Gly Ser Asp
            180                 185                 190
Arg Ser Ser Gly Ile Pro Glu Arg Phe Ser Gly Ser Asn Ser Gly Asn
            195                 200                 205
Thr Ala Thr Leu Thr Ile Ser Arg Val Glu Ala Gly Asp Glu Ala Asp
            210                 215                 220
Tyr Tyr Cys Gln Val Trp Asp Ser Ser Asp Trp Val Phe Gly Gly
225                 230                 235                 240
Gly Thr Lys Leu Thr Val Leu Gly Gln Pro Lys Ala Ala Pro Ser Val
                245                 250                 255
Thr Leu Phe Pro Pro Ser
            260

<210> SEQ ID NO 125
<211> LENGTH: 232
<212> TYPE: PRT
<213> ORGANISM: Artificial sequence
<220> FEATURE:
<223> OTHER INFORMATION: antigene specific peptide against the human
      gene product MUC 1

<400> SEQUENCE: 125

Met Ala Trp Thr Val Leu Leu Gly Leu Leu Ser His Cys Thr Gly
 1               5                  10                  15
Ser Val Thr Gln Ser Val Leu Thr Gln Pro Pro Ser Val Ser Val Ala
            20                  25                  30
Pro Gly Lys Thr Ala Arg Ile Thr Cys Gly Gly Asn Asn Ile Gly Ser
            35                  40                  45
Lys Ser Val His Trp Tyr Gln Gln Lys Pro Gly Gln Ala Pro Ala Leu
         50                  55                  60
Val Ile Tyr Tyr Gly Ser Tyr Arg Pro Ser Gly Ile Pro Glu Arg Phe
 65                  70                  75                  80
Ser Gly Ser Asn Tyr Gly Asn Thr Ala Thr Leu Thr Ile Arg Arg Val
                 85                  90                  95
Glu Ala Gly Asp Glu Ala Asp Tyr Tyr Cys Gln Val Trp Asp Ser Ser
            100                 105                 110
```

Ser Asp Trp Val Phe Gly Gly Thr Lys Leu Thr Val Leu Gly Gln
115                 120                 125

Pro Lys Ala Ala Pro Ser Val Thr Leu Phe Pro Pro Ser Ser Glu Glu
130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
                180                 185                 190

Ala Ala Ser Ser Tyr Leu Ser Leu Thr Pro Glu Gln Trp Lys Ser His
                195                 200                 205

Arg Ser Tyr Ser Cys Gln Val Thr His Glu Gly Ser Thr Val Glu Lys
210                 215                 220

Thr Val Ala Pro Thr Glu Cys Ser
225                 230

<210> SEQ ID NO 126
<211> LENGTH: 232
<212> TYPE: PRT
<213> ORGANISM: Artificial sequence
<220> FEATURE:
<223> OTHER INFORMATION: antigene specific peptide against the human
      gene product MUC 1

<400> SEQUENCE: 126

Met Ala Trp Thr Val Leu Leu Gly Leu Leu Ser His Cys Thr Gly
1               5                   10                  15

Ser Val Thr Gln Ser Val Leu Thr Gln Pro Pro Ser Val Ser Val Ala
                20                  25                  30

Pro Gly Lys Thr Ala Arg Ile Thr Cys Gly Gly Asn Asn Ile Gly Ser
                35                  40                  45

Lys Ser Val His Trp Tyr Gln Gln Lys Pro Gly Gln Ala Pro Val Leu
50                  55                  60

Val Ile Tyr Tyr Gly Ser Asp Arg Ser Ser Gly Ile Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Ser Ser
                100                 105                 110

Ser Asp Trp Val Phe Gly Gly Thr Lys Leu Thr Val Leu Gly Gln
                115                 120                 125

Pro Lys Ala Ala Pro Ser Val Thr Leu Phe Pro Pro Ser Ser Glu Glu
130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
                180                 185                 190

Ala Ala Ser Ser Tyr Leu Ser Leu Thr Pro Glu Gln Trp Lys Ser His
                195                 200                 205

Arg Ser Tyr Ser Cys Gln Val Thr His Glu Gly Ser Thr Val Glu Lys
210                 215                 220

Thr Val Ala Pro Thr Glu Cys Ser
225                 230

```
<210> SEQ ID NO 127
<211> LENGTH: 232
<212> TYPE: PRT
<213> ORGANISM: Artificial sequence
<220> FEATURE:
<223> OTHER INFORMATION: antigene specific peptide against the human
      gene product MUC 1

<400> SEQUENCE: 127

Met Ala Trp Thr Val Leu Leu Gly Leu Leu Ser His Cys Thr Gly
1               5                   10                  15

Ser Val Thr Gln Ser Val Leu Thr Gln Pro Pro Ser Val Ser Val Ala
                20                  25                  30

Pro Gly Lys Thr Ala Arg Ile Thr Cys Gly Gly Asn Asn Ile Gly Ser
            35                  40                  45

Lys Ser Val His Trp Tyr Gln Gln Lys Pro Gly Gln Ala Pro Ala Leu
        50                  55                  60

Val Ile Tyr Tyr Gly Ser Asn Arg Pro Ser Gly Ile Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Ser Ser
            100                 105                 110

Ser Asp Trp Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 128
<211> LENGTH: 213
<212> TYPE: PRT
<213> ORGANISM: Artificial sequence
<220> FEATURE:
<223> OTHER INFORMATION: antigene specific peptide against the human
      gene product MUC 1

<400> SEQUENCE: 128

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Ala Leu Val Ile Tyr
            35                  40                  45

Tyr Gly Ser Tyr Arg Pro Ser Gly Ile Pro Glu Arg Phe Ser Gly Ser
        50                  55                  60
```

```
Asn Tyr Gly Asn Thr Ala Thr Leu Thr Ile Arg Arg Val Glu Ala Gly
 65                  70                  75                  80

Asp Glu Ala Asp Tyr Tyr Cys Gln Val Trp Asp Ser Ser Ser Asp Trp
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 129
<211> LENGTH: 213
<212> TYPE: PRT
<213> ORGANISM: Artificial sequence
<220> FEATURE:
<223> OTHER INFORMATION: antigene specific peptide against the human
      gene product MUC 1

<400> SEQUENCE: 129

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Gly Ser Asp Arg Ser Ser Gly Ile Pro Glu Arg Phe Ser Gly Ser
    50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp Trp
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
```

```
                195                 200                 205

Pro Thr Glu Cys Ser
    210

<210> SEQ ID NO 130
<211> LENGTH: 213
<212> TYPE: PRT
<213> ORGANISM: Artificial sequence
<220> FEATURE:
<223> OTHER INFORMATION: antigene specific peptide against the human
      gene product MUC 1

<400> SEQUENCE: 130

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Ala Leu Val Ile Tyr
        35                  40                  45

Tyr Gly Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Trp
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 131
<211> LENGTH: 469
<212> TYPE: PRT
<213> ORGANISM: Artificial sequence
<220> FEATURE:
<223> OTHER INFORMATION: antigene specific peptide against the human
      gene product MUC 1

<400> SEQUENCE: 131

Met Asp Trp Thr Trp Arg Ile Leu Phe Leu Val Ala Ala Thr Gly
1               5                   10                  15

Ala His Ser Gln Met Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly His Tyr Met His Trp Val Arg Gln Ala Pro Gly Gln Gly Leu
```

```
                  50                  55                  60
Glu Trp Met Gly Trp Ile Asp Pro Val Thr Gly Thr Lys Tyr Ala
 65                  70                  75                  80

Gln Asn Phe Gln Gly Trp Val Thr Met Thr Arg Asp Thr Ser Ile Arg
                     85                  90                  95

Thr Ala Tyr Met Glu Leu Ser Arg Leu Arg Ser Asp Asp Thr Ala Met
                100                 105                 110

Tyr Tyr Cys Ala Arg Glu Val Thr Gly Asp Arg Gly Gln Phe Asp Lys
            115                 120                 125

Trp Gly Gln Gly Thr Leu Val Thr Val Ala Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465
```

<210> SEQ ID NO 132
<211> LENGTH: 469
<212> TYPE: PRT
<213> ORGANISM: Artificial sequence
<220> FEATURE:
<223> OTHER INFORMATION: antigene specific peptide against the human gene product MUC 1

<400> SEQUENCE: 132

```
Met Asp Trp Thr Trp Arg Ile Leu Phe Leu Val Ala Ala Thr Gly
1               5                   10                  15

Ala His Ser Arg Met Gln Leu Val Gln Ser Gly Ala Glu Val Lys Lys
            20                  25                  30

Pro Gly Ala Ser Val Lys Leu Ser Cys Lys Ala Ser Gly Tyr Thr Phe
        35                  40                  45

Ala Gly His Tyr Met His Trp Val Arg Gln Ala Pro Gly Arg Gly Leu
    50                  55                  60

Glu Trp Met Gly Trp Ile Asp Pro Val Thr Gly Gly Thr Lys Tyr Ala
65                  70                  75                  80

Gln Asn Phe Gln Gly Trp Val Thr Met Thr Arg Asp Thr Ser Ile Arg
                85                  90                  95

Thr Ala Tyr Met Glu Leu Ser Arg Leu Arg Ser Asp Asp Thr Ala Met
            100                 105                 110

Tyr Tyr Cys Ala Arg Glu Val Thr Gly Asp Arg Gly Gln Phe Asp Lys
        115                 120                 125

Trp Gly Gln Gly Thr Leu Val Thr Val Ala Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
```

```
                    355                 360                 365
Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 133
<211> LENGTH: 469
<212> TYPE: PRT
<213> ORGANISM: Artificial sequence
<220> FEATURE:
<223> OTHER INFORMATION: antigene specific peptide against the human
      gene product MUC 1

<400> SEQUENCE: 133

Met Asp Trp Thr Trp Arg Ile Leu Phe Leu Val Ala Ala Ala Thr Gly
1               5                   10                  15

Ala His Ser Gln Met Gln Leu Val Gln Ser Glu Ala Glu Leu Lys Lys
            20                  25                  30

Pro Gly Ala Ser Val Lys Val Ser Cys Lys Ala Ser Gly Tyr Ser Phe
        35                  40                  45

Thr Gly His Tyr Met His Trp Val Arg Gln Ala Pro Gly Gln Gly Leu
    50                  55                  60

Glu Trp Met Gly Trp Ile Asp Pro Val Thr Gly Thr Lys Tyr Ala
65              70                  75                  80

Gln Asn Phe Gln Gly Trp Val Thr Met Thr Arg Asp Thr Ser Ile Arg
            85                  90                  95

Thr Ala Tyr Leu Glu Leu Ser Arg Leu Arg Ser Asp Asp Thr Ala Met
        100                 105                 110

Tyr Tyr Cys Ala Arg Glu Val Thr Gly Asp Arg Gly Gln Phe Asp Lys
    115                 120                 125

Trp Gly Gln Gly Thr Leu Val Thr Val Ala Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240
```

-continued

```
Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 134
<211> LENGTH: 450
<212> TYPE: PRT
<213> ORGANISM: Artificial sequence
<220> FEATURE:
<223> OTHER INFORMATION: antigene specific peptide against the human
      gene product MUC 1

<400> SEQUENCE: 134

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Asp Pro Val Thr Gly Gly Thr Lys Tyr Ala Gln Asn Phe
    50                  55                  60

Gln Gly Trp Val Thr Met Thr Arg Asp Thr Ser Ile Arg Thr Ala Tyr
65                  70                  75                  80

Met Glu Leu Ser Arg Leu Arg Ser Asp Asp Thr Ala Met Tyr Tyr Cys
                85                  90                  95

Ala Arg Glu Val Thr Gly Asp Arg Gly Gln Phe Asp Lys Trp Gly Gln
            100                 105                 110

Gly Thr Leu Val Thr Val Ala Ser Ala Ser Thr Lys Gly Pro Ser Val
        115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 135
<211> LENGTH: 450
<212> TYPE: PRT
<213> ORGANISM: Artificial sequence
<220> FEATURE:
<223> OTHER INFORMATION: antigene specific peptide against the human
      gene product MUC 1

<400> SEQUENCE: 135

Arg Met Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ala Gly His
```

```
                20                  25                  30
Tyr Met His Trp Val Arg Gln Ala Pro Gly Arg Gly Leu Glu Trp Met
             35                  40                  45
Gly Trp Ile Asp Pro Val Thr Gly Thr Lys Tyr Ala Gln Asn Phe
 50                  55                  60
Gln Gly Trp Val Thr Met Thr Arg Asp Thr Ser Ile Arg Thr Ala Tyr
 65                  70                  75                  80
Met Glu Leu Ser Arg Leu Arg Ser Asp Thr Ala Met Tyr Tyr Cys
             85                  90                  95
Ala Arg Glu Val Thr Gly Asp Arg Gly Gln Phe Asp Lys Trp Gly Gln
                100                 105                 110
Gly Thr Leu Val Thr Val Ala Ser Ala Ser Thr Lys Gly Pro Ser Val
             115                 120                 125
Phe Pro Leu Ala Pro Ser Ser Lys Ser Thr Ser Gly Gly Thr Ala Ala
             130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
             195                 200                 205
Pro Ser Asn Thr Lys Val Asp Lys Lys Val Glu Pro Lys Ser Cys Asp
         210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
             275                 280                 285
Asn Ala Lys Thr Lys Pro Arg Glu Glu Gln Tyr Asn Ser Thr Tyr Arg
             290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
             340                 345                 350
Thr Leu Pro Pro Ser Arg Asp Glu Leu Thr Lys Asn Gln Val Ser Leu
             355                 360                 365
Thr Cys Leu Val Lys Gly Phe Tyr Pro Ser Asp Ile Ala Val Glu Trp
             370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
             435                 440                 445
```

Gly Lys
    450

<210> SEQ ID NO 136
<211> LENGTH: 450
<212> TYPE: PRT
<213> ORGANISM: Artificial sequence
<220> FEATURE:
<223> OTHER INFORMATION: antigene specific peptide against the human
      gene product MUC 1

<400> SEQUENCE: 136

Gln Met Gln Leu Val Gln Ser Glu Ala Glu Leu Lys Lys Pro Gly Ala
1               5                   10                  15

Ser Val Lys Val Ser Cys Lys Ala Ser Gly Tyr Ser Phe Thr Gly His
            20                  25                  30

Tyr Met His Trp Val Arg Gln Ala Pro Gly Gln Gly Leu Glu Trp Met
        35                  40                  45

Gly Trp Ile Asp Pro Val Thr Gly Gly Thr Lys Tyr Ala Gln Asn Phe
    50                  55                  60

Gln Gly Trp Val Thr Met Thr Arg Asp Thr Ser Ile Arg Thr Ala Tyr
65                  70                  75                  80

Leu Glu Leu Ser Arg Leu Arg Ser Asp Asp Thr Ala Met Tyr Tyr Cys
                85                  90                  95

Ala Arg Glu Val Thr Gly Asp Arg Gly Gln Phe Asp Lys Trp Gly Gln
            100                 105                 110

Gly Thr Leu Val Thr Val Ala Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
                    340                 345                 350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 137
<211> LENGTH: 4
<212> TYPE: PRT
<213> ORGANISM: Artificial sequence
<220> FEATURE:
<223> OTHER INFORMATION: MUC 1 mucin core region

<400> SEQUENCE: 137

Arg Pro Ala Pro
1

<210> SEQ ID NO 138
<211> LENGTH: 20
<212> TYPE: PRT
<213> ORGANISM: Artificial sequence
<220> FEATURE:
<223> OTHER INFORMATION: repeating unit in MUC 1 extracellular domain

<400> SEQUENCE: 138

Thr Ser Ala Pro Asp Thr Arg Pro Ala Pro Gly Ser Thr Ala Pro Pro
1               5                   10                  15

Ala His Gly Val
            20
```

RECOMBINANT ANTI-MUC1 ANTIBODIES

The present invention relates to antibodies having a high specificity and high affinity towards the human gene product MUC1, which in specific variants is associated with neoplastic cells, i.e. tumor tissue, to the use of the antibodies for medical purposes, i.e. for tumor treatment, and for analytical purposes, e.g. for tumor diagnosis. Further, the invention relates to compositions comprising the antibodies, e.g. for use in the analytical processes and analyses, to pharmaceutical compositions comprising the antibodies, and to use of the antibodies in the manufacture of pharmaceutical compositions for tumor treatment or for diagnostic purposes.

Herein, the term antibody is used interchangeably with binding peptide or antigen specific peptide, as the invention provides amino acid sequences as well as nucleic acid sequences encoding the amino acid sequences, which amino acid sequences comprise at least two regions having affinity for one another for association, the amino acid sequence regions forming a paratope with high specificity and high affinity to the tumor associated variant of the MUC1 antigen. The antibodies of the invention can be single chain peptides or one or more associated peptides, forming a paratope with high specificity to an epitope in the tumor-associated variant of the MUC1 protein.

Antibodies of the invention comprise at least two binding peptides forming a paratope with high specificity for MUC1, which binding peptides can be comprised in natural or synthetic peptides, in one or more associated polypeptide chains, e.g. in a single chain variable fragments (scFv), single chain antibody fragments (scFab), in polypeptides comprising one or more natural or synthetic antibody domains, e.g. CH1, CH2, CH3, scFv-Fc and other synthetic antibody fusion proteins, or synthetic association domains, like knob-in-hole providing peptide sections, leucin zipper sections, amphipathic helices, a biotin acceptor domain and an associable avidin or streptavidin domain, each association domain independently contained in a single chain polypeptide or in two or more associated polypeptide chains. Optionally, the antibodies of the invention can comprise at least one effector domain, e.g. selected from a toxin, a radionuclide, a toxic enzyme, a cytotoxic compound, and/or a detectable label, for antigen-specific delivery to tumor cells. Preferably, an IgG, IgA, IgD, or IgE is provided containing the binding peptide of the invention, most preferably the light chain domains of the binding peptide as part of the light chain, and the heavy chain domains of the binding peptide as part of the heavy chain. In embodiments of Ig containing the binding peptides of the invention, the Fc-portion serves as an effector domain, e.g. for use of the Ig in the production of pharmaceutical compositions for medical use.

STATE OF THE ART

It is known that tumor cells can have a different expression pattern of membrane-bound proteins having extracellular domains, which differences can be used for the specific detection of tumor cells, including the specific delivery of detectable labels or effector compounds to tumor cells, using the specific affinity of antibodies or antibody domains. For example, EP 1366161 B1 describes a polypeptide sequence which is an extracellular domain of a membrane-bound peptide, the peptide participating in the regulation of the immune response.

EP 0941344 B1 describes a humanized antibody specific for the cellular receptor CD11a, the antibody being useful for masking the cell surface receptor.

U.S. Pat. No. 7,368,250 B2 claims a method for diagnosis of cancer cells by analysing the relative expression level of tumor associated epitopes using epitope specific antibodies.

EP 1189931 D1 describes amino acid sections for antibodies that form a specific paratope having affinity to the tumor associated cell surface bound receptor protein p185HER2. The amino acid sequence having specificity for the tumor associated variant of the receptor is preferably contained in a peptide chain forming an immunoglobulin domain, preferably further associated with a multimerisation domain for increasing the avidity.

Zotter et al. (Cancer Reviews, vol. 11/12, 55-101 (1988) describe epithelial MUC1 (also termed CD227, CA-15-3 and PEM) as a transmembrane protein, the O-glycosylation of which is significantly altered in tumor cells. MUC1 in its extracellular domain comprises about 20 to 120 repeating units (variable number of tandem repeats, VNTR). One repeating unit has the following amino acid sequence: TSAPDTRPAPGSTAPPAHGV (SEQ ID NO:138), wherein the potential O-glycosylated amino acids are underlined. Zotter et al. and Hilkens et al. (Cancer Res. 46 (5), 2582-2587 (1986)) found that MUC1 is over-expressed in tumor cells and presented over the entire cell surface, whereas in non-neoplastic epitheial cells, MUC1 is expressed only apically. Danielczyk et al. (Cancer Immunol. Immunother. 55 (11), 1337-1347 (2006) describe that due to the presentation of MUC 1 also on the non-apical cell surface, MUC1 is accessible by systemically administered antibody, and describe the monoclonal antibody PankoMab having specificity for the tumor variant of MUC1. Murine antibody PankoMab is directed against a glycosylation-dependent epitope of tumor associated MUC1 with an apparent affinity of up to $9 \times 10^{-10}$ M for tumor specific MUC1 (Danielczyk et al., Cancer Immunol. Immunother., 1337-1347 (2006)).

Henderikx et al. (Cancer Res. 58 (19) 4324-4332 (1989)) describe single chain Fv antibodies to MUC1 core peptide with an apparent affinity of $8.7 \times 10^{-9}$ (monovalent affinity $1.4 \times 10^{-7}$ M) for synthetic MUC1 peptide (Henderickx et al., Am. J. Path. (5), 1597-1608 (2002)). For optimization and isolation of antibody sections participating in the formation of the paratope, affinity selection using phage display libraries was employed.

From Toleikis (doctoral thesis, Universität Heidelberg (2004)) a recombinant single chain Fv antibody fragment is known that was isolated from an antibody gene library generated from DNA isolated from patients that were immunized with synthetic MUC1 peptide administered for therapeutical purposes for treatment of metastasing breast cancer. For enriching anti-MUC1 antibodies, a phage display library was generated from the antibody gene library, an affinity selection was performed, alternatingly on synthetic MUC1 peptide and on natural MUC1 isolated from T47D tumor cells. The isolated antibody fragment could be shown by surface plasmon resonance to have an affinity of $2.3 \times 10^{-7}$ M to the glycopeptide, and in immune stains to react specifically with more than 80% of tissue samples of breast cancer (Toleikis et al., (IBC's 17th Annual International Conference Antibody Engineering, December 2006, San Diego, poster presentation).

OBJECTS OF THE INVENTION

It is an object of the present invention to provide an alternative binding protein, preferably suitable for being comprised in a synthetic or natural antibody, having an improved specificity and/or an improved affinity to a tumor associated extracellular antigen, preferably to the tumor-specific glycosylation variant of MUC1. Preferably, the binding protein and the antibody comprising said binding protein are suitable for production in mammalian cell culture, or by expression in a micro-organism, e.g. yeast or bacteria. Preferably, an antibody comprising the binding peptide of the invention has a high long-term stability in pharmaceutical formulations, e.g. at long time incubation at 37° C. in solution, in combination with stable binding to the antigen in an aqueous medium, e.g. having a reduced propensity for aggregation in aqueous solution. The desired high affinity, high stability, reduced rate of aggregation preferably is in aqueous compositions for use in diagnostics, in pharmaceutical formulations suitable for administration to a patient, as well as during presence in the body of a patient, e.g. in body fluids such as serum.

GENERAL DESCRIPTION OF THE INVENTION

The invention achieves the above-mentioned objects by providing binding peptides and antibodies comprising the binding peptides comprised of an antibody heavy chain variable region comprising the amino acid sequence of CDR1 selected from SEQ ID NO: 1 to SEQ ID NO: 6, and one of the amino acid sequences of CDR2 selected from SEQ ID NO: 7 to Seq.-ID No. 12, and/or the amino acid sequence of CDR3 selected from SEQ ID NO: 13 to Seq.-ID No. 18 and/or a light chain variable region comprising the amino acid sequence of CDR1 selected from SEQ ID NO: 19 to Seq.-ID No. 24 and the amino acid sequence of CDR2 selected from SEQ ID NO: 25 to Seq.-ID No. 30, and/or the amino acid sequence of CDR3 selected from SEQ ID NO: 31 to Seq.-ID No. 36. Preferably, the complementary determining regions (CDR) are arranged, from N-terminus to C-terminus, as CDR1-CDR2-CDR3, with framework regions interspersed between the CDRs, and preferably with CDRs all of heavy chain variable regions with heavy chain framework regions, or framework regions of light chain variable regions for light chain CDRs, respectively.

More preferably, the CDRs are arranged with interspersed amino acid sequences as FR1-CDR1-FR2-CDR2-FR3-CDR3-FR4, wherein independently, each framework region (FR) can be heavy chain or light chain variable region, but preferably each framework region is of heavy chain variable region for CDRs of heavy chain variable region, whereas FRs for light chain variable region preferably are arranged adjacent light chain variable region CDRs.

More preferably, each binding peptide consists of FR1-CDR1-FR2-CDR2-FR3-CDR3-FR4, all of heavy chain variable region or of light chain variable region only, most preferably with the FRs and CDRs originating from the heavy chain variable region and the light chain variable region of a single exemplary antibody, respectively.

Generally, all arrangements of amino acid regions, of peptides, or amino acid sequences are noted from N-terminus to C-terminus. Further generally, each heavy chain variable fragment can be associated with each light chain variable fragment, e.g. a heavy chain variable fragment from one preferred binding peptide (e.g. one of Seq.-ID Nos. 85 to 90) can be associated in a single chain peptide (e.g. as an scFv) or as one of two or more associated peptide chains (e.g. as an IgG) with a light chain variable fragment of another binding peptide (e.g. one of Seq.-ID Nos. 91 to 96), preferably of the same binding peptide.

Preferably, the binding peptides and the antibodies comprising the binding peptide have high specific affinity for an epitope having the amino acid sequence RPAP. Preferably, the binding affinity is provided by a light chain variable fragment in association with a heavy chain variable fragment consisting of FR1-CDR1-FR2-CDR2-FR3-CDR3-FR4 of light chain and heavy chain antibody regions, respectively, most preferably the light chain variable fragment having the antigen binding affinity of an amino acid sequence of one of SEQ ID NO: 91, SEQ ID NO: 92, SEQ ID NO: 93, SEQ ID NO: 94, SEQ ID NO: 95, and SEQ ID NO: 96, and the heavy chain variable fragment having the antigen binding affinity of an amino acid sequence of one of SEQ ID NO: 85, SEQ ID NO: 86, SEQ ID NO: 87, SEQ ID NO: 88, SEQ ID NO: 89, and SEQ ID NO: 90.

Preferably, the binding peptides of the invention comprise heavy chain variable fragment framework regions comprising the amino acid sequence of FR1, e.g. selected from SEQ ID NO: 37 to SEQ ID NO: 42, and of FR2, e.g. selected from SEQ ID NO: 43 to SEQ ID NO: 48, and/or the amino acid sequence of FR3, e.g. selected from SEQ ID NO: 49 to SEQ ID NO: 54, and/or the amino acid sequence of FR4, e.g. selected from SEQ ID NO: 55 to SEQ ID NO: 60, especially for heavy chain CDRs.

Preferably, the binding peptides of the invention comprise light chain variable fragment framework regions comprising the amino acid sequence of FR1, e.g. selected from SEQ ID NO: 61 to SEQ ID NO: 66, and of FR2, e.g. selected from SEQ ID NO: 67 to SEQ ID NO: 72, and/or the amino acid sequence of FR3, e.g. selected from SEQ ID NO: 73 to SEQ ID NO: 78, and/or the amino acid sequence of FR4, e.g. selected from SEQ ID NO: 79 to SEQ ID NO: 84, especially for light chain CDRs.

In one embodiment, the binding peptides of the invention consists of a single chain variable fragment of a heavy chain (VH) of FR1-CDR1-FR2-CDR2-FR3-CDR3-FR4-CH1-linker—variable light chain (VL) of FR1-CDR1-FR2-CDR2-FR3-CDR3-FR4-CL, optionally being linked at its N-terminus and/or C-terminus to an effector component.

Preferably, the heavy chain variable region has the affinity of at least one of SEQ ID NO: 85, SEQ ID NO: 86, SEQ ID NO: 87; SEQ ID NO: 88, SEQ ID NO: 89, and SEQ ID NO: 90, and the light chain variable region has the affinity of SEQ ID NO: 91, SEQ ID NO: 92, SEQ ID NO: 93, SEQ ID NO: 94, SEQ ID NO: 95, and SEQ ID NO: 96.

The N-terminal position of the CH1 domain preferably has the conformation of one of the amino acid sequences SEQ ID NO: 97 to SEQ ID NO: 102 which are C-truncated sections of natural CH1 domains, whereas the N-terminal position of the CL domain preferably has the amino acid sequence of one of SEQ ID NO: 109 to SEQ ID NO: 114 which are C-terminally truncated sections of natural CL domains. Preferably, the linker arranged without interspersing amino acids between the C-terminus of the CH1 domain and the N-terminus of the VL domain has the conformation of one of the amino acid sequences SEQ ID NO: 103 to SEQ ID NO: 108.

Generally, the conformation of single amino acid sections comprised in the binding peptides of the invention are obtainable by the respective amino acid sequences given, including amino acid sequences containing one, two, three, four or five mutations, e.g. substitutions, insertions and/or exchanges of single amino acids in each respective amino acid section, e.g. in each FR, each CDR, each constant domain and each linker, while essentially maintaining the characteristic properties of the resulting natural or synthetic antibody, especially its affinity and specificity to an epitope, its stability, produceability in micro-organisms, and its reduced rate of agglomeration. Further, the one or more mutation in one of the light chain and heavy chain preferably is a conservative mutation and/or has an amino acid sequence with at least 95% homology or identity to one of SEQ ID NO: 85, SEQ ID NO: 86, SEQ ID NO: 87, SEQ ID NO: 88, SEQ ID NO: 89 and SEQ ID NO: 90 for the VH, and to one of SEQ ID NO: 91, SEQ ID NO: 92, SEQ ID NO: 93, SEQ ID NO: 94, SEQ ID NO: 95 and SEQ ID NO: 96 for the VL.

Most preferably, the binding peptide comprises one of the amino acid sequences constituted by SEQ ID NO: 85-SEQ ID NO: 97-SEQ ID NO: 103-SEQ ID NO: 91-SEQ ID NO: 109, or SEQ ID NO: 86-SEQ ID NO: 98-SEQ ID NO: 104-SEQ ID NO: 92-SEQ ID NO: 110, or SEQ ID NO: 87-SEQ ID NO: 99-SEQ ID NO: 105-SEQ ID NO: 93-SEQ ID NO: 111, or SEQ ID NO: 88-SEQ ID NO: 100-SEQ ID NO: 106-SEQ ID NO: 94-SEQ ID NO: 112, or SEQ ID NO: 89-SEQ ID NO: 101-SEQ ID NO: 107-SEQ ID NO: 95-SEQ ID NO: 113, or SEQ ID NO: 90-SEQ ID NO: 102-SEQ ID NO: 108-SEQ ID NO: 96-SEQ ID NO: 114, with optional moieties linked to the N-terminus and/or C-terminus.

One advantageous embodiment of the invention relates to a binding peptide defined above, which binding peptide is a single chain peptide, preferably said single chain peptide being selected from SEQ ID NO: 122 to SEQ ID NO: 124.

The above mentioned single chain peptide is a scFv fragment.

Another advantageous embodiment of the invention relates to a binding peptide as defined above, wherein the light chain variable amino acid sequence is comprised on a first peptide and the heavy chain variable amino acid sequence is comprised on a second peptide, preferably said first peptide being selected from SEQ ID NO: 125 to SEQ ID NO: 130, and said second peptide being selected from SEQ ID NO: 131 to SEQ ID NO: 136.

The above mentioned first peptide can contain, or not, a signal peptide. Therefore, the above mentioned first peptide with signal peptide is selected from SEQ ID NO 125 to SEQ ID NO 127, and said first peptide without signal peptide is selected from SEQ ID NO 128 to SEQ ID NO 130.

The above mentioned second peptide can contain, or not, a signal peptide. Therefore, the above mentioned first peptide with signal peptide is selected from SEQ ID NO 131 to SEQ ID NO 133, and said first peptide without signal peptide is selected from SEQ ID NO 134 to SEQ ID NO 136.

In one other specific embodiment, the binding peptide mentioned above is constituted by a couple of a light chain and a heavy chain selected from:

the couple consisting of the light chain amino acid sequence as set forth in SEQ ID NO: 125 and the heavy chain amino acid sequence as set forth in SEQ ID NO: 131, the couple consisting of the light chain amino acid sequence as set forth in SEQ ID NO: 126 and the heavy chain amino acid sequence as set forth in SEQ ID NO: 132, the couple consisting of the light chain amino acid sequence as set forth in SEQ ID NO: 127 and the heavy chain amino acid sequence as set forth in SEQ ID NO: 133, the couple consisting of the light chain amino acid sequence as set forth in SEQ ID NO: 128 and the heavy chain amino acid sequence as set forth in SEQ ID NO: 134, this binding peptide corresponds to the antibody HT186-B7, the couple consisting of the light chain amino acid sequence as set forth in SEQ ID NO: 129 and the heavy chain amino acid sequence as set forth in SEQ ID NO: 135, this binding peptide corresponds to the antibody HT186-G2, the couple consisting of the light chain amino acid sequence as set forth in SEQ ID NO: 130 and the heavy chain amino acid sequence as set forth in SEQ ID NO: 136, this binding peptide corresponds to the antibody HT186-D11.

It is well know in the art that antibodies are constituted by 2 similar or different, pairs of heavy chain and light chain.

In one advantageous embodiment, the invention relates to a binding peptide as defined above which chosen among:

the antibody HT186-G2 consisting of a dimer of the couple consisting of the light chain amino acid sequence as set forth in SEQ ID NO: 129 and the heavy chain amino acid sequence as set forth in SEQ ID NO: 135, the antibody HT186-B7 consisting of a dimer of the couple the light chain amino acid sequence as set forth in SEQ ID NO: 128 and the heavy chain amino acid sequence as set forth in SEQ ID NO: 134, and the antibody HT186-D11 consisting of a dimer of the light chain amino acid sequence as set forth in SEQ ID NO: 130 and the heavy chain amino acid sequence as set forth in SEQ ID NO: 136.

In an advantageous embodiment, the invention relates to binding peptide or antibody as defined above produced by the rat hybridoma YB2/0 (cell YB2/3HL.P2.G11.16Ag.20, deposited at the American Type Culture Collection under the number ATCC CRL-1662).

The YB2/0 cell line is chosen since it produces antibodies having an enhanced ADCC activity compared to the same antibody produced by CHO cell line.

The invention relates to binding peptide or antibody as defined above, produced by any other means known in the art allowing the increase of the ADCC activity of said antibodies or binding peptides.

DETAILED DESCRIPTION OF THE INVENTION

The invention is now described in greater detail by way of examples with reference to the figures, wherein FIGS. 1 A), B) and C) show tables, wherein the amino acid sequences of regions of binding peptides are shown, FIG. 2 shows ELISA results with the X-axis giving the concentration in µg/mL of antibody containing a binding peptide of the invention in a scFv arrangement, and comparative antibody IIB6 and BSA, FIG. 3 shows SDS-PAGE results, stained for total protein, showing purification of antibody from heterologous expression of antibodies in E. coli of A) HT186-D11, B) HT200-3A-C1, C) HT220-M-D1, D) HT220-M-G8, E) HT186-B7 and F) HT186-G2 of the present invention, FIG. 4 shows surface plasmon resonance analyses of antibodies, namely under A) HT186-D11, B) HT200-3A-C1, C) HT220-M-D1, D) HT220-M-G8, E) HT186-B7, and F) HT186-G2, for comparison on the same chip, FIG. 5A through FIG. 5J show FACS results of scFv, namely A1) comparative anti-MUC scFv IIB6 on MCF7 cells, A2) IIB6 on T47D cells, A3) IIB6 on SKOV3 cells, A4) IIB6 on HEK293-T cells, B1) HT186-D11 on MCF7 cells, B2) HT186-D11 on T47D cells, B3) HT186-D11 on SKOV3 cells, B4) HT186-D11 on HEK293-T cells, C1) HT200-3A-C1 on MCF7 cells, C2) HT200-3A-C1 on T47D cells, C3) HT200-3A-C1 on SKOV3 cells, C4) HT200-3A-C1 on HEK293-T cells, D1) HT220-M-D1 on MCF7 cells, D2) HT220-M-D1 on T47D cells, D3) HT220-M-D1 on SKOV3 cells, D4) HT220-M-D1 on HEK293-T cells, E1) HT220-M-G8 on MCF7 cells, E2) HT220-M-G8 on T47D cells, E3) HT220-M-G8 on SKOV3 cells, E4) HT220-M-G8 on HEK293-T cells, F1) HT186-B7 on MCF7 cells, F2) HT186-B7 on T47D cells, F3) HT186-B7 on SKOV3 cells, F4) HT186-B7 on HEK293-T cells, G1) HT186-G2 on MCF7 cells, G2) HT186-G2 on T47D cells, G3) HT186-G2 on SKOV3 cells, G4) HT186-G2 on HEK293-T cells FIG. 6 shows ELISA data for antibodies examined in the present invention for long-term stability in aqueous solution at 37° C., for A) HT186-D11, B) HT200-3A-C1, C) HT220-M-D1, D) HT220-M-G8, E) HT186-B7, F) HT186-G2, and G) comparative IIB6, FIG. 7 shows size exclusion chromatograms of purified antibody for determination of unspecific aggregation in solution for A) HT186-D11, B) HT200-3A-C1, C) HT220-M-D1, D) HT220-M-G8, E) HT186-B7, F) HT186-G2, and G) comparative IIB6.

Figure 26:
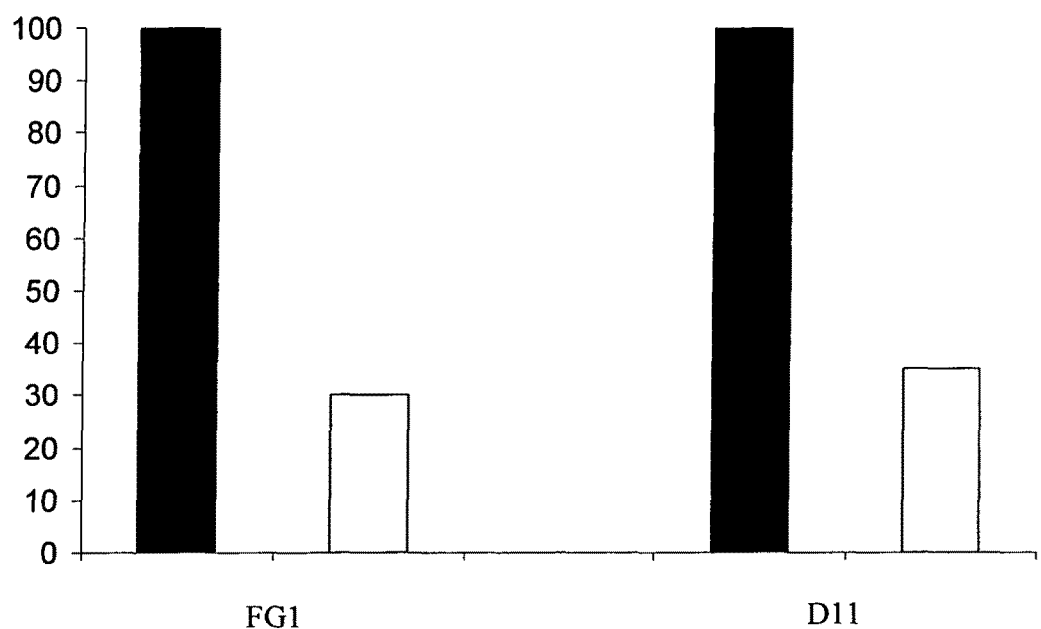

FIG. 26 the percentage of internalisation after incubation 1 hour at 37° C. (white columns) compared with incubation at 4° C. (black columns). FG1 represents control antibody. Y-axis represents the mean of fluorescence intensity In FIG. 1, there are shown amino acid sequences for hypervariable complementary determining regions (CDR) CDR1, CDR2, CDR3 in their preferred arrangement between framework regions (FR) FR1, FR2, FR3 and FR4 for the heavy chain variable fragment (VH) and the light chain variable fragment (VL), respectively, for antibodies comprising, preferably constituting, the binding peptides of the invention. The assignment of amino acid sequence sections to hypervariable region sections, namely to FR and CDR, respectively, allows to freely recombine at least one of FR and one of CDR, preferably in the arrangement of FRI-CDR1-FR2-CDR2-FR3-CDR3-FR4, independently from heavy chain and light chain variable regions, to obtain an antibody according to the invention. The preferred antibodies of the invention comprise CDRs and FRs from the binding peptides designated HT186-D11, HT200-3A-C1, HT220-M-D1, HT220-M-G8, HT186-B7 and/or HT186-G2, most preferably the heavy chain variable fragments in association with the light chain variable fragments, e.g. SEQ ID NO: 85 associated with SEQ ID NO: 91, Seq.-ID-No 86 associated with SEQ ID NO: 92, SEQ ID NO: 87 associated with SEQ ID NO: 93, SEQ ID NO: 88 associated with SEQ ID NO: 94, SEQ ID NO: 89 associated with SEQ ID NO: 95, and SEQ ID NO: 90 associated with SEQ ID NO: 96 respectively.

Further, FIG. 1 contains amino acid sequences of scFv antibody comprising the binding peptide consisting of VH-truncated CH1-linker-VL-truncated CL, wherein preferably one antibody comprises the VH and VL region originating from one of HT186-D11 (Seq.-ID No. 85 or Seq.-ID No. 91), HT200-3A-C1 (Seq.-ID No. 86 or Seq.-ID No. 92), HT220-M-D1 (Seq.-ID No. 87 or Seq.-ID No. 93), HT220-M-G8 (Seq.-ID No. 88 or Seq.-ID No. 94), HT186-B7 (Seq.-ID No. 89 or Seq.-ID No. 95), or HT186-G2 (Seq.-ID No. 90 or Seq.-ID No. 96). Further, antibodies of the invention also comprise the association of one VH of one of the amino acid sequences SEQ ID NO: 85 to SEQ ID NO: 90 with one VL of one of the amino acid sequences SEQ ID NO: 91 to SEQ ID NO: 96, with one of the CH1 regions of one of the amino acid sequences SEQ ID NO: 97 to SEQ ID NO: 102, one of the linkers of one of the amino acid sequences SEQ ID NO: 103 to SEQ ID NO: 108, and one of the amino acid sequences SEQ ID NO: 103 to SEQ ID NO: 108 for the linker (also termed Yol), and one of the CL of amino acid sequences SEQ ID NO: 109 to SEQ ID NO: 114.

Embodiments according to the invention comprise the binding peptides being linked to effector components, which effector components accordingly can be coupled to the exemplary antibodies shown, e.g. by translation of a conjugate comprising the antibody and the effector component, e.g. by translation from a single coding nucleic acid sequence. Optionally, a nucleic acid sequence can be used for expression, which nucleic acid sequence encodes the antibody of the invention, e.g. as an Ig, and/or including a multimerization domain and/or an effector component.

An scFv antibody section, which can optionally be coupled to an effector component, essentially consists of a light chain variable region connected to a heavy chain variable region via an intermediate linker peptide such that the variable regions can associate to one another for forming the antigen binding region, which is also termed paratope. As an alternative embodiment, two associable scFv antibodies are produced, which associate to a diabody, in each case preferably with association of one heavy chain variable region and one light chain variable region contained in one single polypeptide chain or contained in separate polypeptide chains.

An example for heterologous multimerization domains, a helix-turn-helix-motive is a component C- or N-terminally added to a light chain variable region or a heavy chain variable region, allowing the association of two single polypeptide antibodies. In the alternative to a synthetic multimerization domain, natural antibody domains can be contained within the antibody, e.g. connected to a light chain variable region and/or a heavy chain variable region, wherein the antibody domains preferably are selected from a light chain constant region CH1, CH2 and/or CH3, e.g. resulting in the antibody being a Fab or a natural immunoglobulin, preferably IgG.

As further examples for multimerization domains, the biotin acceptor domain (BAD, amino acid sequence available under accession No. 2zta, PDB) is a suitable component linked to an scFv, which BAD (described in Schatz, Biotechnology 11 (10), 1138-1143 (1993)) after biotinylation allows the association of the biotinylated antibody to avidin or streptavidin. Further multimerization domains that can be contained in one polypeptide chain comprising the antibody of the invention are the leucin zipper domain, the modified leucin zipper domain tetraZIP which results in a tetramerisation of antibody containing tetraZIP, or the tetramer relation domain of p53 or amphipathic helices (amino acid sequences available in Plückthun et al., Immunotechnology 3(2), 83-105 (1997)), originating from the human transcription effector suppressor p53 (amino acid sequence available under accession No. 2j0z, PDB). Preferably, linker peptide sequences are arranged between multimerization domains and antibody regions to avoid interference of the multimerization with antigen binding.

Using standard DNA cloning procedures, a library of nucleic acid sequences encoding antibody according to the invention was generated by enriching MUC1-binding VH and VL that were displayed on the surface of phage particles.

For mutation of antibody encoding genes contained in the antibody gene library, amplification using error prone PCR utilizing MutazymeII® DNA polymerase (obtainable from Stratagene, Amsterdam) was used, which statistically generates a mutation rate of up to 16 nucleotide exchanges per 1000 bp in one PCR of approximately 35 amplification cycles, with a mutation rate of A or T to N of approximately 50%, and G or C to N of approximately 44%.

For cloning of antibody comprised of a combination of framework regions and CDRs in a new arrangement, preferably by exchanging one framework region for a framework region of the same localization (as indicated by the same numbering of FR) and/or of a CDR, respectively, PCR cloning could be employed, using PCR primers overlapping the region encoding the desired amino acid exchanges.

The enrichment of phage encoding and expressing antibody sections with increased antigen binding, i.e. having a lower dissociation constant, was obtained by the so-called panning procedure, comprising the step of incubating antibody presenting phage with immobilized antigen, followed by extensive washing in phosphate buffered saline including Tween20 for 7 days in 2 L PBS under slight stirring at 4° C., followed twice by further washing of recovered immobilized antigen with an additional 1 L PBS at 4° C. for 7 days each. Finally, phages that were bound to immobilized antigen were released by trypsination and used for infection of *E. coli*. For immobilisation of antigen, microtitre plates were coated with the antigen, or alternatively, suspendable synthetic beads coated with streptavidin were coated with biotinylated antigen. As the antigen, synthetic MUC1 peptide APDTRPAPGSTAPPAC (Seq.-ID No. 115) or APDTRPAPGSTAPPAHGVTSAPDTRPA PGSTA (Seq.-ID No. 116) or Biotin-β-A-β-A-APDTRPAPGSTAPPAHGVTSAPDTRPAP GSTA (Seq.-ID No. 117) or APDTRPAPGSTAPPAHGVTSAPDTRPAPGSTAC (Seq.-ID No. 118) was used for the analysis of monoclonal soluble antibody fragments.

As a further variation of panning in solution, incubation of the antigen with the antibody presenting phage was in the presence of unlabelled antigen (MUC1 peptide), serving as a competitor for the immobilized MUC1 peptide.

From the various steps of the enrichment of anti-MUC1 antibody presenting phage, the heavy chain variable regions of SEQ ID NO: 85 to SEQ ID NO: 90 were found, associated with light chain variable regions of amino acid sequences SEQ ID NO: 91 to SEQ ID NO: 96, respectively.

Interestingly, in comparison to anti-MUC1 antibody IIB6, these antibodies show a higher affinity for MUC1 antigen, a drastically increased stability, e.g. in a long time incubation at 37° C. in aqueous solution with maintenance of the antigen specificity as determined in an ELISA assay, affinity to an advantageous binding epitope on the MUC1 antigen and a low propensity to agglomerate independent of multimerization domains linked to the binding peptides of the invention. Non-specific agglomeration in solution generally leads to a reduction in biological activity and is therefore undesired. Stability data are shown in Example 5.

Generally, an expression vector for use in the preferred process for production of antibody according to the invention, e.g. for heterologous expression in a micro-organism, preferably in a host bacterium, e.g a Gram-negative bacterium, contains a nucleic acid sequence encoding the antibody and, preferably contains the coding region for an N-terminal signal sequence for transport of the translation product into the periplasm. As it is known in the art, an expression vector in addition to vector specific elements like an origin of replication and a selection marker, according to the invention contains a nucleic acid sequence encoding the antibody of the invention comprised in an expression cassette, optionally encoding additional effector components, to produce a single chain amino acid sequence comprising the binding peptide. As one example for a nucleic acid sequence, functionally arranged from 5' to 3', the coding region for an scFv is contained, optionally followed by a coding sequence for a heavy multimerization domain. The linker peptide connecting the heavy chain variable region binding peptide with the light chain variable region in the embodiment of an scFv as used in the examples has the sequence indicated in Table 1C. In the alternative to this arrangement, the scFv can contain the light chain variable region binding peptide-linker-heavy chain variable region binding peptide.

For production of antibody according to the invention, the scFv embodiment is preferred, for example in addition including a C-terminally added multimerization domain BAD, tetraZIP, ZIP, dHLX, p53, preferably VH for heavy chain binding peptide and VL for light chain binding peptide, respectively, optionally followed by a C-terminally arranged His(6)-tag.

Further, the coding sequence encoding an N-terminally arranged periplasm signal sequence (e.g. pelB) for transport of the antibody into the periplasmic space. The coding sequence can be functionally arranged between a standard bacterial promoter (PA1/04/07) and a T7 terminator, transferred into E. coli and cultivated. Multimerization domains dHLX, ZIP, p53 and tetraZIP are self-associating, whereas for antibody containing BAD, biotin ligase is concurrently expressed in E. coli to covalently couple biotin to the C-terminus of the polypeptide chain. Biotinylated scFv after expression and purification are incubated in the presence of streptavidin.

TABLE 1

Production yield (μg/L) of antibody variants in bacterial expression

| scFv | Conc. in eluate (mg/mL) | Vol. Eluate (mL) | Yield scFv/culture volume (mg/L) |
|---|---|---|---|
| IIB6 | 1.09 | 2 | >2.2 |
| HT186-D11 | 1.45 | 2 | >2.9 |
| HT200-3A-C1 | 0.80 | 2 | >1.6 |
| HT220-M-D1 | 0.79 | 2 | >1.6 |
| HT220-M-G8 | 1.60 | 2 | >3.2 |
| HT186-B7 | 0.49 | 5 | >2.5 |
| HT186-G2 | 0.42 | 2 | >0.8 |

Figure 2:
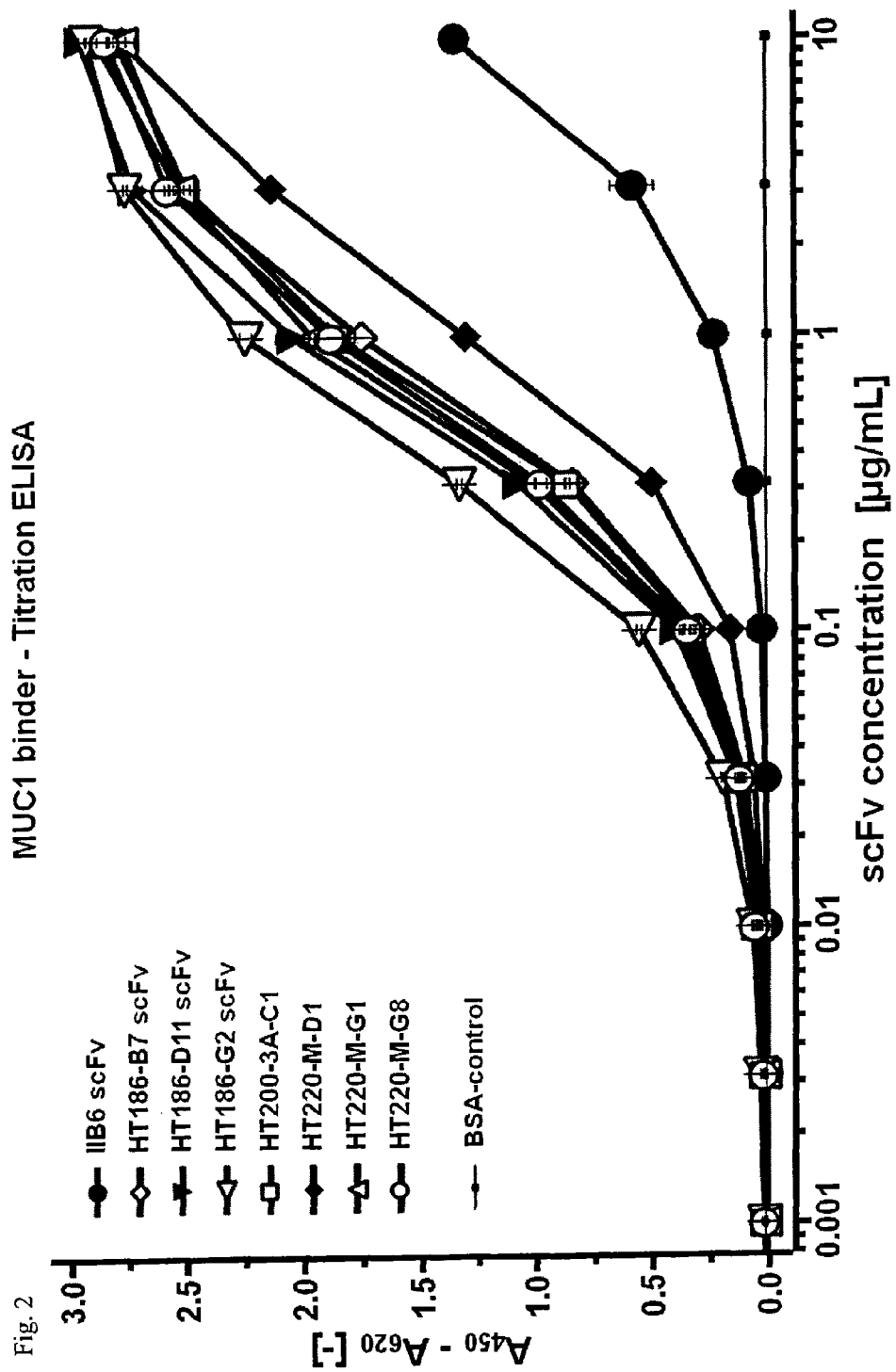
Figure 3:
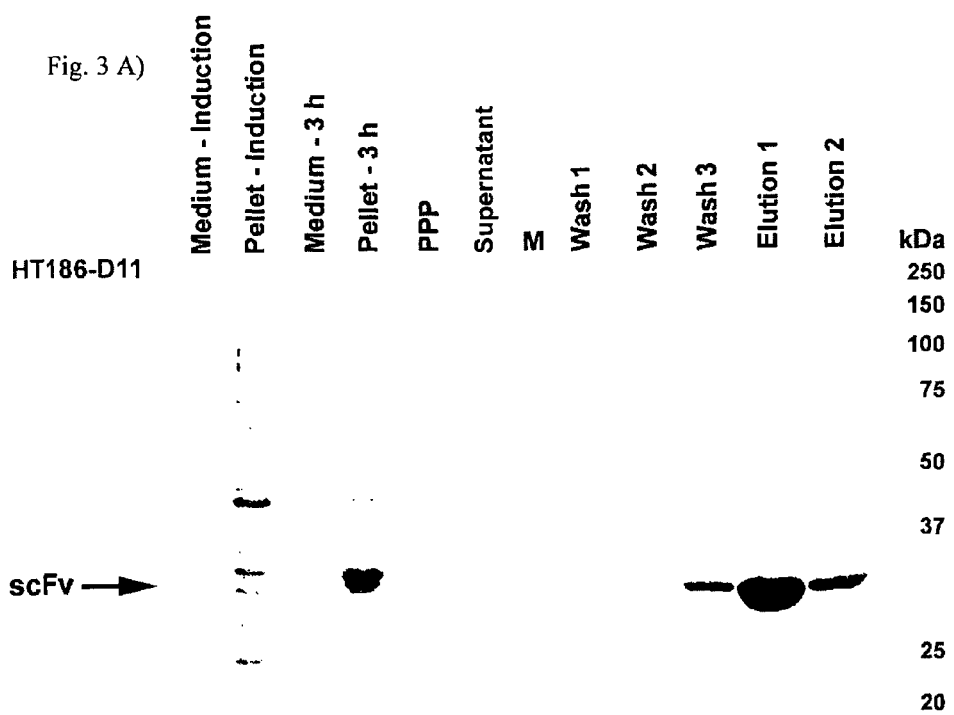
Figure 3:
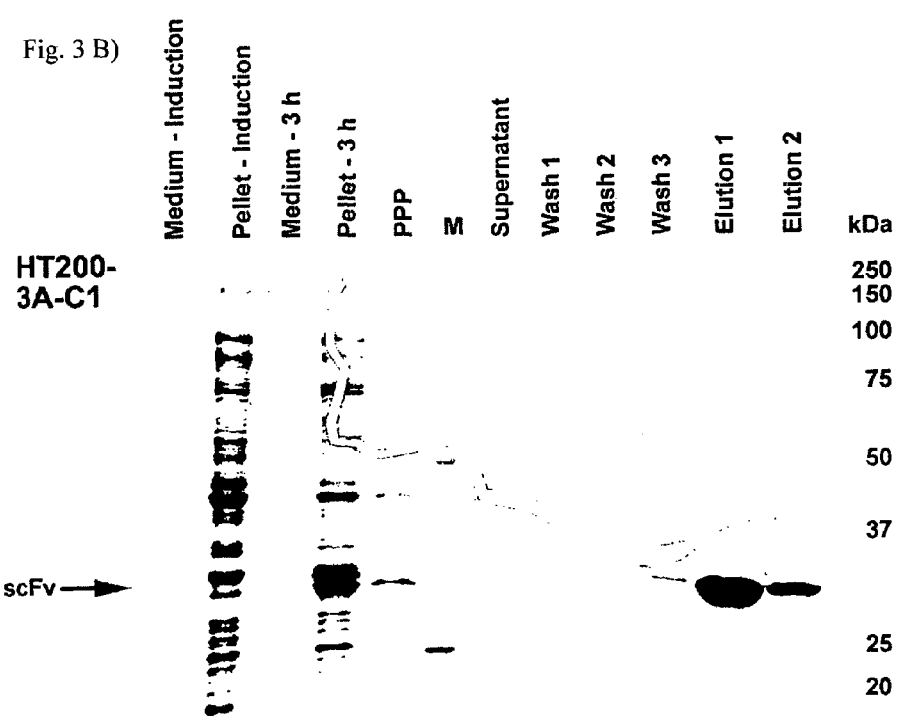
Figure 3:
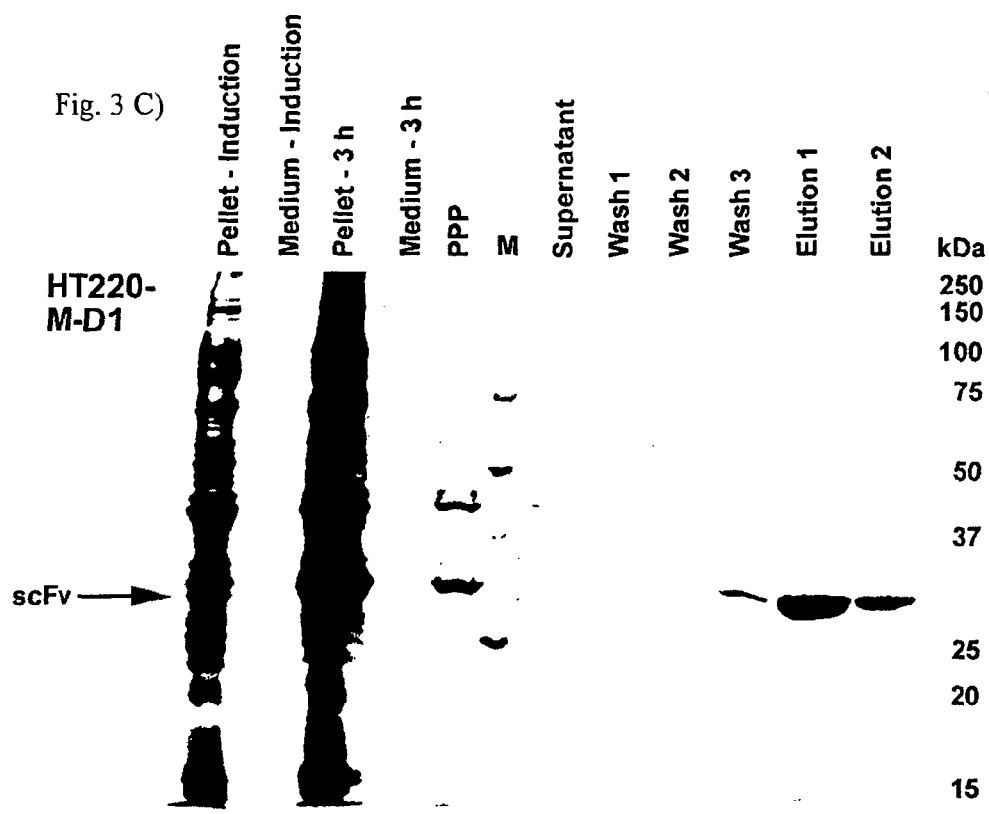
Figure 3:
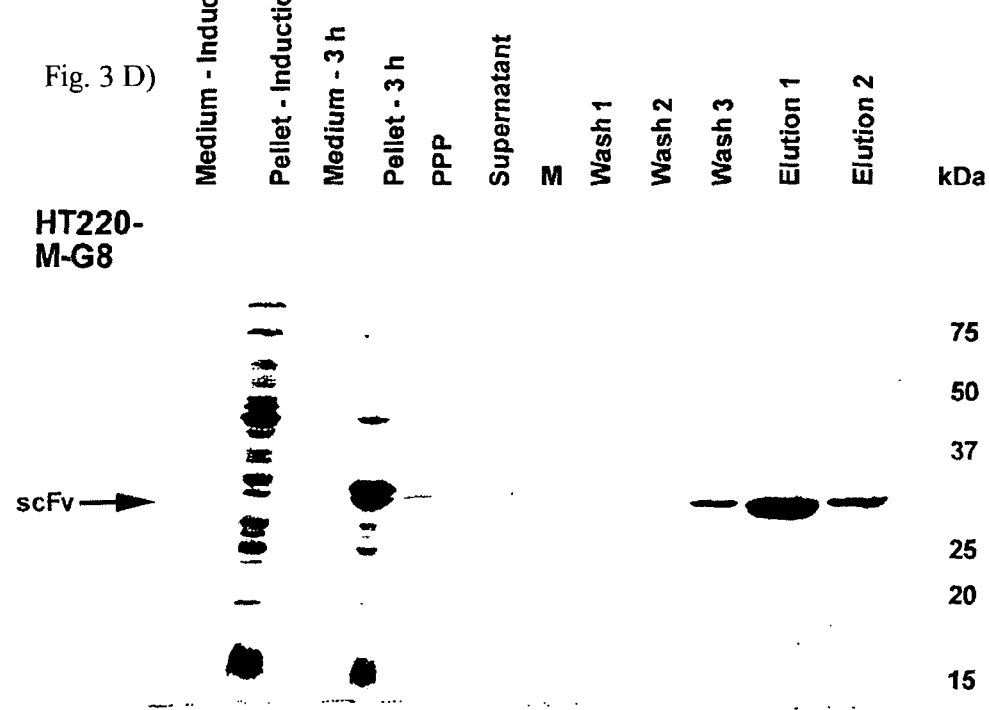
Figure 3:
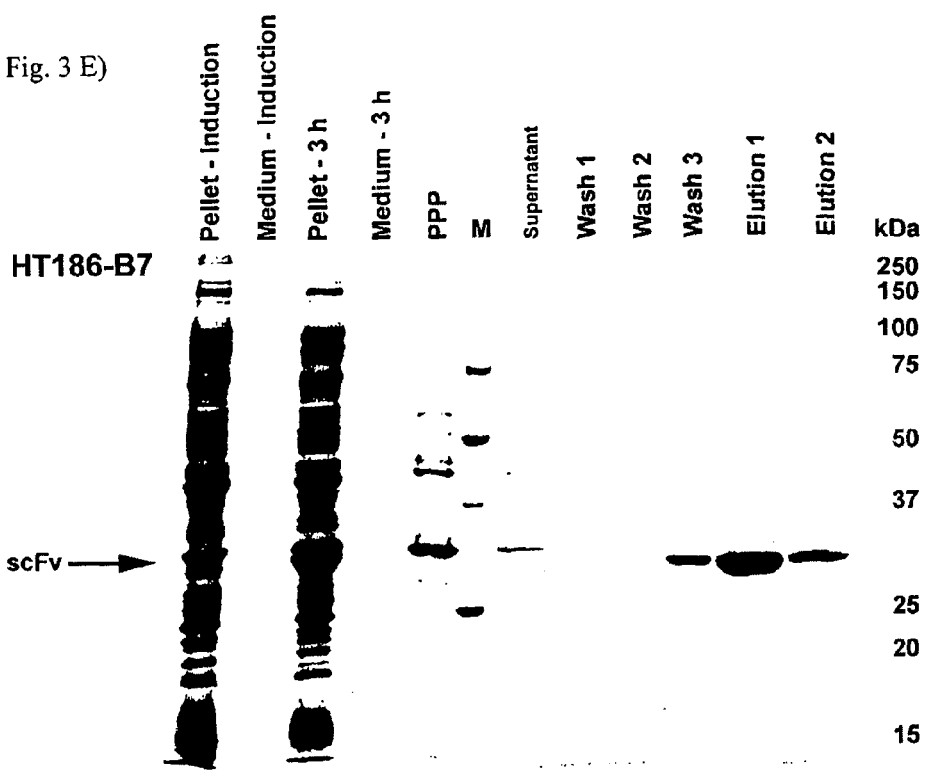
Figure 3:
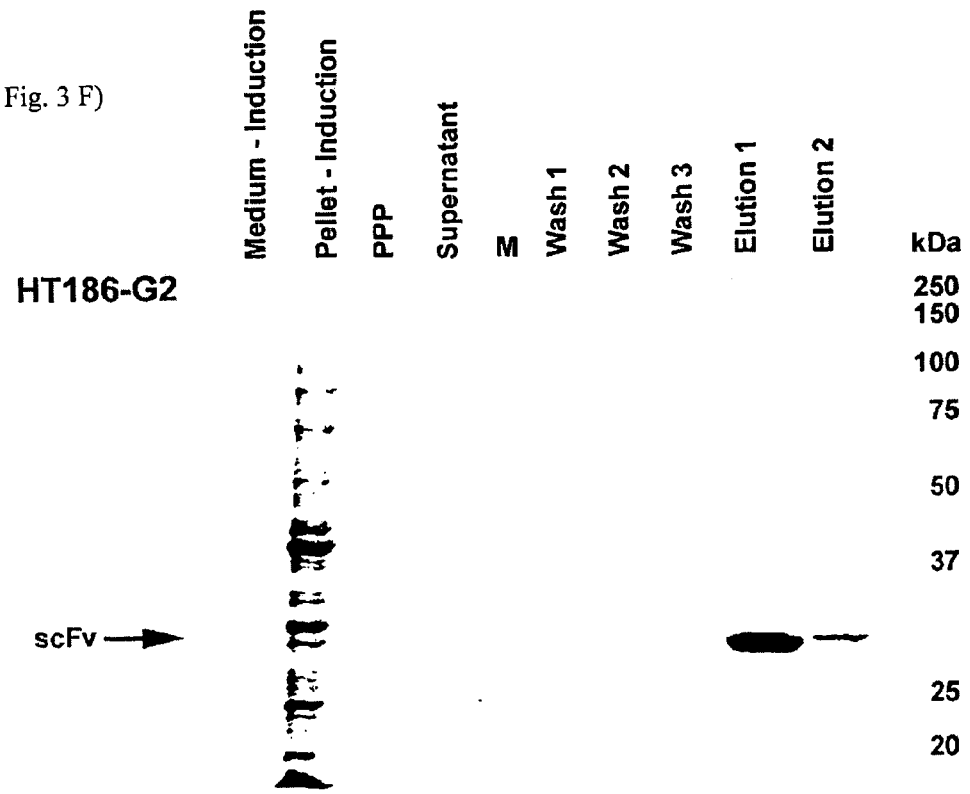

SDS-PAGE analytical results from samples of the purification process steps from antigen expressing E. coli are shown in FIG. 3, indicating under A) preferred antibody HT186-D11, B) HT200-3A-C1, C) HT220-M-D1, D) HT220-M-G8, E) HT186-B7 and F) HT186-G2. For these antibodies according to the invention, a prominent band for the elution sample (elution 1) of the molecular size of the scFv (indicated by arrow) is visible.

Figure 4:
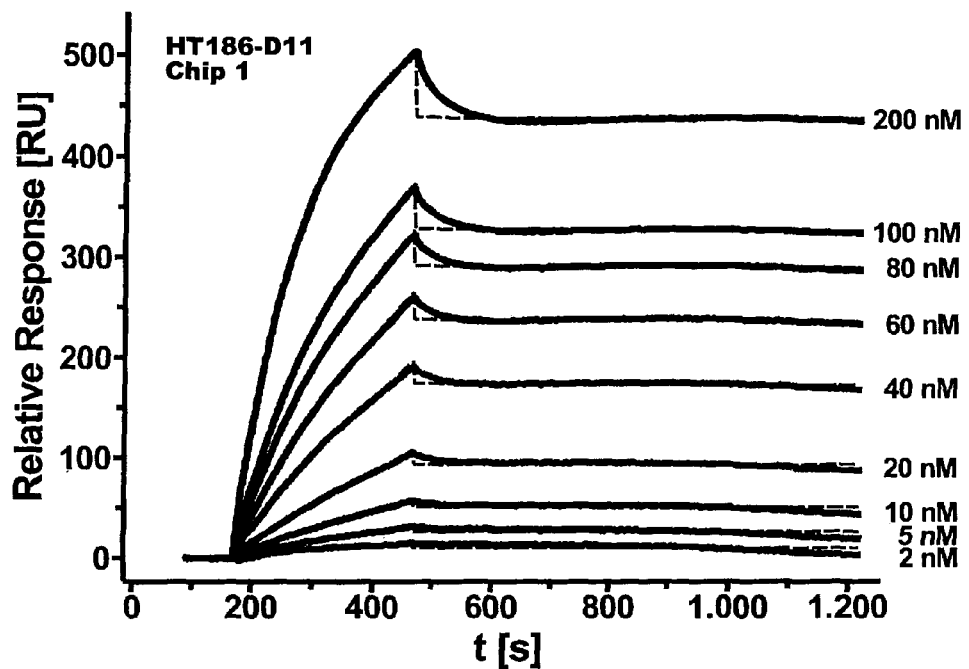
Figure 4:
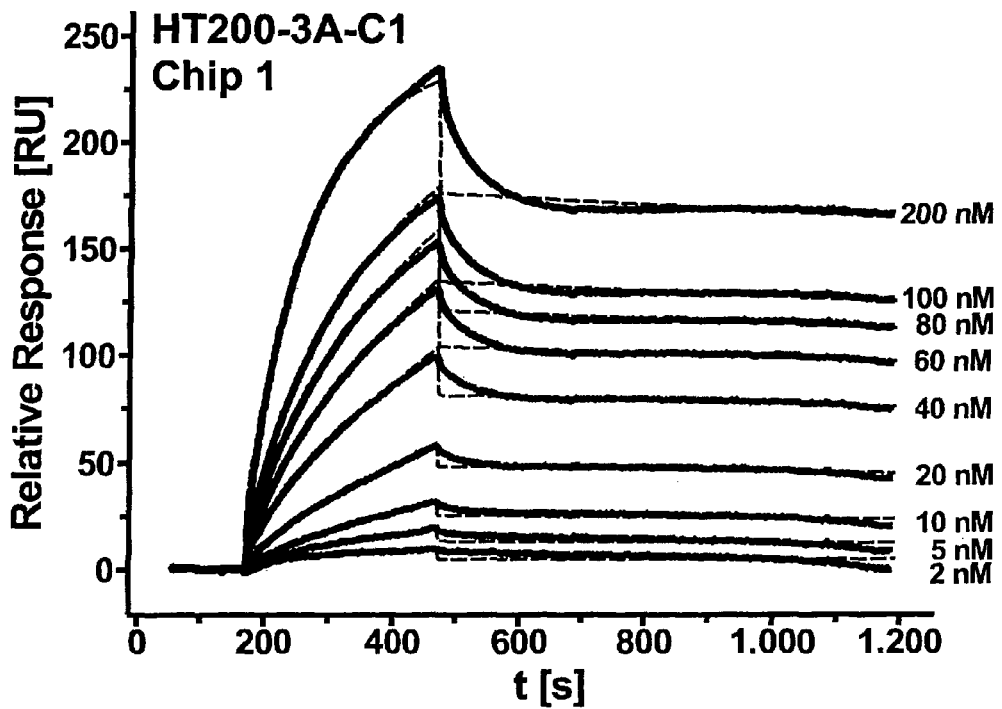
Figure 4:
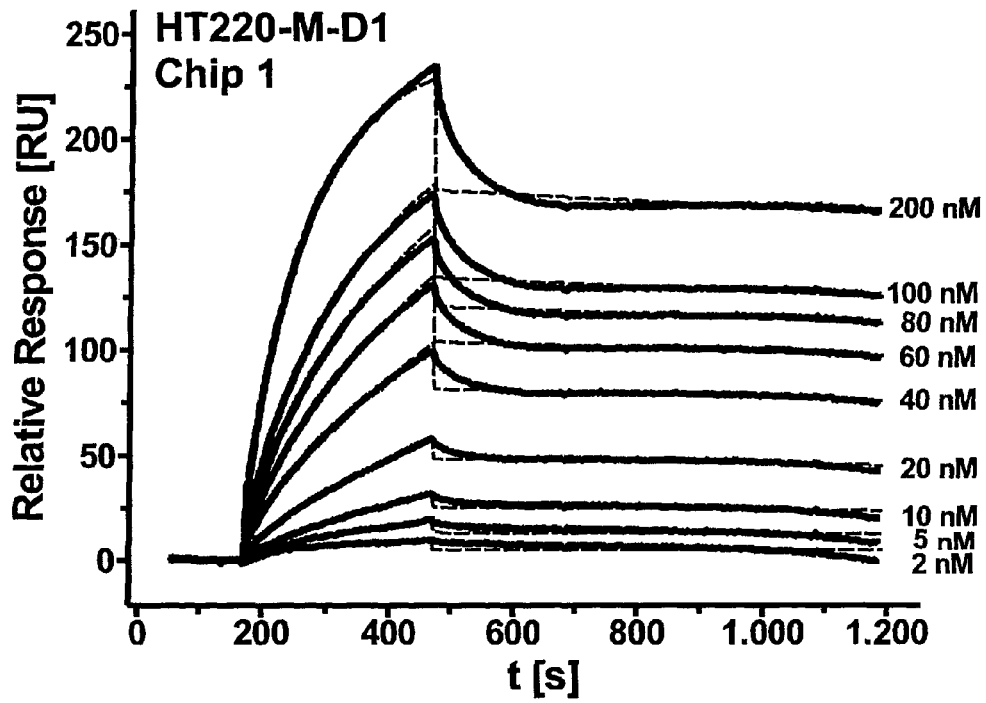
Figure 4:
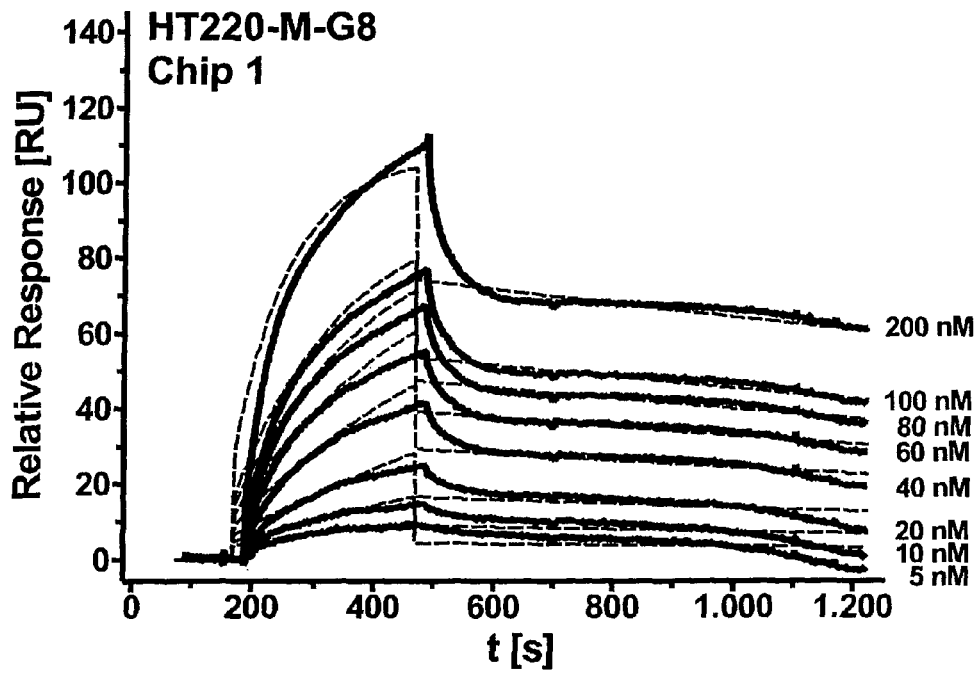
Figure 4:
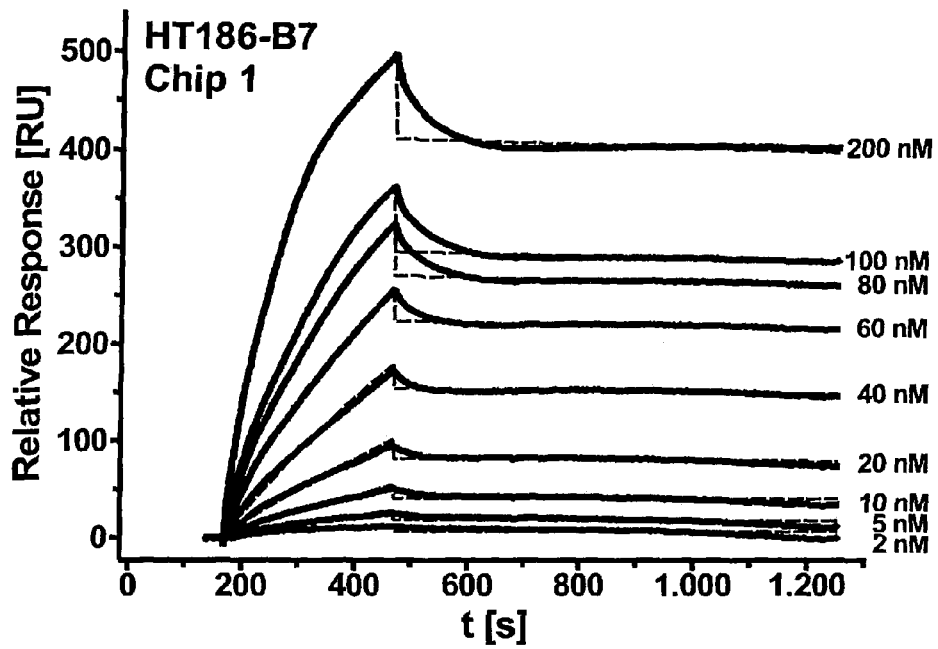
Figure 4:
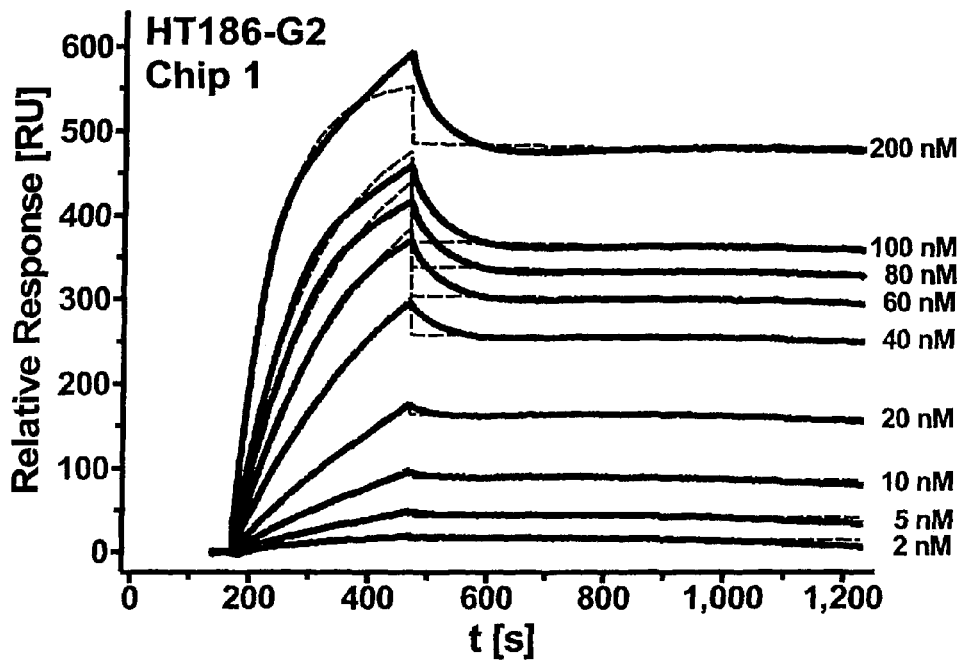
Figure 5A:
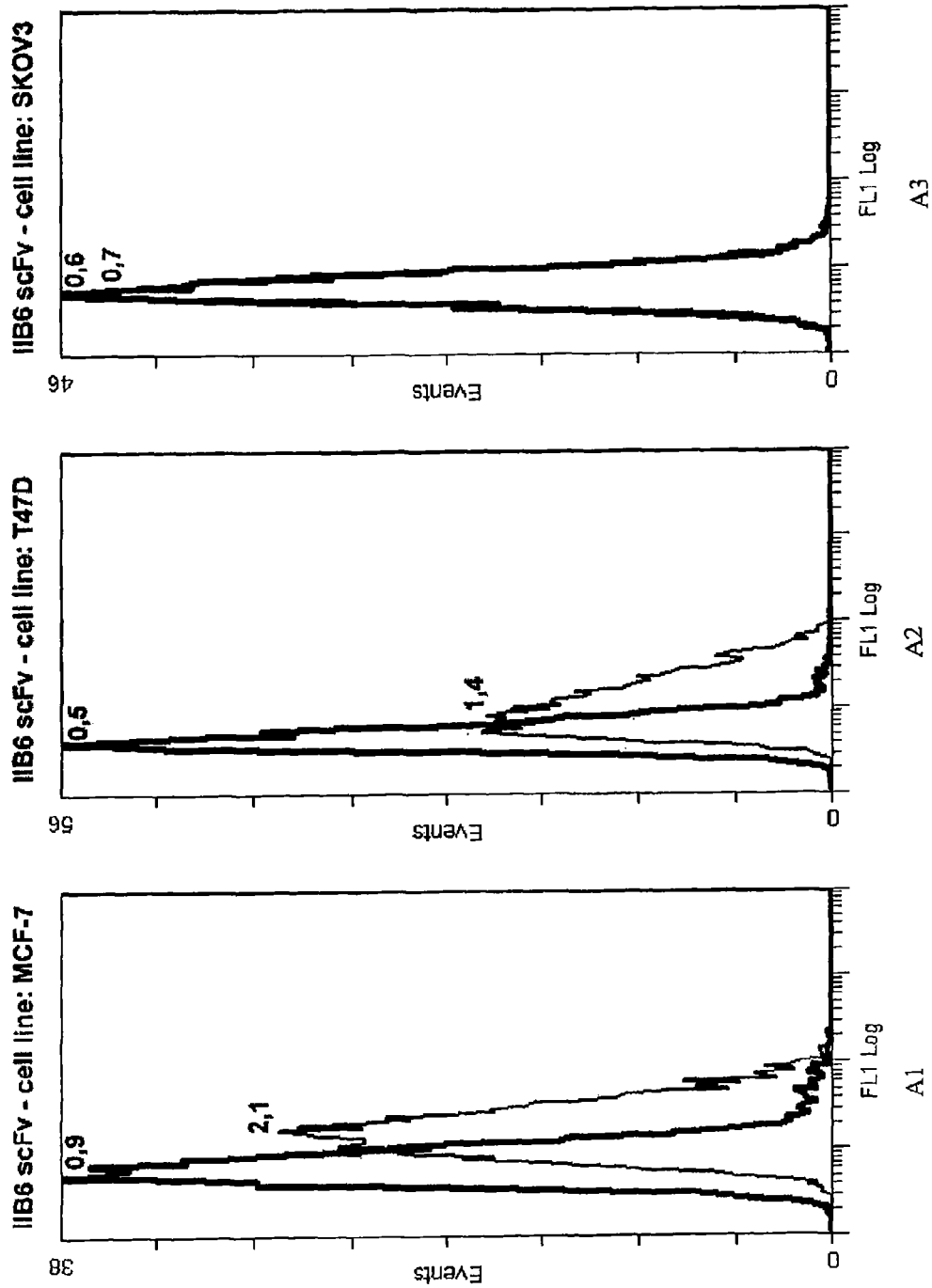
Figure 5B:
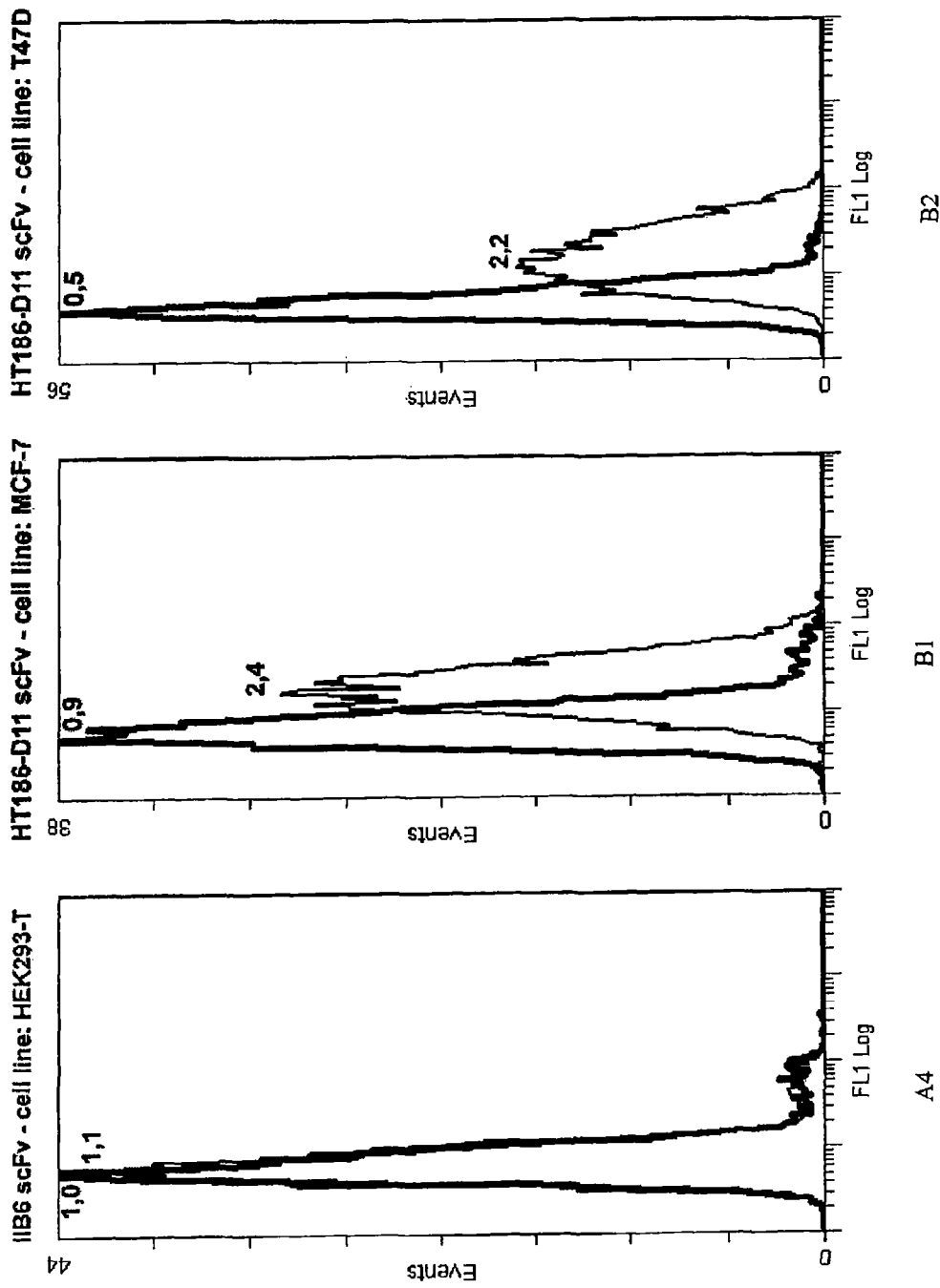
Figure 5C:
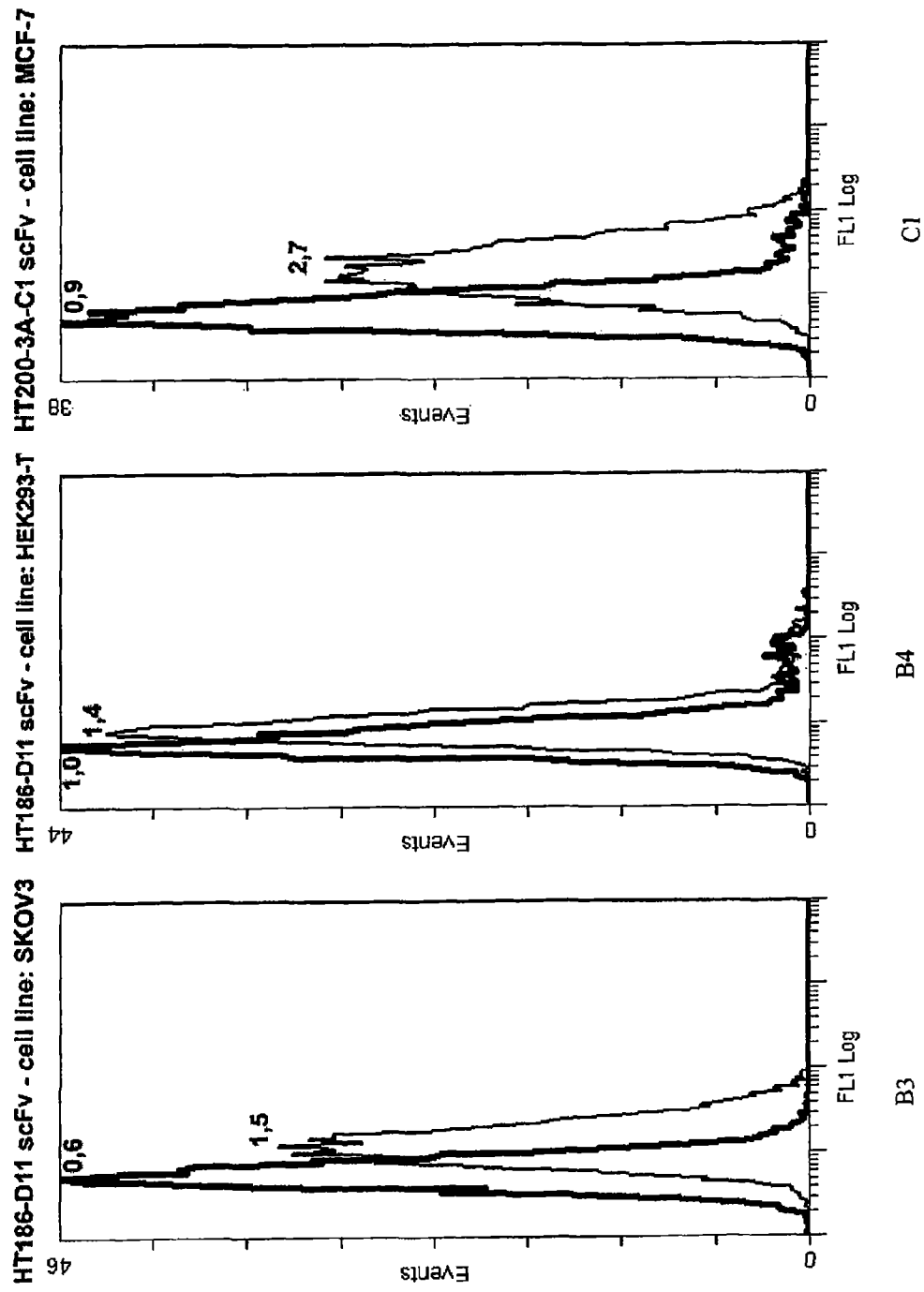
Figure 5D:
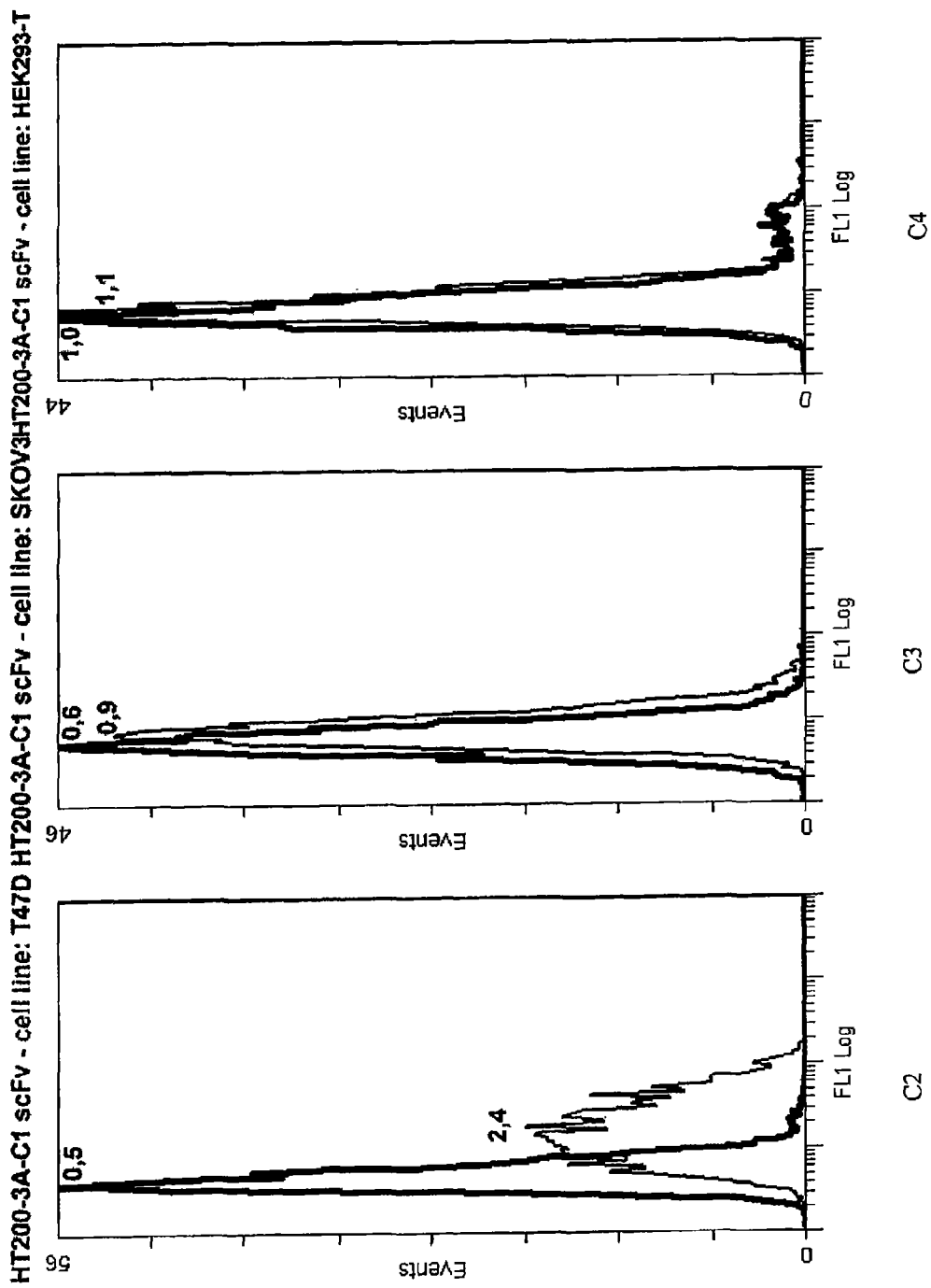
Figure 5E:
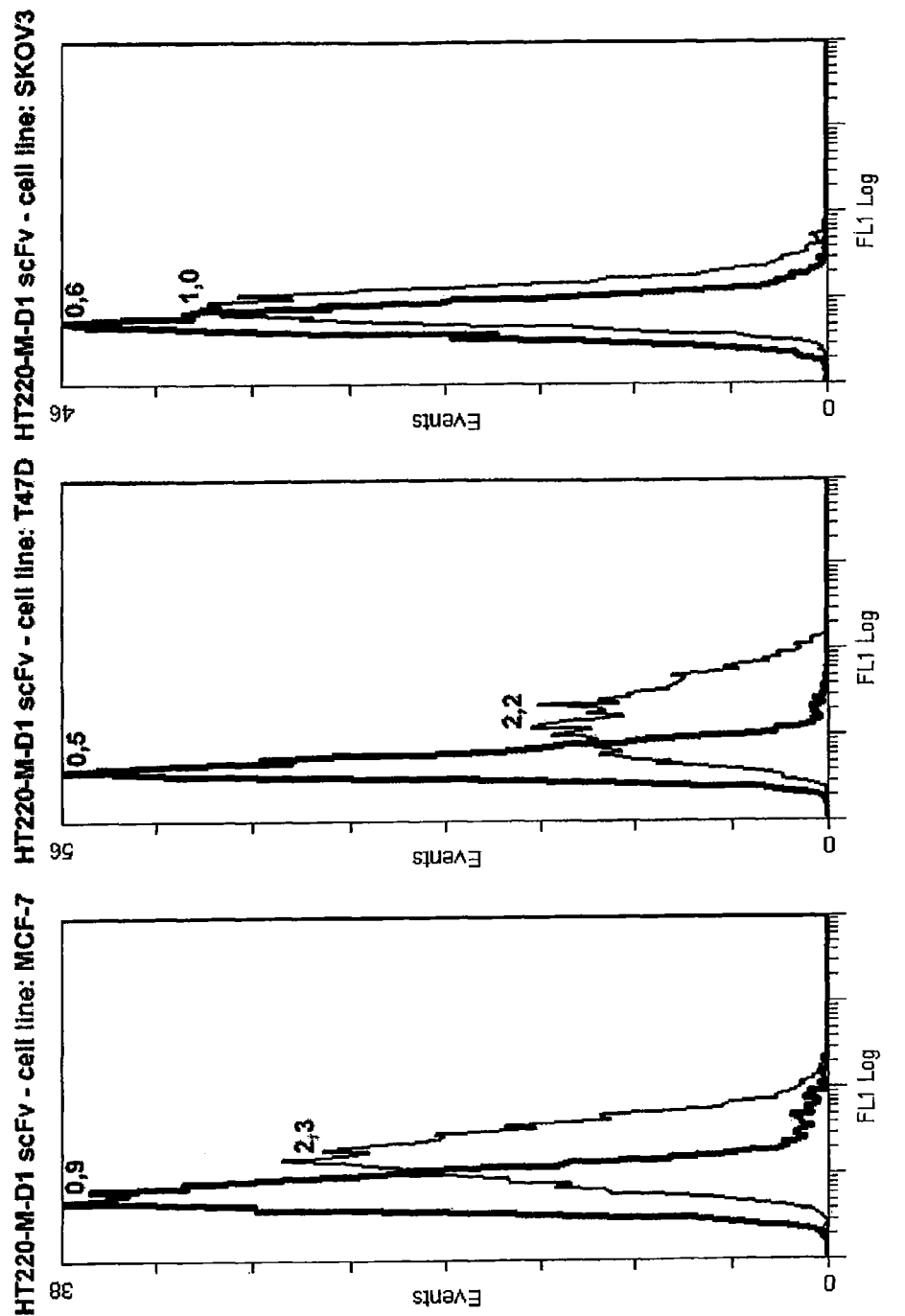
Figure 5F:
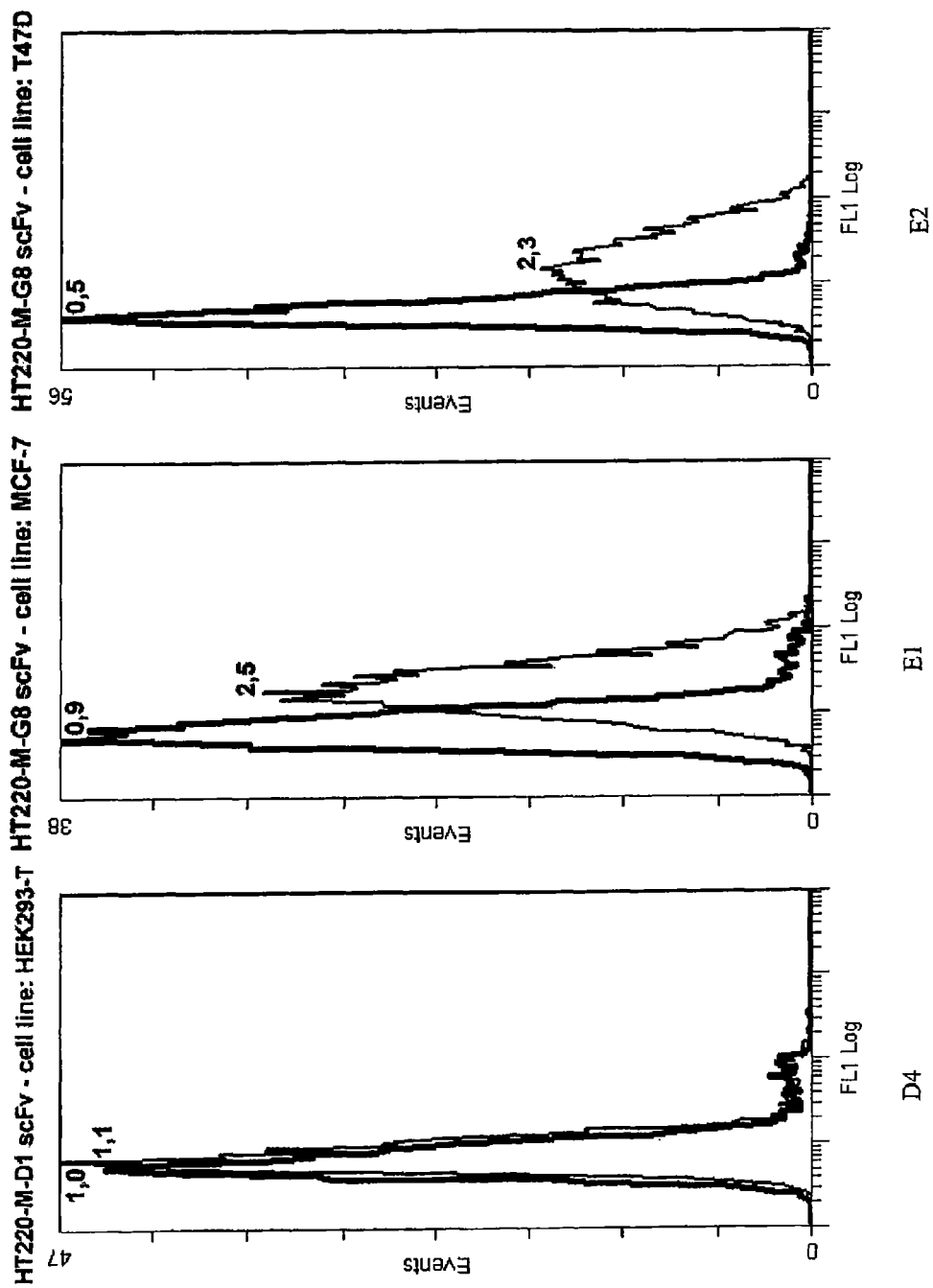
Figure 5G:
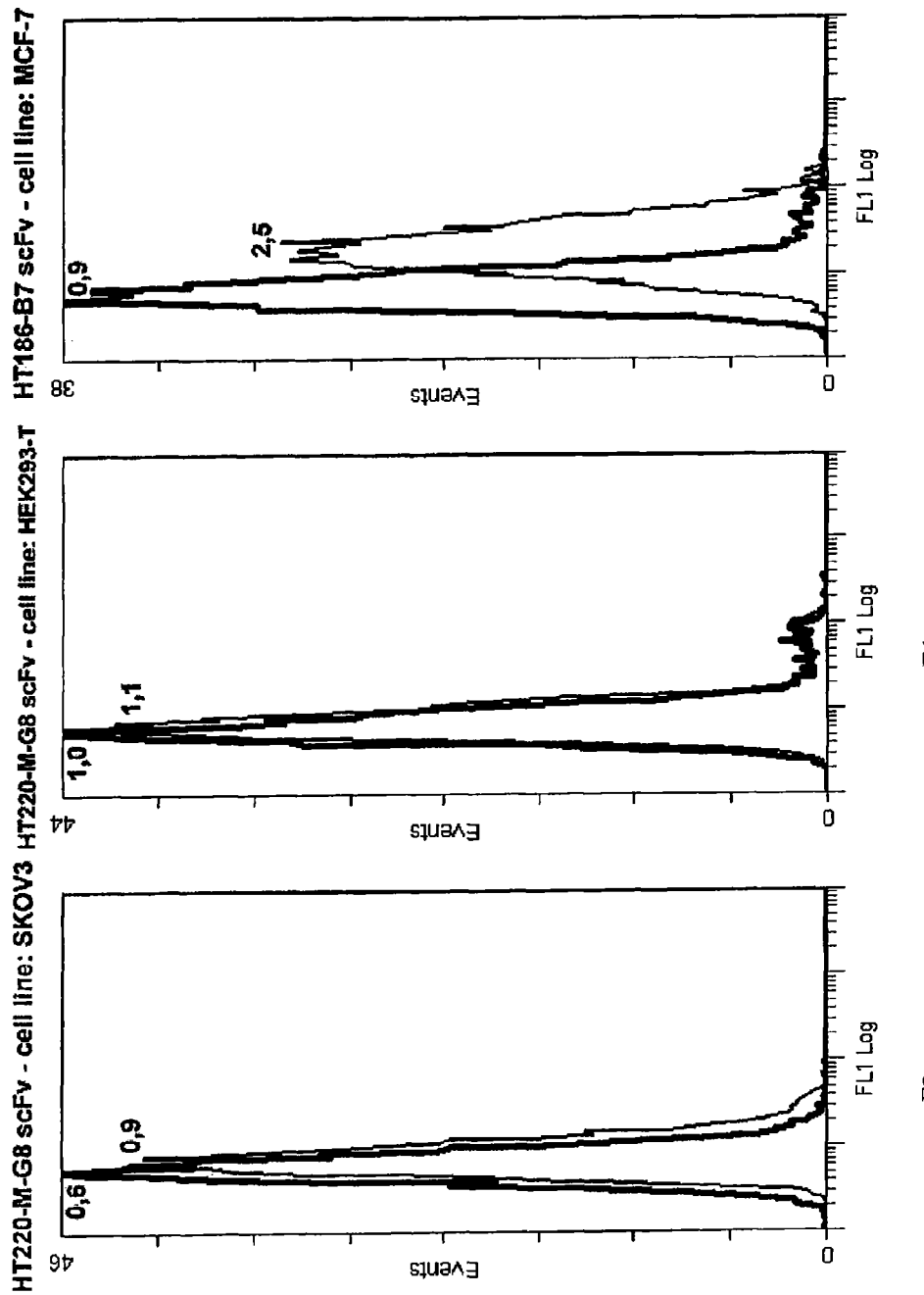
Figure 5H:
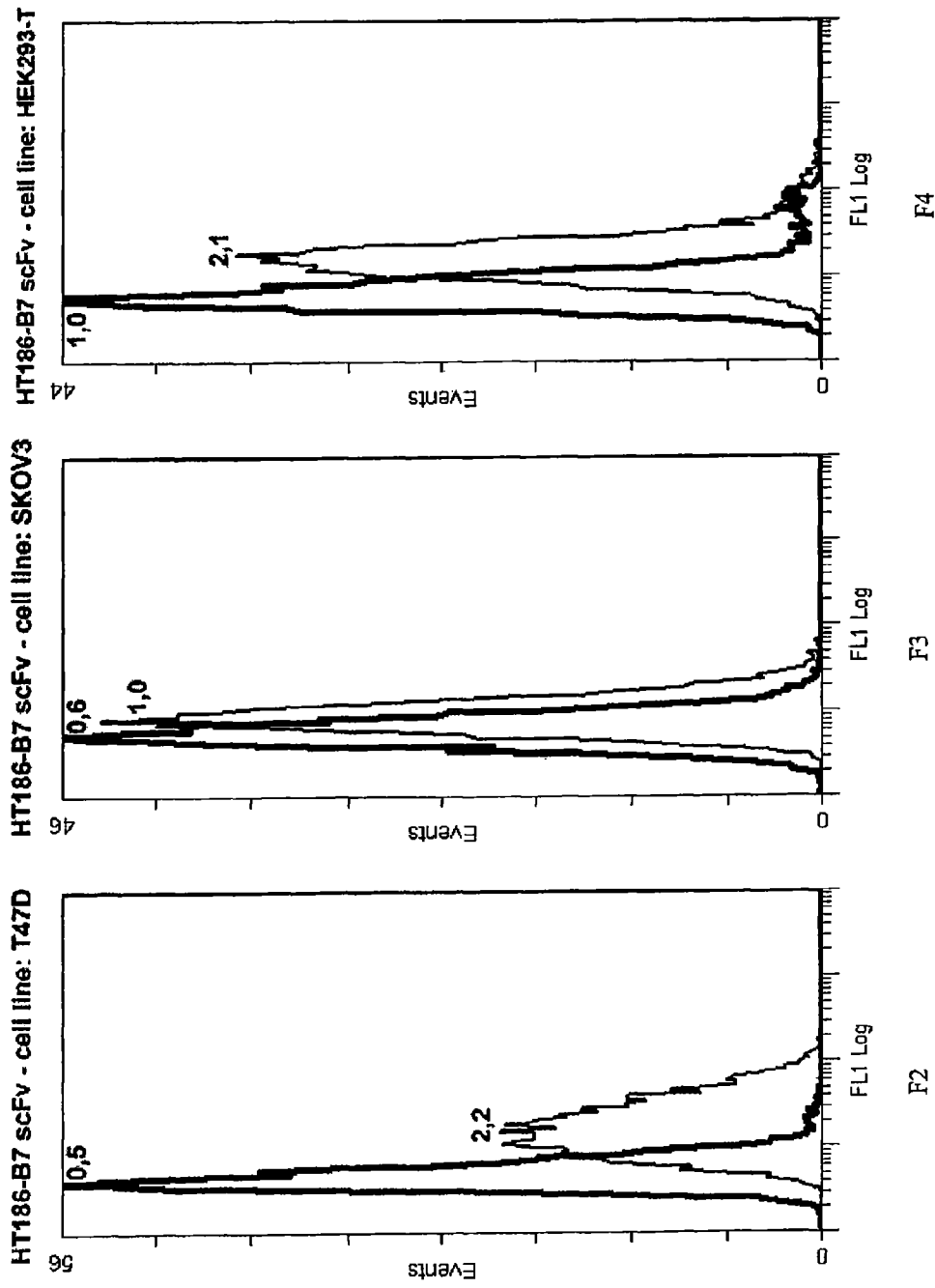
Figure 5I:
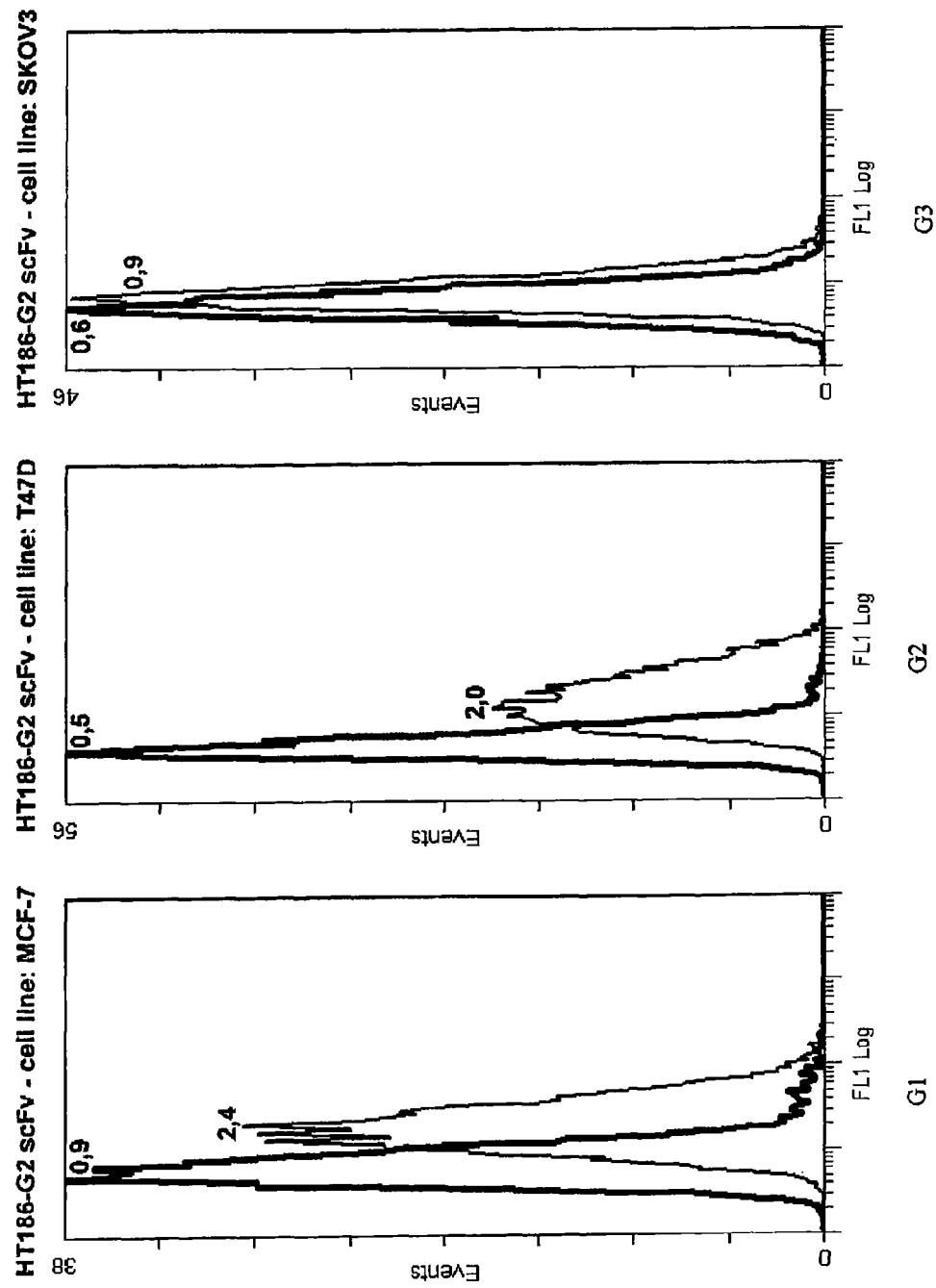
Figure 5J:
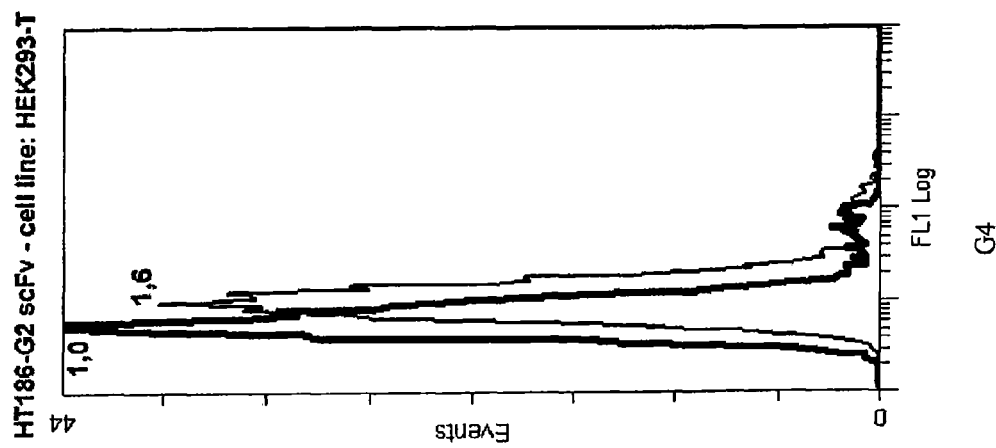

The surface plasmon resonance analyses shown in FIGS. 4 A) to F) are for antibody concentrations from 2 nM (lower curve), 5 nM, 10 nM, 20 nM, 40 nM, 60 nM, 80 nM, 100 nM to 200 nM (top curve) on immobilized 47 RU (resonance units) MUC1 peptide (15 aa+cystein, APDTRPAPGSTAPPAC) (SEQ ID NO: 115 with an additional cystein) on Chip 1. Analyses on 14 RU MUC1 peptide (15 aa+cystein, SEQ ID NO: 115 with an additional cystein) on Chip 2 gave similar values. Detailed results are given in the following table 2.

TABLE 2

MUC - peptide specific affinity of scFv antibodies from surface plasmon resonance measurement

| antibody | $k_a$ (1/Ms) | $k_d$ (1/s) | $R_{max}$, theor. | $K_A$ (1/M) | $K_D$ (M) | $\chi^2$ |
|---|---|---|---|---|---|---|
| Chip 1-47 RU MUC1-peptide (15aa Cys) | | | | | | |
| IIB6 | — | — | 41 | $3.2 \times 10^6$ | $3.1 \times 10^{-7}$ | 1.2 |
| HT186-D11 | $3.8 \times 10^4$ | $2.1 \times 10^{-5}$ | 519 | $1.8 \times 10^9$ | $5.7 \times 10^{-10}$ | 4.8 |
| HT200-3A-C1 | $4.9 \times 10^4$ | $1.0 \times 10^{-4}$ | 211 | $4.8 \times 10^8$ | $2.1 \times 10^{-9}$ | 4.3 |
| HT220-M-D1 | $2.9 \times 10^4$ | $1.1 \times 10^{-4}$ | 200 | $2.8 \times 10^8$ | $3.7 \times 10^{-9}$ | 2.3 |
| HT220-M-G8 | $5.0 \times 10^4$ | $2.2 \times 10^{-4}$ | 80 | $2.3 \times 10^8$ | $4.4 \times 10^{-9}$ | 1.5 |
| HT186-B7 | $3.5 \times 10^4$ | $4.6 \times 10^{-5}$ | 519 | $7.5 \times 10^8$ | $1.3 \times 10^{-9}$ | 7.0 |
| HT186-G2 | $7.2 \times 10^4$ | $7.2 \times 10^{-5}$ | 512 | $1.0 \times 10^9$ | $1.0 \times 10^{-9}$ | 36.7 |
| Chip 2-14 RU MUC1-peptide (15aa Cys) | | | | | | |
| HT186-D11 | $3.5 \times 10^4$ | $5.0 \times 10^{-5}$ | 53 | $1.5 \times 10^9$ | $6.5 \times 10^{-10}$ | 0.6 |
| HT186-B7 | $9.0 \times 10^4$ | $1.4 \times 10^{-4}$ | 62 | $6.3 \times 10^8$ | $1.6 \times 10^{-9}$ | 1.3 |
| HT186-G2 | $7.3 \times 10^4$ | $1.1 \times 10^{-4}$ | 82 | $6.6 \times 10^8$ | $1.5 \times 10^{-9}$ | 1.17 |

Alternatively, the antibodies of the invention could be expressed in animal cell culture from a suitable eukaryotic expression cassette containing the antibody encoding nucleic acid sequence.

Following collection of cells after induction of the bacterial promoter, periplasmic proteins were isolated and affinity purified by metal chelate chromatography using the His-tag of the antibodies. For comparative antibody IIB6 (anti-MUC1, according to Toleikis, loc. cit.) and for antibody according to the invention, the following production efficiencies were determined. A comparison of the yields of antibodies HT186-D11, HT200-3A-C1, HT220-M-D1, HT220-M-G8, HT186-B7, and HT186-G2, also scFv, show comparable production rates and yields.

From these results, it can be seen that the antibodies of the invention show a very high affinity to the specific antigen, with an approximate dissociation constant $K_D$ in the range of $2.1 \times 10^{-9}$ to $5.7 \times 10^{-10}$ M, which is a significantly higher affinity than that previously found for comparative antibody IIB6 having a $K_D$ of $3.1 \times 10^{-7}$.

Using immobilized synthetic overlapping peptides for association to the antibodies of the invention, it was found that the epitope recognised by the antibodies has the amino acid sequence RPAP, which is a section of the VNTR region of MUC1. It is assumed that the high affinity of the antibodies of the invention for MUC1 in the tumor-associated O-glycosylation over the non-tumor associated O-glycosylation of MUC1 is caused by the epitope being exposed in the tumor-associated O-glycosylation.

Using flow-cytometry (FACS) wherein the binding peptides of the invention were embodied as scFv fragments of approx. 200 000 cultivated human neoplastic cells (MUC1-positive human adenocarcinoma cell lines T47D and MFC-7, MUC1-positive ovarian carcinoma cell line SKOV3, and MUC1-negative HEK293-T), with immune staining by incubation with antibodies according to the invention, removal of unbound antibody by washing and specific detection by a secondary antibody-dye (mouse anti-His$_6$-IgG, combined with goat anti-mouse-IgG-FITC conjugate) and washing, MUC1 specific detection of cells by antibodies comprising the binding peptides of the invention could be analysed. From the FACS results, which due to the gate settings of the flow cytometer are shown in FIG. 5 for living cells only, it can be seen that the antibodies of the invention HT186-D11, HT200-3A-C1, HT220-M-D1, HT220-M-G8, HT186-B7, and HT186-G2 each have a high affinity to surface cell bound, tumor associated MUC1, whereas no significant or only very low non-specific reaction with the control cell line HEK293-T occurred. Comparative clone IIB6 showed a less selective association with MUC1.

Figure 6:
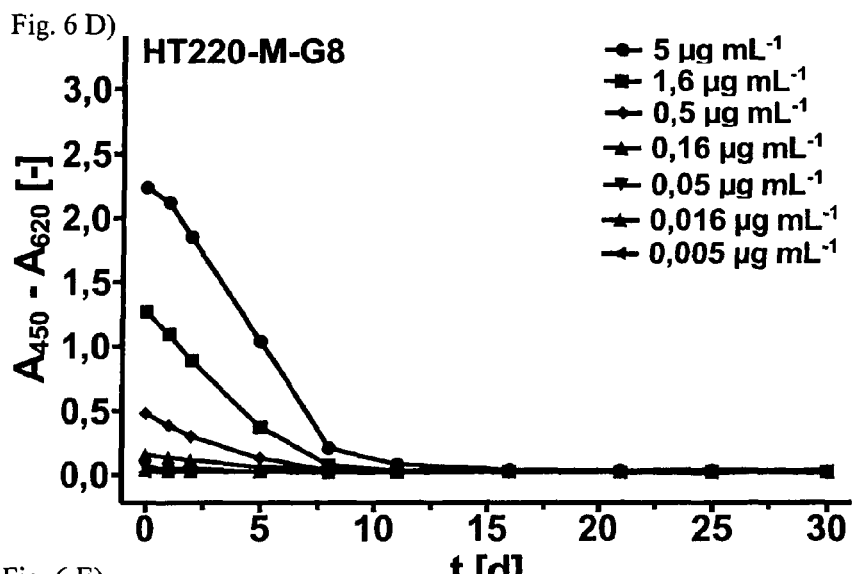
Figure 6:
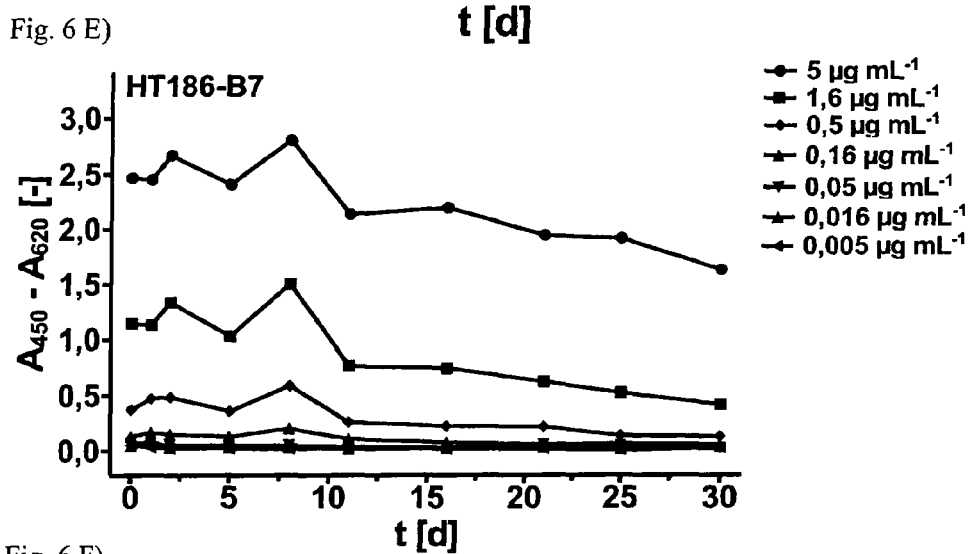
Figure 6:
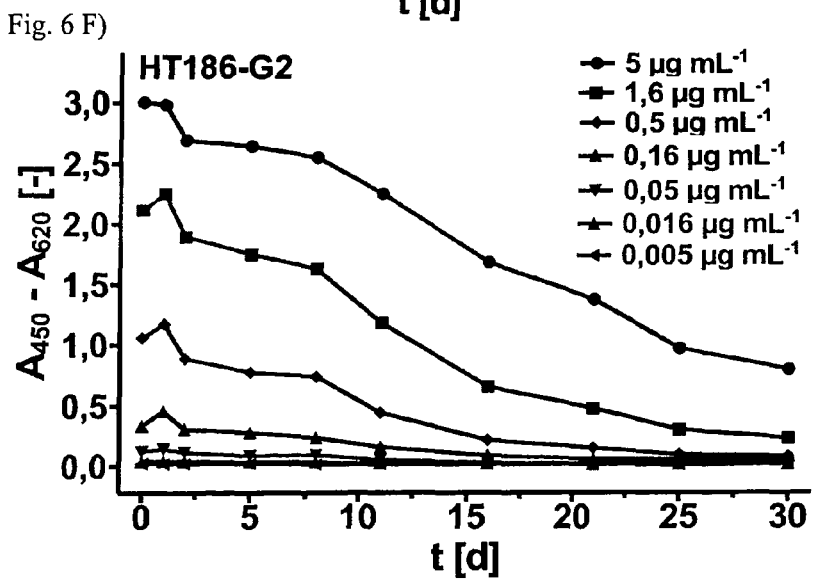

For the stability ELISA, the results of which are shown in FIGS. 6 A) to F), and G) for comparative IIB6, respectively, detection of bound scFv was by mouse anti-His-tag IgG, followed by goat anti-IgG HRP-conjugate, using colorimetric detection of HRP (horse radish peroxidase) with TMB. For negative controls, bovine serum albumin (BSA) was used as the antigen immobilized to the microtiter plate wells.

For stability testing, purified antibodies of the invention were incubated at a concentration of 10 μg/mL at 37° C., with measurement of the relative specificity for MUC1 antigen in an ELISA. Results are shown in FIG. 6, indicating that the antibodies of the invention have an improved long-term stability over a period of at least seven days, preferably of at least 30 days, at concentrations from 5 μg/mL (top curve), 1.6 μg/mL, 0.59 μg/mL, 0.16 μg/mL, 0.05 μg/mL, 0.016 μg/mL to 0.005 μg/mL (bottom curve) each, at least superior in relation to comparative antibodies generated during the panning procedure, for which results are shown under A) to F), and G) for comparative IIB6 of Toleikis.

The propensity for forming non-specific aggregates in solution was estimated by size exclusion chromatography on Sephadex (Superdex 200 10/300 GL, using 0.5 mL/min flow rate and UV detection. Results are shown in FIG. 7, indicating that the antibodies of the invention in comparison to comparative antibodies showed a significantly reduced proportion of dimers or higher aggregates.

Figure 7:
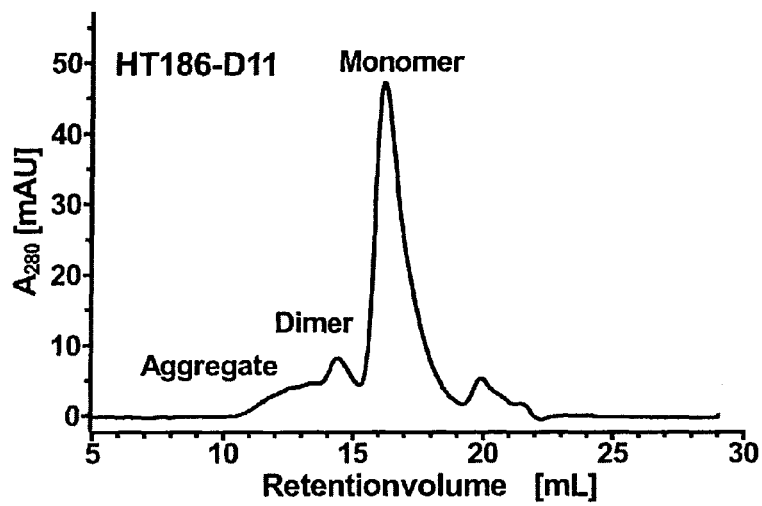
Figure 7:
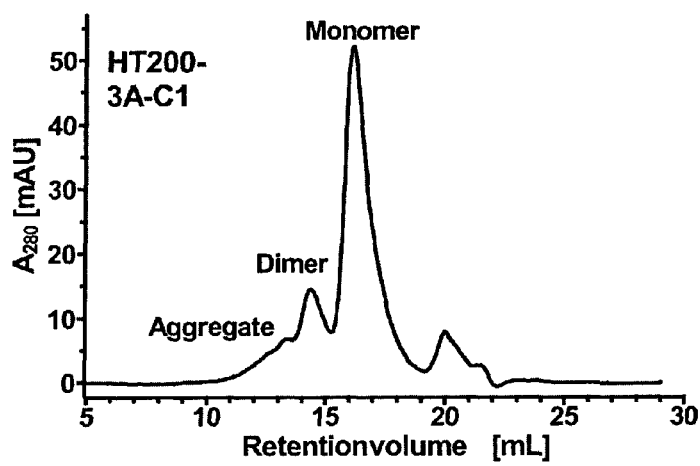
Figure 7:
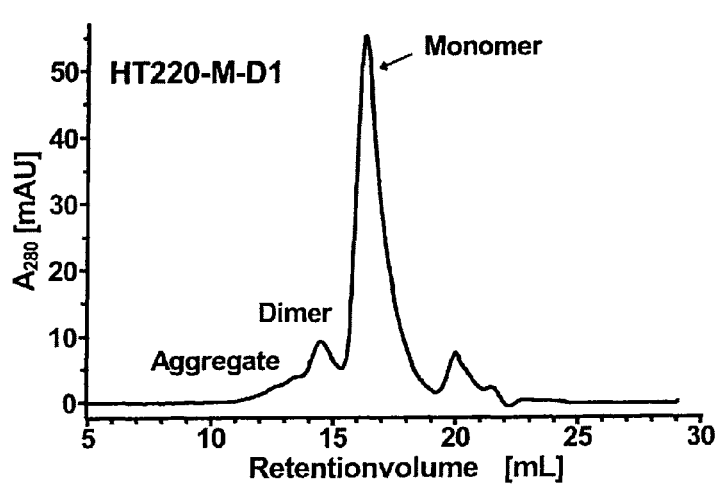
Figure 7:
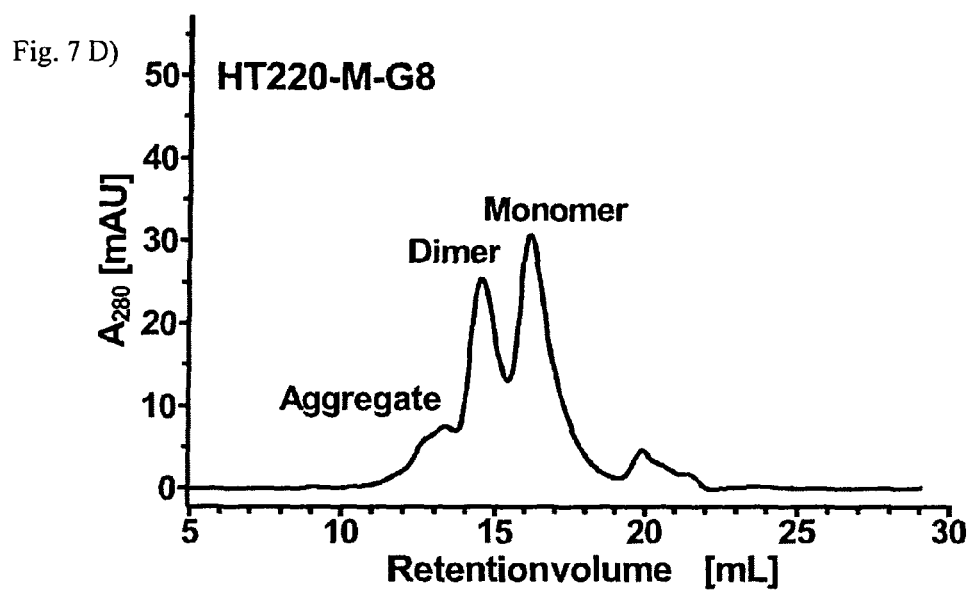
Figure 7:
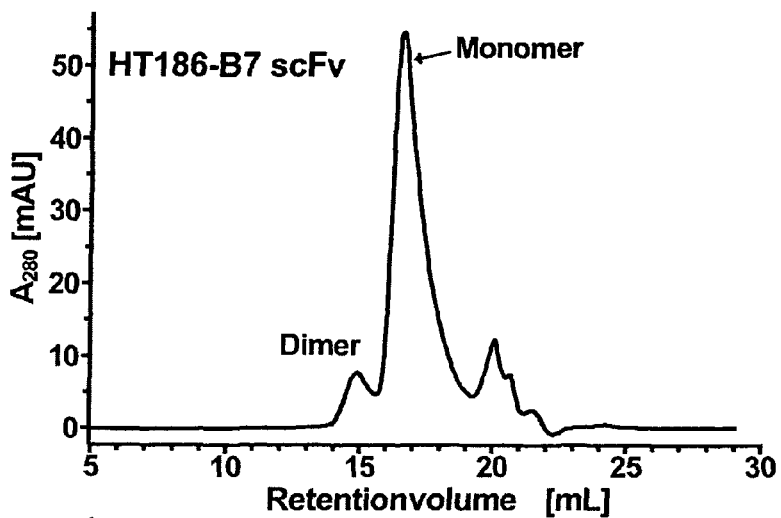
Figure 7:
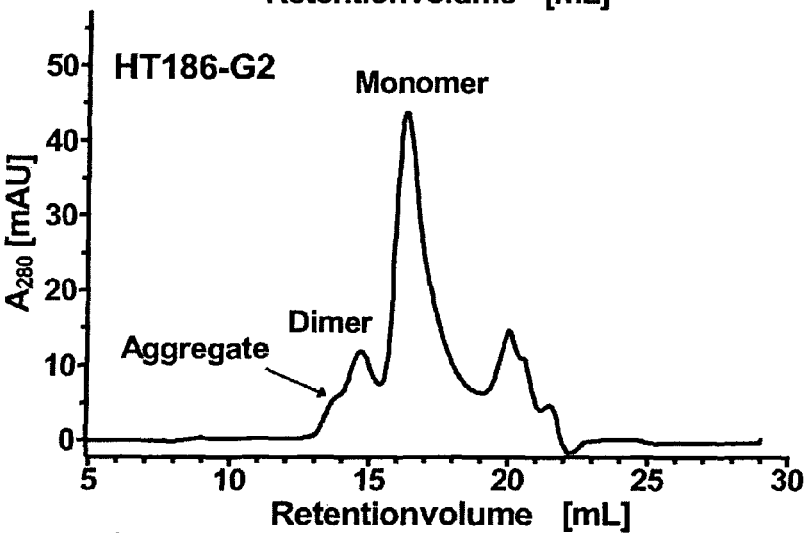
Figure 7:
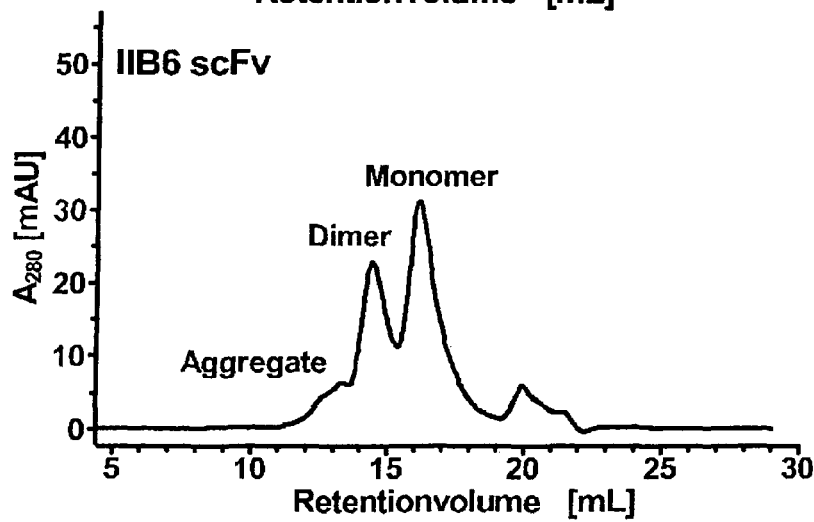

Results are shown in FIG. 7 A) to F) for antibodies of the invention, and in G) for the comparative antibody. From the higher proportion of monomer, and reduced proportion of aggregates in the antibodies of the invention when compared to G), it can be concluded that the antibodies of the invention better maintain their structure in solution and therefore an increased activity over storage and treatment periods can be expected. This result confirms the stability tests shown in FIGS. 6 A) to F).

EXAMPLE 1

Anti MUC-1 Antibodies Expressing YB2/0 Clones

Pools of transfected YB2/0 cells stably expressing one of the anti-MUC1 hHMFG1, D11, B7 and G2 were obtained.
At least 10 mg of each antibody was produced by batch agitated culture.

The above mentioned antibodies are possibly used for the treatment of some cancers, for instance lung cancer.

1—Cloning Procedures a—Cloning of λ Constant Light Chain (λ-CL)

The λ-CL chain was amplified by PCR from the vector CHL558-02, which has been digested by Apa I and Nhe I restriction enzymes to avoid contamination.

PCR was performed in a volume of 100 μL with the two following primers:

SEQ ID NO: 119
Primer forward 5'-tggctgcaccaagtgtcactc-3',

SEQ ID NO: 120
Primer reverse 5'-ccgggatcctctctagagttta-3'.

The components of the reaction are as follows:

| | |
|---|---|
| DNA template (CHL558-02 vector) 1 ng/mL | 1 μL |
| PCR reaction Buffer 5× | 20 μL |
| 40 mM dNTP (10 mM each) | 2 μL |
| Primer forward 10 pmol/μL | 5 μL |
| Primer reverse 10 pmol/μL | 5 μL |
| Phusion DNA polymerase (4 U/μL) | 1 μL |
| water | 66 μL |

The reaction was carried out according to the following program

| | |
|---|---|
| 98° C.; 30 s | |
| 98° C.; 10 s | |
| 50° C.; 20 s | ×29 |
| 72° C.; 15 s | |
| 72° C.; 10 min | |

4° C.; 5 min and 16° C.; ∞.

After PCR, the expected band of 339 base pairs (bp) was obtained.

PCR fragment was purified with NucleoSpin® Extract II Kit (Macherey Nagel), and resuspended in 75 μL of Elution buffer.

Purified PCR fragment was:

First, digested with Dra III restriction enzyme, and purified with NucleoSpin® purification kit, and Second, digested with Xba I restriction enzyme, and purified with NucleoSpin® purification kit.

In the same time, the target vector was simultaneously digested with Dra III and Xba I, digestions followed by dephosphorylation of the 5'end by using Shrimp Alcaline Phosphatase (SAP). Vector was purified on agarose gel and with NucleoSpin® Extract II Kit (Macherey Nagel).

Double digested PCR fragment and vector were then ligated by using T4 DNA ligase (1.5 U) in a respective ratio 3:1 and 10:1. As control, vector alone has been treated with T4 DNA ligase.

After incubation (o/n at 16° C.), T4 DNA ligase was inactivated at 65° C. for 15 min.

Ligation products (Vector insert 1:3 and 1:10, and vector alone) were desalted by ethanol precipitation and resuspended in 40 μL of water.

*E. coli* XL1-Blue MRF' electrocompetent bacteria were then transformed by electroporation (1.7 kV) with ¼ of one of the ligation products. Immediately after electroporation, cells were resuspended in SOC medium and incubated for 1 h at 37° C. and plated on 2× YT agar plates containing ampicillin. Plates were incubated o/n at 37° C.

On the plates where bacteria transformed with vector alone were plated, 15 colonies have emerged.

On the plates where bacteria transformed with vector+insert 1:3 were plated, about 50 colonies have emerged (A).

On the plates where bacteria transformed with vector+insert 1:10 were plated, about 100 colonies have emerged (B).

14 colonies from (A) and 14 colonies from (B) were tested by PCR using the following primers:

```
                                        SEQ ID NO: 119
Primer forward    5'-tggctgcaccaagtgtcactc-3', SEQ ID NO: 121
Primer reverse Seq 5'-gggaggggcaaacaacagatggc-3'.
```

The components of the reaction are as follows:

| | |
|---|---|
| Bacteria in medium | 1 μL |
| PCR reaction Buffer 10× | 2 μL |
| 40 mM dNTP (10 mM each) | 1 μL |
| Primer forward 10 pmol/μL | 0.2 μL |
| Primer reverse 10 pmol/μL | 0.2 μL |
| RED DNA Taq polymerase (4 U/μL) | 0.3 μL |
| water | 16.3 μL |

The reaction was carried out according to the following program

| | |
|---|---|
| 95° C.; 100 s | |
| 95° C.; 60 s | |
| 52° C.; 45 s | ×29 |
| 72° C.; 45 s | |
| 72° C.; 10 min | |
| 4° C.; 5 min and 16° C.; ∞. | |

After separation on 1% agarose gel, all the 28 colonies tested were positive.

4 clones were amplified to prepare maxi DNA preparations, and, said maxi preparations were sequenced by using Primer reverse Seq 5'-gggaggggcaaacaacagatggc-3' SEQ ID NO: 121.

No mutation was found. The HT327-11 clone was chosen.

b—General Cloning Strategy

For cloning of anti-MUC1 variable domains the IgG expression vector CHK622-08 (optimized for expression of human IgG1 antibodies) was modified. The light chain kappa constant gene was replaced with the light chain lambda constant gene provided in the vector CHL558-02 as described in section a-Cloning of λ constant light chain (λ-CL).

Anti-MUC1 scFv variable domains were bioinformatically analyzed by using the VBASE2 portal (http://www.vbase2.org).

Synthetic genes of VH and VL genes of the clones HT186-D11, HT186-B7 and HT186-G2 (including the desired restriction sites and the human signal sequence of the corresponding human germline genes) were ordered at Genscript (GenScript USA Inc. 120 Centennial Ave. Piscataway, N.J. 08854 USA). The genes were provided in a pUC57 vector.

The synthetic variable domain genes then were cloned in a two step cloning. First the VL gene of each variant (HT186-D11, B7, G2) was cloned into the vector CHK622-08 lambda using SpeI and DraIII restriction sites. Subsequently the VH genes of HT186-D11, B7, G2 were cloned into the vectors of the light chain gene cloning using NheI and ApaI restriction sites. After cloning, DNA sequencing of all vector areas affected by cloning was performed to validate the success of cloning.

The following clones were finally created:
HT335-1-1→Vector: CHK622-08→lambda encoding: HT186-D11 IgG.
HT335-3-2→Vector: CHK622-08→lambda encoding: HT186-G2 IgG.
HT337-1-2→Vector: CHK622-08→lambda encoding: HT186-B7 IgG.

2—Cell Transfection Procedure 2.2.1 Host Cell Line of Transformation

The host cell line of transformation, intended to integrate the expression vector and produce the antibody, is the line YB2/0.

YB2/0 cells were received defrosted. They were kept in view of transfections at $2.10^5$ cells/mL in EMS medium, 5% dialyzed FBS (table 1).

TABLE 1

| Monitoring of the YB2/0 line before transfection | | |
|---|---|---|
| Cell density ($10^5$ c/mL) | Viability (%) | ~~Transplanting~~ cell density ($10^5$ c/mL) |
| 14.4 | 96 | 1 |
| 11 | 91 | 2 |
| 2.8 | 93 | Centrifuged volume: 200 mL |

2.2.2 Expression Vectors

The expression vectors used for transfection are listed in table 2.

TABLE 2

| Vectors used for transfection | |
|---|---|
| Vector | Concentration |
| HT186-B7 linearized by EcoRV | 1,365 ng/mL |
| HT186-D11 linearized by EcoRV | 1,456 ng/mL |
| huHMFG1 linearized by NotI | 1,533 ng/mL |
| HT186-G2 linearized by EcoRV | 1,289 ng/mL |
| H416-24 (T+) | 1,000 ng/mL |
| K416-23 (T+) | 1,000 ng/mL |

3. Results 3.1 Electroporation and Transfection Rates

Electroporation was carried out as follows:
voltage 230V
capacitance 960 μF
Six cuvettes were prepared:
Cuvette 1: 42.7 μg of the vector HT186-B7 linearized by EcoRV
Cuvette 2: 42.7 μg of the vector HT186-D11 linearized by EcoRV
Cuvette 3: 42.7 μg of the vector huHMFG1 linearized by NotI
Cuvette 4: 42.7 μg of the vector HT186-G2 linearized by EcoRV
Positive control cuvette:
  25.2 μg is of the linearized vector H416-24
  23.2 μg of the linearized vector K416-23
Negative control cuvette: no vector
After electroporation, cells were distributed from the electroporation cuvettes to cell culture plates as follows:

Cuvette 1 to 4 (per cuvette):
  5 P24 at 25,000 cells/well
  1 P96 at 500 cells/well
  1 P96 at 100 cells/well
Positive control cuvette T+:
  1 P96 at 5,000 cells/well
  1 P96 at 500 cells/well
  1 P96 at 100 cells/well
Negative control cuvette T−:
  1 P96 at 5,000 cells/well
  1 P96 at 500 cells/well
  1 P96 at 100 cells/well
The characteristics of the transfection are listed in table 3.

TABLE 3

Characteristics of the transfection

| Cuvette No. | Pulse time (in ms) | Recommendation | Plate | J + 3 counting Living cells ($\times 10^5$/mL) | Recommendation P24 |
|---|---|---|---|---|---|
| T− | 17.8 | To be between | P96 at 25,000 cells/mL | 2.11 | >2 |
| T+ | 17.6 | 17 and 21 ms | P96 at 25,000 cells/mL | 0.91 | >0.8 |
| 1 | 17.8 | | P24 at 25,000 cells/mL | 0.83 | >0.8 |
| 2 | 18.1 | | P24 at 25,000 cells/mL | ND | >0.8 |
| 3 | 17.9 | | P24 at 25,000 cells/mL | ND | |
| 4 | 17.9 | | P24 at 25,000 cells/mL | ND | |

Cells were kept in a selective medium: RPMI medium, 5% dialyzed FBS, 0.5 g/L, geneticine, 25 nM MTX for P24 and P96 plates at 5,000 cells/well and RPMI, 5% dialyzed FBS, 1 g/L geneticin for the others in order to determine transfection rates. The medium was renewed every 7 days during 4 weeks for P96 plates and up to the establishment of pools for P24 plates.

Appearance rates of the transformants are shown in table 4.

3.2 Establishment and Freezing of Pools

The first pool of each cuvette is achieved at J+16 and the second one at J+19. These pools are titrated by ELISA (table 5).

TABLE 5

Establishment and titration of pools

| Date | Cuvette | Pool | Number of cells ($\times 10^6$) | Viability (%) | Titer (μg/mL) | Difference (%) |
|---|---|---|---|---|---|---|
| Dec. 12, 2008 | 1 | 1 | 0.6 | 71 | 3.3 | |
| | 2 | 1 | 0.54 | 84 | 4.7 | |
| | 3 | 1 | 0.5 | 86 | 3.9 | |
| | 4 | 1 | 0.56 | 80 | 4 | |

TABLE 5-continued

Establishment and titration of pools

| Date | Cuvette | Pool | Number of cells ($\times 10^6$) | Viability (%) | Titer (μg/mL) | Difference (%) |
|---|---|---|---|---|---|---|
| Dec. 15, 2008 | 1 | 2 | 0.38 | 59 | 4.9 | 33 |
| | 2 | 2 | 0.42 | 64 | 5.6 | 17 |

TABLE 4

Appearance rates of transformants in 96-well plates

| Cuvette No. | Selection | Cells/well | Number of P96 | Number of grown wells/P96 | Theoretical number of grown wells/P96 | Transfection in accordance | Transfection rates |
|---|---|---|---|---|---|---|---|
| 1 | RPMI + 5% dialyzed FBS + G418 1 g/L | 100 | 1 | 5 | 5 | Not applicable | 1/1870 |
| 1 | RPMI + 5% dialyzed FBS + G418 1 g/L | 500 | 1 | 27 | 27 | Not applicable | 1/1515 |
| 2 | RPMI + 5% dialyzed FBS + G418 1 g/L | 100 | 1 | 10 | 10 | Not applicable | 1/910 |
| 2 | RPMI + 5% dialyzed FBS + G418 1 g/L | 500 | 1 | 34 | 34 | Not applicable | 1/1144 |
| 3 | RPMI + 5% dialyzed FBS + G418 1 g/L | 100 | 1 | 6 | 6 | Not applicable | 1/1550 |
| 3 | RPMI + 5% dialyzed FBS + G418 1 g/L | 500 | 1 | 13 | 13 | Not applicable | 1/3437 |
| 4 | RPMI + 5% dialyzed FBS + G418 1 g/L | 100 | 1 | 9 | 9 | Not applicable | 1/1016 |
| 4 | RPMI + 5% dialyzed FBS + G418 1 g/L | 500 | 1 | 22 | 22 | Not applicable | 1/1921 |
| T+ | RPMI + 5% dialyzed FBS + G418 1 g/L | 100 | 1 | 10 | 10 | Yes | 1/910 |
| T+ | RPMI + 5% dialyzed FBS + G418 1 g/L | 500 | 1 | 34 | 34 | Yes | 1/1144 |

TABLE 5-continued

Establishment and titration of pools

| Date | Cuvette | Pool | Number of cells (×10⁶) | Viability (%) | Titer (µg/mL) | Difference (%) |
|---|---|---|---|---|---|---|
| | 3 | 2 | 0.48 | 63 | 6.3 | 39 |
| | 4 | 2 | 0.50 | 62 | 6 | 34 |

Pool No. 2 of each cuvette was amplified in RPMI medium, 5% dialyzed FBS, 0.5 g/L geneticine, 25 mM MTX for conservation. Two CryoTubes were done for each pool. Data about freezing are shown in table 6. A PCR-based Mycoplasma detection test was conducted on each sample on the day of freezing. Cells are free of Mycoplasma contamination.

TABLE 6

Conservation of pools

| Pool | Viability (%) | Number of cells (×10⁶) | Number of CryoTubes |
|---|---|---|---|
| Cuvette 1 | 85 | 5 | 2 |
| Cuvette 2 | 90 | 5 | 2 |
| Cuvette 3 | 93 | 5 | 2 |
| Cuvette 4 | 93 | 5 | 2 |

3.3 Production in Roller Culture

Quantities to be produced for each cuvette are shown in table 7.

TABLE 7

Quantities to be produced for each antibody

| Cuvette No. | Human IgG titration of transfectant pools (µg/mL) in EMS | Ab quantity (mg) required for experiments | Ab quantity to be produced (mg) | Number of roller bottles (900 mL each) |
|---|---|---|---|---|
| Cuvette 1 | 4.3 | 10 | 15 | 4 |
| Cuvette 2 | 6.4 | 120 | 140 | 24 |
| Cuvette 3 | 8.5 | 60 | 80 | 10 |
| Cuvette 4 | 5.6 | 10 | 15 | 3 |

The roller cultures were carried out in EMS medium, 5% FBS depleted of bovine Igs, 0.5 g/L geneticine.

The supernatants were titrated by ELISA at the end of the roller culture production (table 9).

TABLE 9

Titration of the supernatants of the roller cultures

| Sample | Concentration (µg/mL) | Produced quantity (mg) |
|---|---|---|
| Cuvette 1 | 3.4 | 12.2 |
| Cuvette 2 | 9.8 | 211.7 |
| Cuvette 3 | 10 | 90 |
| Cuvette 4 | 6.1 | 16.5 |

The supernatants were concentrated by tangential ultrafiltration on Proflux (Millipore), filtered through a 0.22 µm filter. The recovered volumes after concentration are shown in table 10.

TABLE 10

Production volumes of the roller cultures

| Sample | Produced volume (mL) | Concentrated volume (mL) |
|---|---|---|
| Cuvette 1 | 3,600 | 619 |
| Cuvette 2 | 21,600 | 1,764 |
| Cuvette 3 | 9,000 | 621 |
| Cuvette 4 | 2,700 | 621 |

EXAMPLE 2

Anti MUC-1 Production

The anti-MUC1 antibodies, which are contained in supernatants of the YB2/0 cell line production, were purified by gel affinity chromatography on Sepharose-protein A and then characterized.

The purification yields of the R764-hHMFG1 and R764-D11 antibodies, on a column that contains 5 mL of gel, are respectively of 74 and 73%.

The purification yields of the two other antibodies R764-B7 and R764-G2, on a column that contains 1 mL of gel, are respectively of 31 and 75%.

Materials and Methods

1 Material 2.1.1 Supernatants of Production

R764-722 08/017 cuvette 3; vector huHMFG1; volume: 3 liters

R746-722 08/017 cuvette 2; vector HT186-D11; volume: 22 liters

R764-722 08/017 cuvette 1; vector HT186-B7; volume: 9 liters

R764-722 08/017 cuvette 4; vector HT186-G2; volume: 3 liters

Production medium: EMS+5% FBS depleted of bovine IgGs+1 g/L G418.

2.1.2 Chromatography Columns

HiTrap™ rProtein A FF 5 ml (GE Healthcare, 17-5080-01, Lot No. 10010319)

HiTrap™ rProtein A FF 1 ml (GE Healthcare, 17-5079-01, Lot No. 10008107)

2 Methods 2.1 IgG1 Anti-MUC1 Purification by Affinity Chromatography

After equilibration by addition of 10 column volumes of buffer A1 (Tris 25 mM, NaCl 25 mM, EDTA 5 mM, pH 7.10), the supernatant of culture is injected onto the Sepharose-protein A column. Afterwards the said column is washed by 15 volumes of buffer A1 and the retained antibodies in the Sepharose-rprotein A gel are eluted by injection of the buffer B1 (Sodium citrate 25 mM, pH 3.6). The eluted fractions from the 1 and 5 mL HiTrap columns are respectively of 1 and 3 mL, and are collected in tubes containing $\frac{1}{10}^{th}$ of the volume of the Tris 2M pH 7.5 fraction.

After elution, the Sepharose-rprotein A columns are regenerated by injection of a 0.1M phosphoric acid solution during 3 minutes and then re-equilibrated with buffer A1.

For the 5 mL HiTrap column, flow rates of equilibration, injection and washing are of 5 mL/min and the elution flow rate is of 2.5 mL/min. For the 1 mL HiTrap column, the flow rate is of 0.5 mL/min except for the last 10 volumes of the washing step, for which the said flow rate of equilibration is increased to 1 mL/min.

The eluted fractions containing the antibody are pooled and dialyzed at 4° C. against PBS (Sigma, P-4417) during one night. Then the eluate is filtered through a syringe filter, which has a porosity of 0.2 nm.

2.2 Characterization Methods

Titration of Human IgGs: FastELYSA (RD biotech kit) O.D. (280 nm): the M.O. 403-0411/2

SDS-PAGE electrophoresis: the M.O. 613-202/1

SDS-CGE: IGG purity kit according to the protocol given by the manufacturer

Molecular weight distribution by gel filtration: the M.O. 643-0205

Fucose titration: the M.O. 613-331/1 and 613-207/1. Fucose titration by ELISA-AAL Results and Comments 1 Purification of the Antibodies The supernatants of production were concentrated about 15 times by tangential ultrafiltration before purification. The rates of antibodies contained in the concentrated supernatants of production and in the dialyzed and filtered elations were titrated by the FastELYSA technique in the same test, in order to evaluate the purification yields.

The IgGs contained in the supernatants of production of the R764-hHMFG1 and R764-D11 clones were purified by chromatography on a 5 mL column, while the IgGs from the R764-B7 and R764-G2 clones were purified on a 1 mL column. The yields of purification of the antibodies are about 74%, except for the R764-B7 antibody which has a yield of purification of 31% (Table I). The value of the yield of purification for the R764-B7 clone can be explained by the fact that, after elution and dialysis, the solution was very cloudy which required a centrifugal step before filtration. After this filtration step, the solution stored in a tube at 4° C. got cloudy again.

TABLE I

Anti-MUC1 antibodies yields of purification

| Purification No. | Clone name | Supernatant of culture | | Purified antibodies | | Yield (%) |
|---|---|---|---|---|---|---|
| | | Vol. (mL) | IgG (mg) | Vol. (mL) | IgG (mg) | |
| 632-09/143 | R764-hHMFG1 | 597 | 86.5 | 24.8 | 63.6 | 74 |
| 632-09/144 | R764-D11 | 1,700 | 204 | 65 | 149 | 73 |
| 632-09/145 | R764-B7 | 601 | 12 | 5 | 3.8 | 31 |
| 632-09/146 | R764-G2 | 605 | 16 | 5.6 | 12 | 75 |

The preparations of antibodies to be injected into the animal for in vivo tests were titrated for endotoxins by the microbiology control laboratory. The quantities of endotoxins existing in the preparations of antibodies R764-hHMFG1 and R764-D11 are respectively of 5 IU/mL and <1.5 IU/mL.

3 Purified Anti-MUC1 Antibodies Characterization 3.1 Electrophoretic Control

The anti-MUC1 antibodies were electrophoresed through a polyacrylamide gel in order to determine on the one hand, their purity and on the other hand, their apparent molecular weight ($MW_{app}$).

Figure 8:
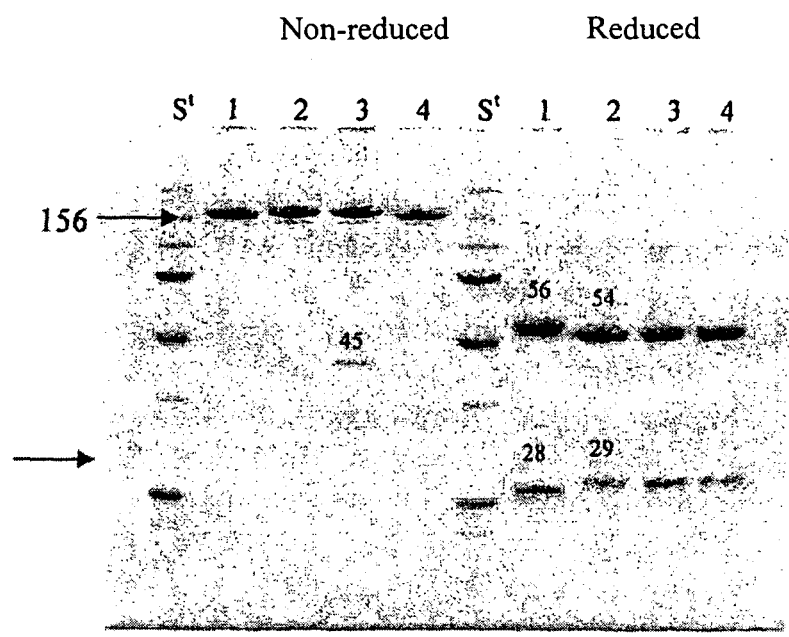
FIG. 8 represents a SDS-PAGE Coomassie blue-stained gel under reduced and non reduced conditions. St: protein ladder; 1 R764-hHMFG1, 2: R764-D11, 3: R764-B7, and 4: R764-G2.

Under non-reducing conditions, the electrophoretic profile of the anti-MUC1 IgGs reveals a band that is in the majority, equal to 156 kDa and corresponding to the entire IgG (2H2L). The R764-D11 and R764-G2 antibodies (lanes No. 2 and 4) also show 3 minor bands of $MW_{app}$ values: 143, 114 and 80 kDa. The electrophoretic profile of the R764-B7 antibody (lane 3) is made up of 6 bands in addition to the band that is in the majority, and equal to 156 kDa (FIG. 8).

Under reducing conditions, the electrophoretic profile of the antibodies reveals 2 major bands, corresponding to the heavy chain (HC) and to the light chain (LC). The R764-B7 antibody shows in addition a double band of low intensity and of $MW_{app}$ equal to 36 and 37 kDa.

The $MW_{app}$ of the heavy and light chains of the R764-hHMFG1 antibody differ significantly from those of the other anti-MUC1 antibodies: 56 vs. 54 for the heavy chain, and 28 vs. 29 for the light chain. The R764-hHMFG1 antibody is an IgG1, kappa, while the 3 other antibodies are of isotype IgG1, lambda. In addition, the R764-hHMFG1 antibody has a very different primary structure compared to the 3 other antibodies, which differ only by 5 to 6 amino acids per chain.

3.2 SDS-Page

In order to establish the relative proportions of the different antibody forms existing in the preparations, an analysis by capillary electrophoresis is done under non-reducing and reducing conditions.

In non-reducing conditions, the anti-MUC1 antibodies show percentages of entire IgGs (2H2L) that are between 62.5 and 79.2%. The quantity of the form 2H1L is smaller in the R764-hHMFG1 antibody preparation than in other preparations where it represents about 15 to 18% of the total forms.

TABLE II

Percentages of the different forms of the IgG molecule existing in the purified preparations of antibodies

| Sample | Antibody | IgG | 2H1L | HH | HC | LC | UD* |
|---|---|---|---|---|---|---|---|
| 632-09/143 | R764-hHMFG1 | 79.2 | 3.2 | — | | 0.8 | — |
| 632-09/144 | R764-D11 | 70.3 | 16.2 | 4.3 | — | 2.6 | 7.6 |
| 632-09/145 | R764-B7 | 62.5 | 14.7 | 4.3 | 8.3 | 6.3 | 7.9 |
| 632-09/146 | R764-G2 | 69 | 18 | 4.5 | 0.5 | 2.1 | 5.0 |

*UD: undetermined peak

After action of a reducing agent, the heavy chains (HC) and light chains (LC) of the antibodies are separated by capillary electrophoresis. This method allows detecting and establishing the percentage of non-glycosylated heavy chain (NG-HC).

The NG-HC quantity existing in the antibodies produced by the YB2/0 cell line is generally <1%, like in the 3 other anti-MUC1 antibodies: R764-D11, R764-B7, and R764-G2. On the other hand, the R764-hHMFG1 antibody contains a rate of non-glycosylated heavy chain that is about 5.4%, which is 10 times superior to the rate of the other anti-MUC1 antibodies.

TABLE III

Percentages of non-glycosylated chains of IgGs existing in the preparations of antibodies after reduction

| Antibody | LC | HC | NG-HC# | UD* |
|---|---|---|---|---|
| R764-hHMFG1 | 40.6 | 54 | 5.4 | — |
| R764-D11 | 33.8 | 62.3 | 0.4 | 3.5 |
| R764-B7 | 40.4 | 57.5 | — | 2 |
| R764-G2 | 35.7 | 63.9 | 0.5 | — |

NG-HC: non-glycosylated heavy chain;
*UD: undetermined peak

3.3 Molecular Weight Determination

The chromatograms obtained after injection of the purified anti-MUC1 IgG preparations on the gel filtration column show a peak that is in the majority, with a retention time of 32.5 min (±0.5 min). This retention time corresponds to the monomer of the human IgG1. Minor peaks with retention times of 27.3 (±0.3) and 21.8 (±0.4) minutes also exist; these peaks correspond to dimers and multimers of human IgG1s respectively.

TABLE IV

Percentages of isomers of anti-MUC1 antibodies

| Purification No. | Antibody | Multimer | Dimer | Monomer |
|---|---|---|---|---|
| 632-09/143 | R764-hHMFG1 | 0.55 | 3.13 | 96.31 |
| 632-09/144 | R764-D 11 | 0.89 | 1.67 | 97.44 |
| 632-09/145 | R764-B7 | 3.56 | 0.51 | 95.93 |
| 632-09/146 | R764-G2 | — | 0.99 | 99.01 |

The results of Table IV show that the 4 anti-MUC1 antibodies have a rate of monomer that is superior to 95%.

3.4 Fucose Titration

The titers of the $\alpha(1\text{-}6)$ linked fucose are determined by the lectin ELISA method. The results shown in Table V indicate that the 3 antibodies R764-D11, R764-B7 and R764-G2 have similar fucose rates, close to 30%. On the other side, the R764-hHMFG1 control antibody has a fucosylation rate that is 2.5 times superior.

TABLE V $\alpha(1\text{-}6)$ linked Fucose rates determined by the lectin ELISA method

| Antibody | 779-09/038 | 779-09/039 | 779-09/043 | 779-09/044 | Average ± SD |
|---|---|---|---|---|---|
| R764-hHMFGI | 80.7 | — | — | 82 | 81 (± 0.9) |
| R764-D 11 | — | — | 28.2 | 25.2 | 27 (± 2.1) |
| R764-B7 | 33 | 27.0 | 29.7 | 28.3 | 29 (± 2.6) |
| R764-G2 | — | 26.0 | 32.1 | 26.8 | 28 (± 3.3) |

3.3.5 Antigenic Recognition by ELISA Test

Figure 9:
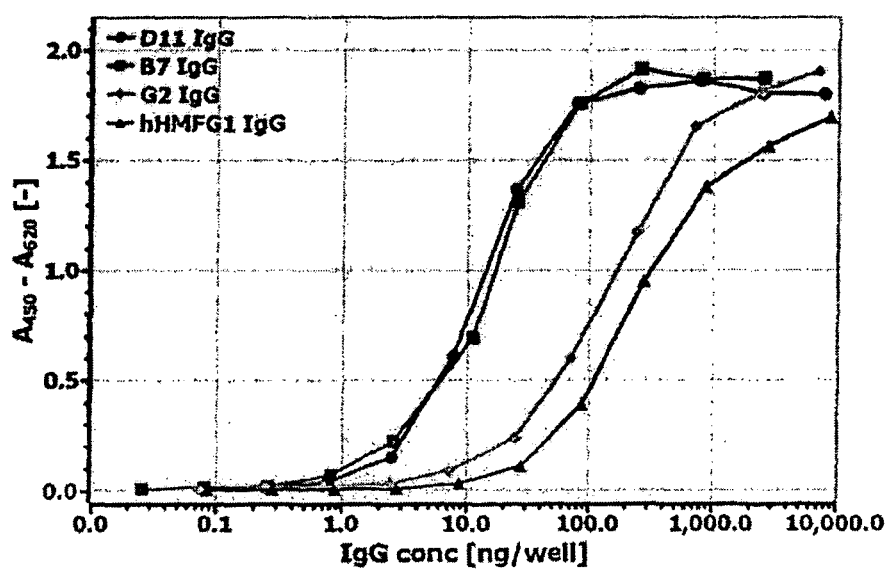
FIG. 9 represents anti-MUC1 IgG binding curve to the insoluble antigen in the microtitration plate. It corresponds to preliminary results.

This analysis was done using the ELISA technique wherein the 32-mer MUC1 peptide is immobilized in the wells of a microtitre plate, and wherein the anti-MUC1 antibodies are added later in different concentrations. The fixed antibodies are revealed and the O.D. values are reported to a graph on the Y-axis, while the antibody quantities are reported on the X-axis (FIG. 9).

CONCLUSION

The 4 anti-MUC1 antibodies were purified by gel affinity chromatography on Sepharose-protein A. Because of the different quantities of antibodies to be purified, it was necessary to adapt the size of each affinity column. The R764-hHMFG1 and R764-D11 antibodies were purified on a 5 mL gel column, and their yields of purification are of 74 and 73% respectively. The 2 other antibodies, R764-B7 and R764-G2 were purified on a 1 mL gel column, and their yields of purification are 33 and 75% respectively. The poor yield of purification of the R764-B7 antibody can be explained by the existence of a precipitate after the dialysis step, which required a centrifugal step before filtration.

The analysis of the antibodies by CGE or PAGE electrophoresis, under non-reducing conditions, show that the R764-hHMFG1 which is of isotype IgG1, kappa is less sensible to light chain dissociation than the 3 other antibodies that are of isotype IgG1, lambda. However, if one refers to the chromatography results of molecular weight distribution, it appears that the 4 antibodies have a similar distribution of molecular weights, except the R764-B7 antibody, which has a rate of multimers superior to the others (3.56% vs. 0-0.9%).

The analysis of the antibodies by CGE or PAGE technique, under reducing conditions, show that the R764-hHMFG1 has a rate of non-glycosylated heavy chain that is significatively superior (5.4%) to the 3 other antibodies (<1%). In addition, this antibody show a rate of $\alpha(1\text{-}6)$ linked fucose, which was determined by the lectin ELISA technique, that is very high (81%) in comparison to the 3 other antibodies, which have a rate of fucose that is about 30%.

The antigenic recognition done with the ELISA technique show that the R764-D11 and R764-B7 antibodies bind 10 times more strongly to the 32-mer MUC1 peptide than the 2 other antibodies, R764-G2 and R764-hHMFG1.

To conclude, we note that the anti-MUC1 antibodies coming from the maturation step of the scFv IIB6, though they have quite similar primary structures, behave differently with respect to their antigenic recognition (R764-G2 differs from the 2 others) and the stability of the IgG molecule (R764-B7 seems less "stable" than the 2 others). The R764-hHMFG1 control antibody whose primary structure differs from the antibodies coming from the scFv IIB6, shows an "atypical" glycosylation with respect to the other antibodies produced by the YB2/0 cell line.

EXAMPLE 3

ELISA with Anti-MUC1 IgG on MUC1 Peptide Antigen

Dilution series of anti-MUC1 IgG (D11, B7, G2)

3× Nunc Maxisorp plates coated with 50 ng/well MUC1 peptide antigen (32mer cys, sequence: ADPTRPAPG-STAPPAHGVSAPDTRPAPGSTAC)

Control plate was coated with 100 ng/well BSA

Blocking solution: 2% skim milk powder in PBS-T (0.1% Tween), 1 h, RT

IgG samples were diluted to a final concentration of 100 µg/ml with blocking solution samples were sequentially diluted 1:3.16 detection: goat anti-human IgG (Fc spec) HRP conjugate (Sigma, 1:39000), 1 h, RT Development: TMB substrate, reaction stopped with sulfuric acid after 10 minutes.

A450-A620 measured in a Tecan Sunrise Reader

Figure 10:
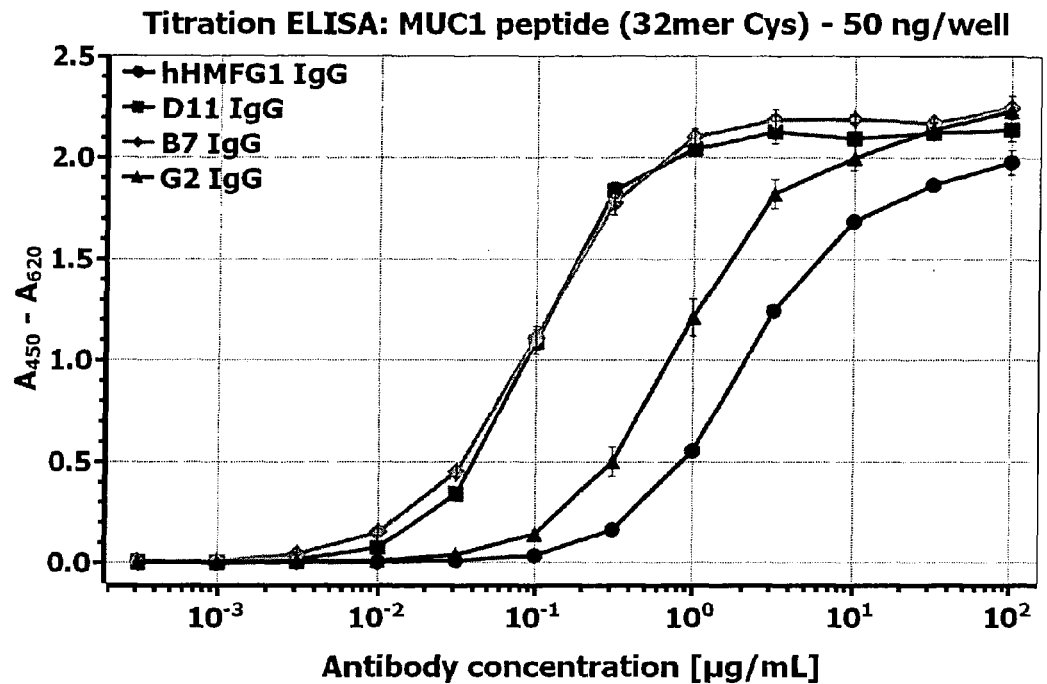
FIG. 10 represents the titration curve of antibodies B7, D11 and G2 against MUC-1 peptide by ELISA.
Figure 11:
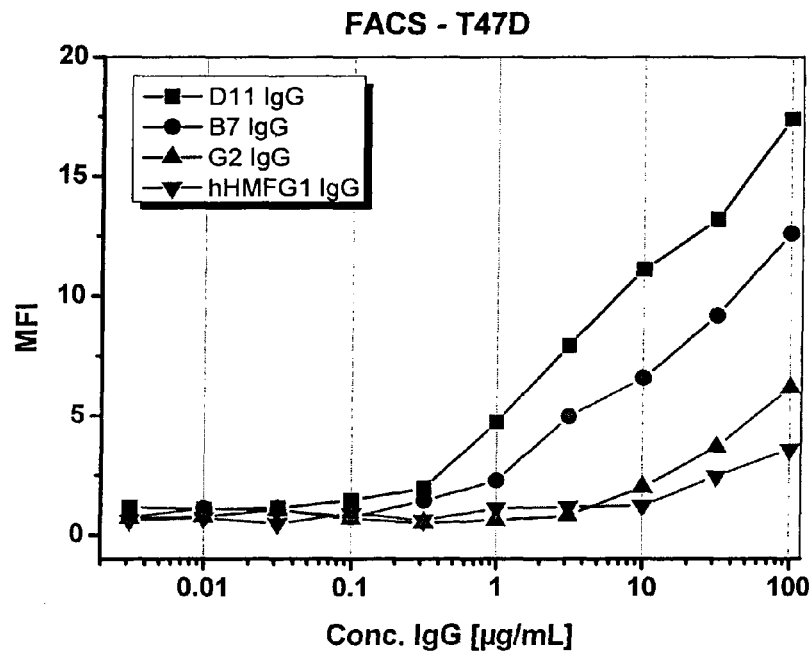
FIG. 11 represents the FACS comparison of the antibodies reactivity with T74D cells. MFI represents the mean fluorescence intensity.
Figure 12:
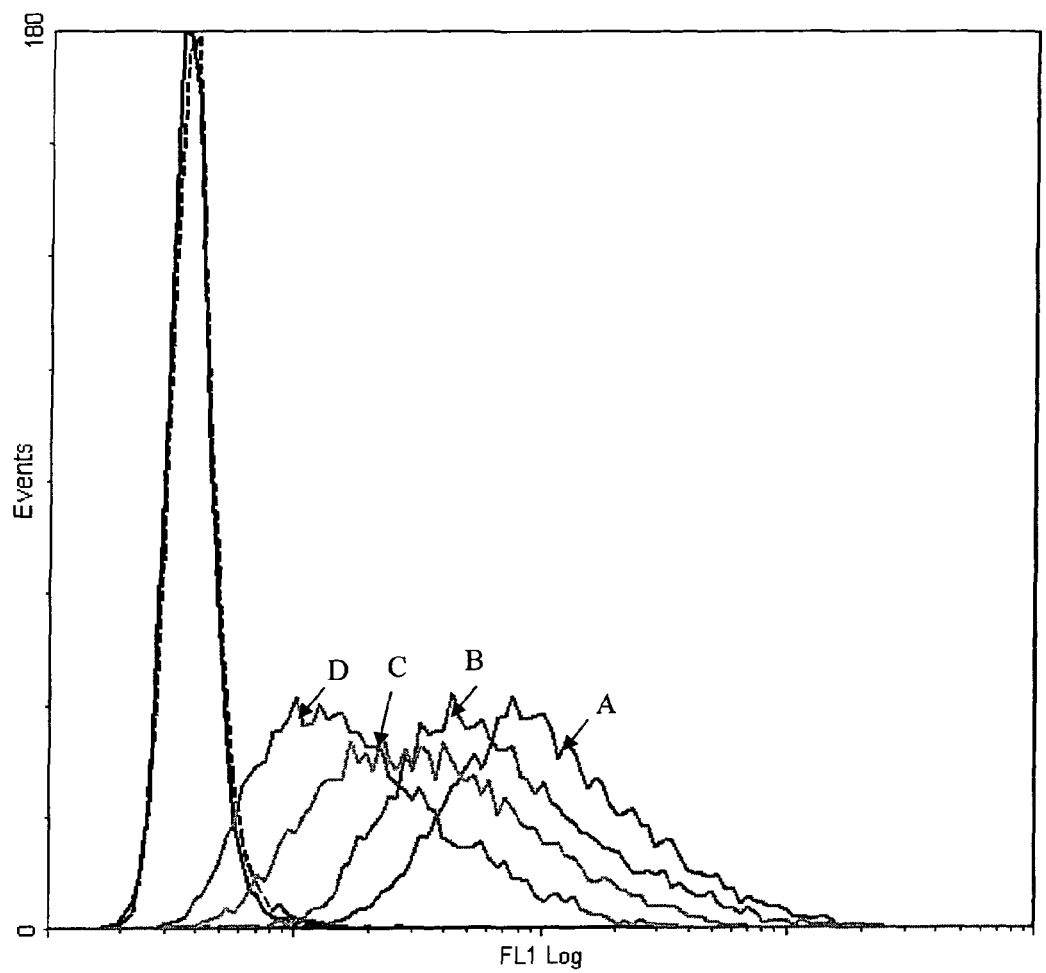
FIG. 12 represents the FACS overlay plots with 100 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 13:
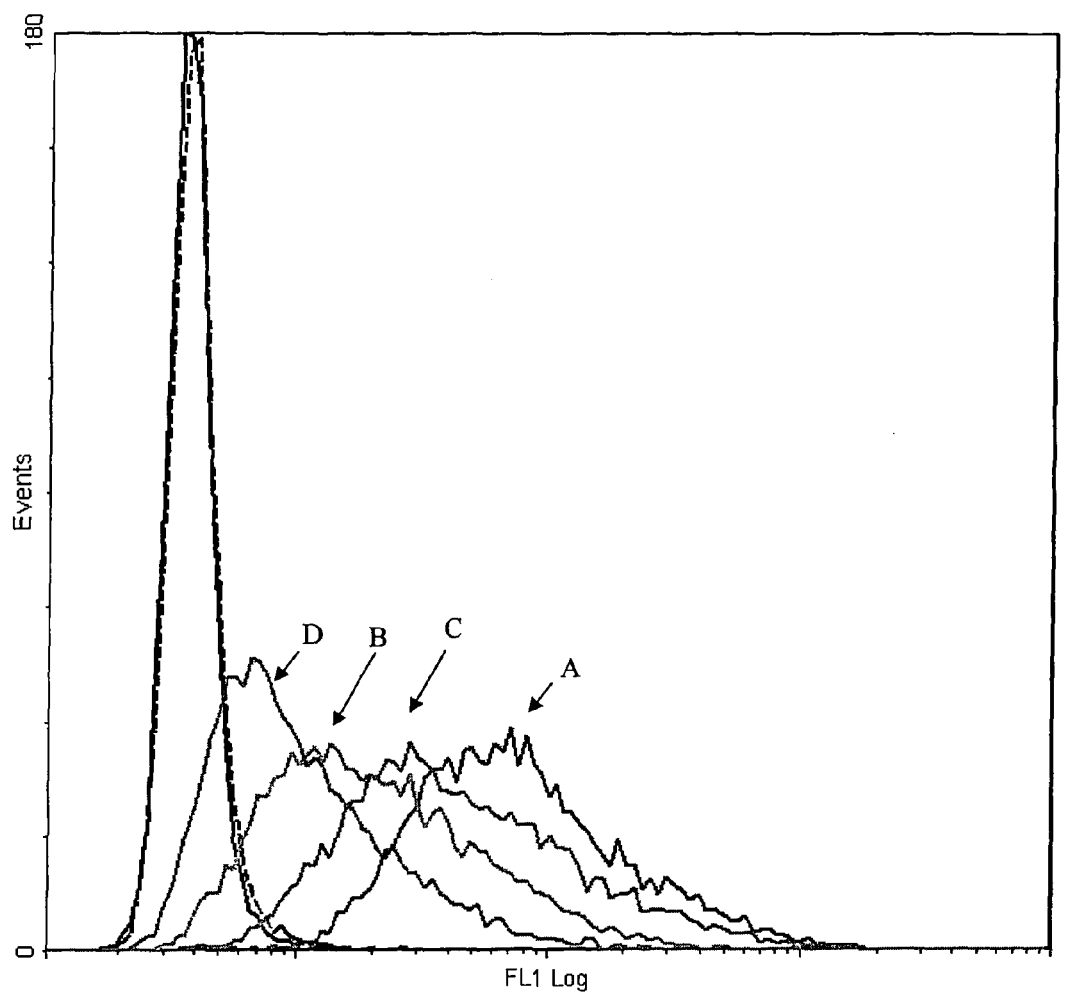
FIG. 13 represents the FACS overlay plots with 31.6 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 14:
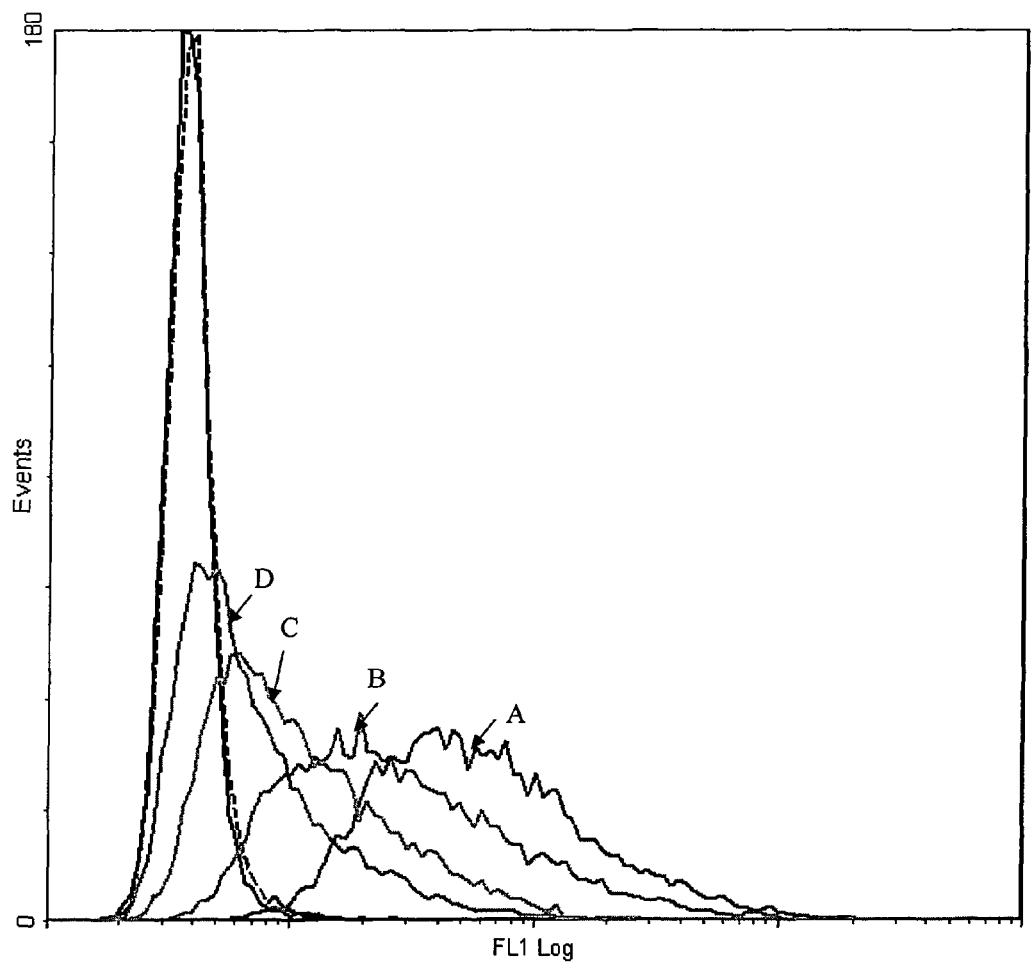
FIG. 14 represents the FACS overlay plots with 10 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 15:
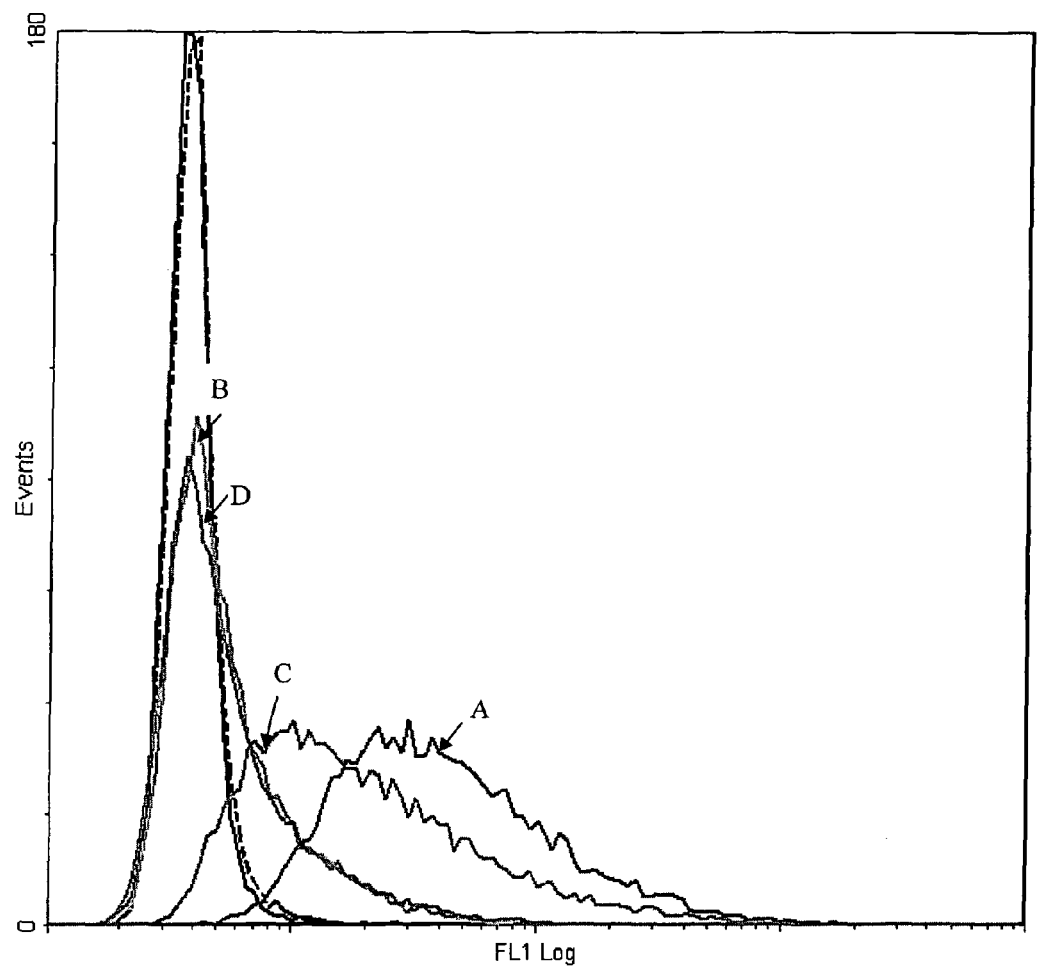
FIG. 15 represents the FACS overlay plots 3.16 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 16:
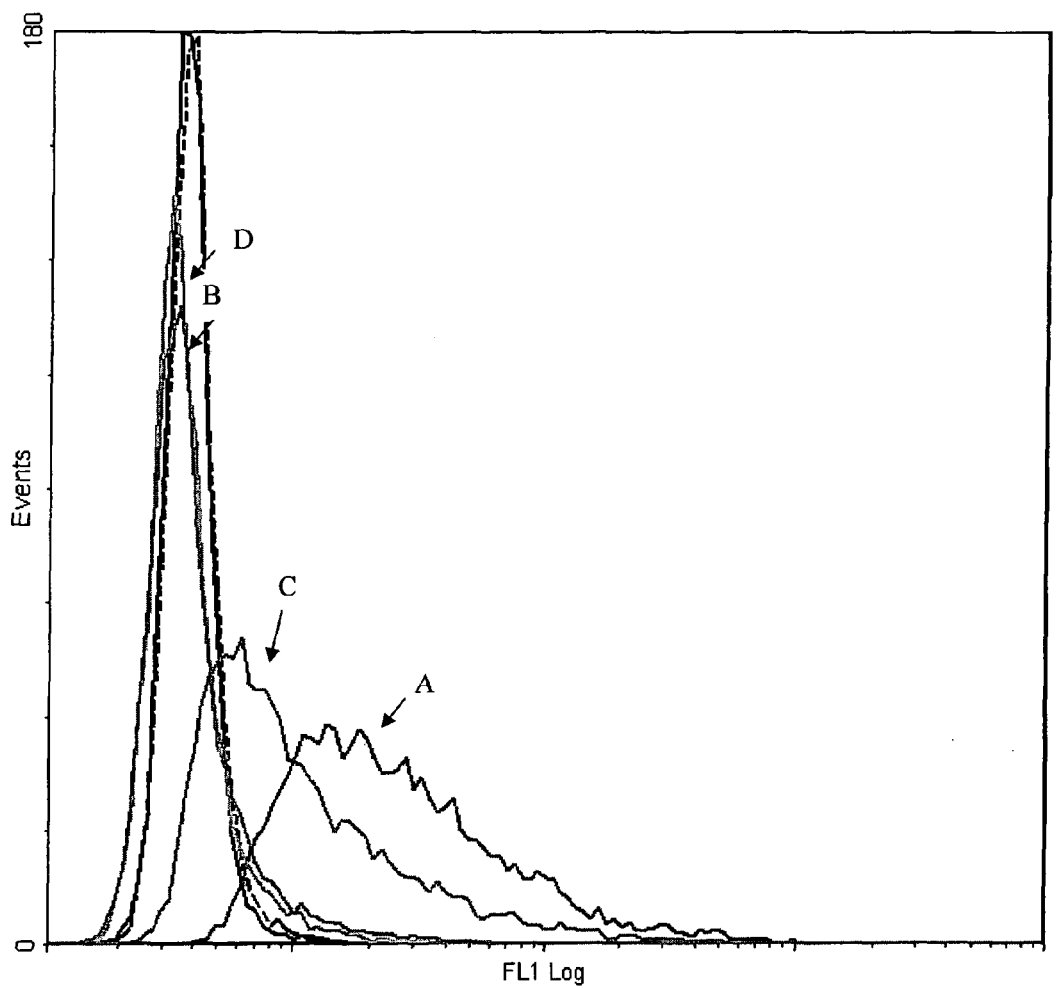
FIG. 16 represents the FACS overlay plots with 1 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 17:
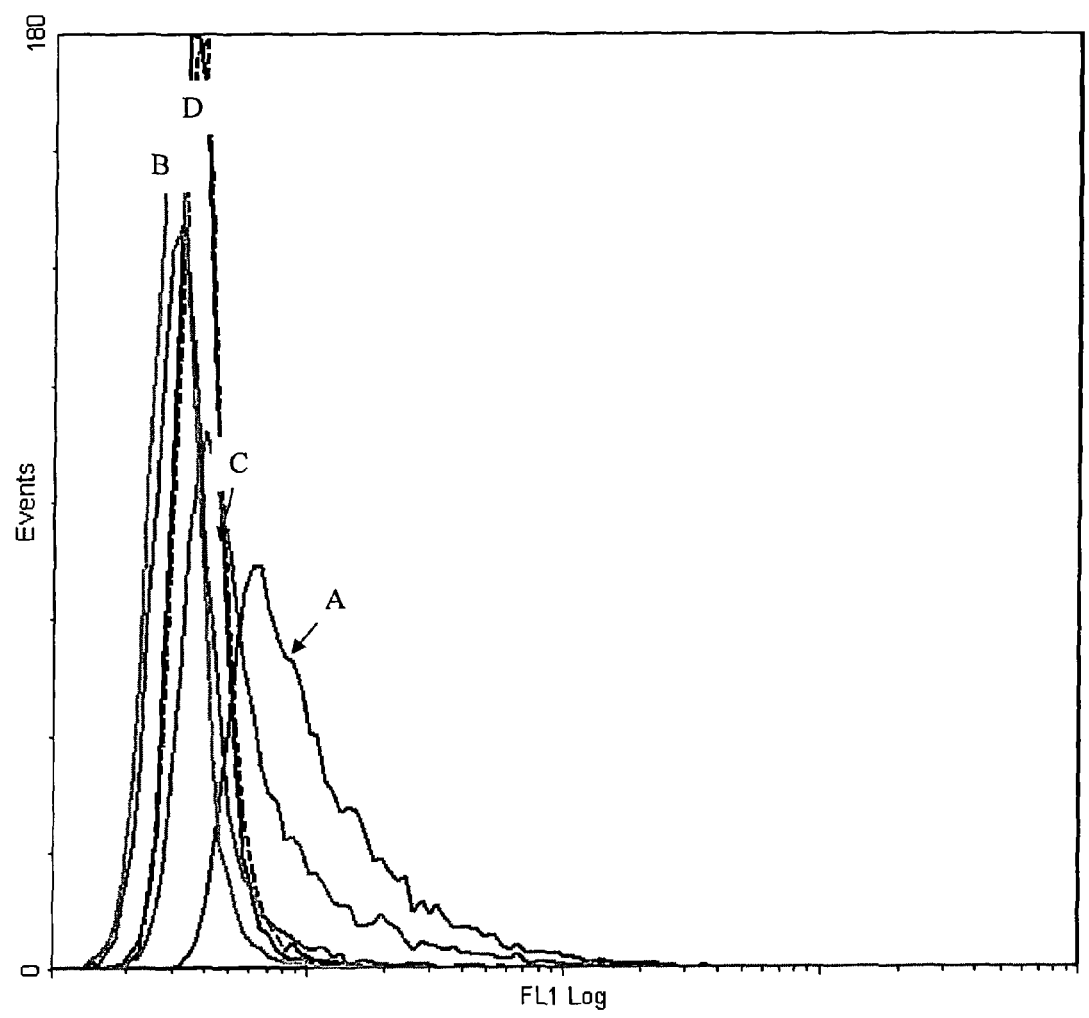
FIG. 17 represents the FACS overlay plots with 0.316 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 18:
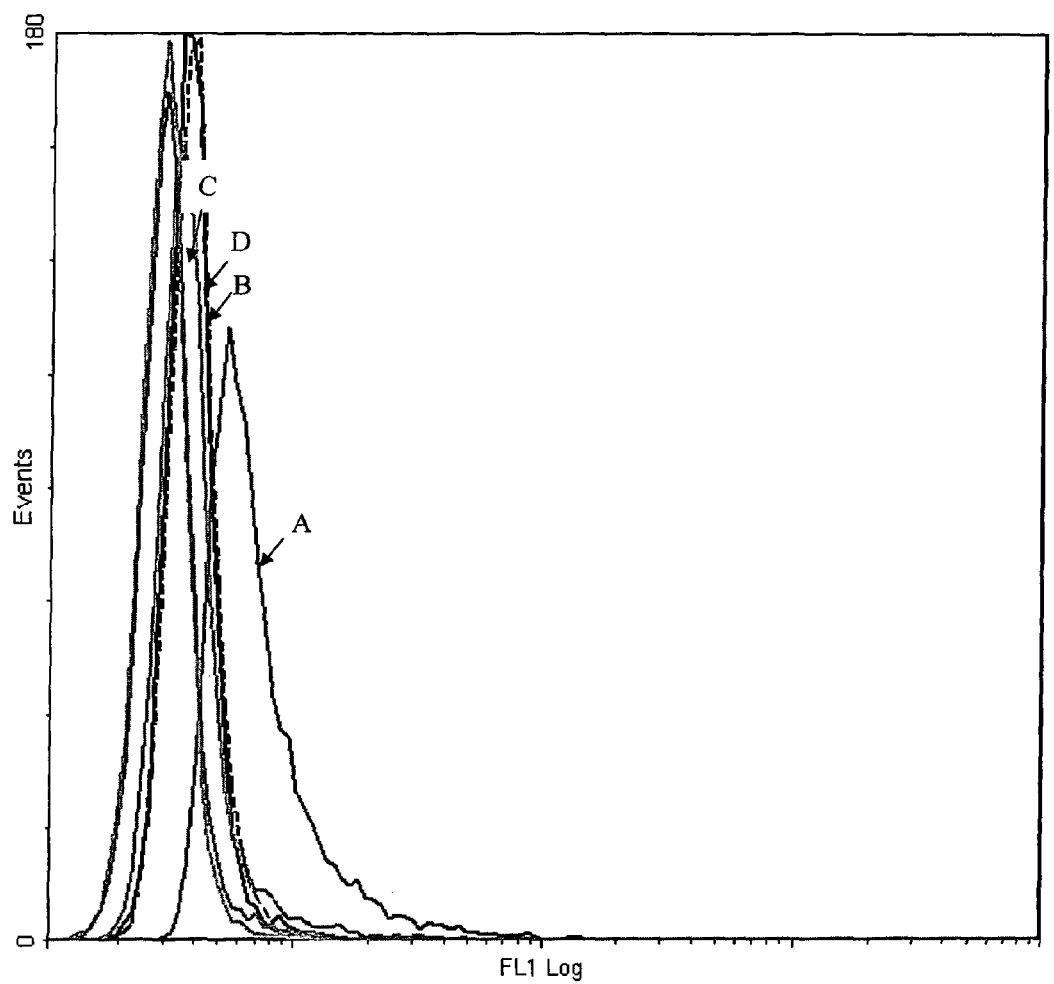
FIG. 18 represents the FACS overlay plots with 0.1 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 19:
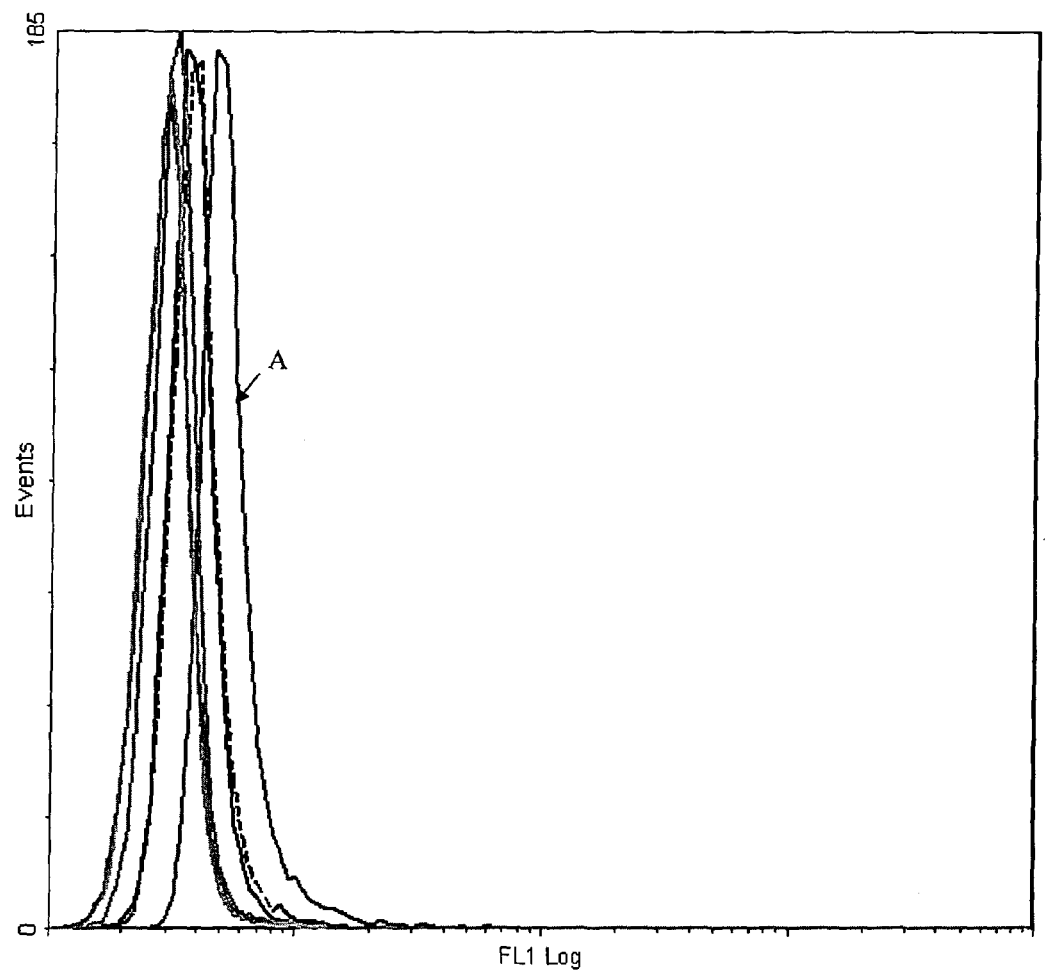
FIG. 19 represents the FACS overlay plots with 0.032 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 20:
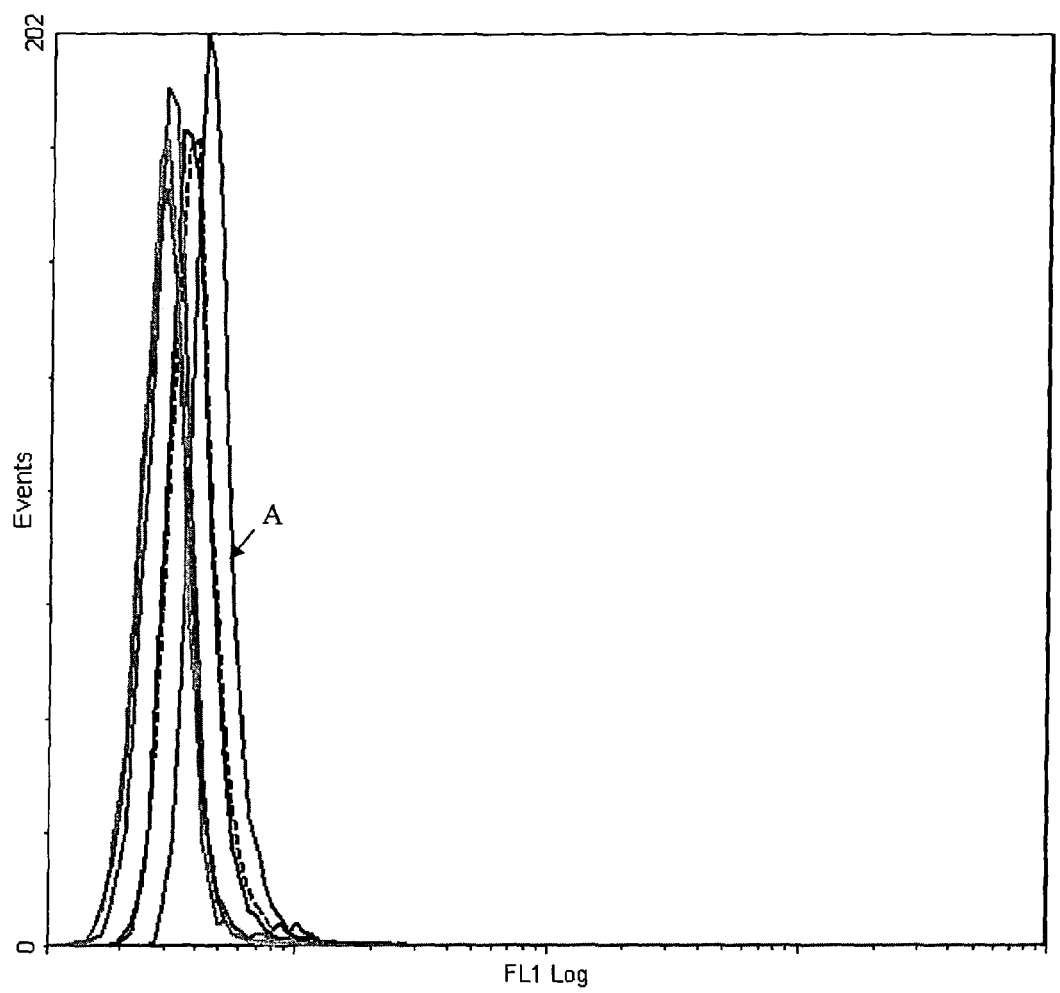
FIG. 20 represents the FACS overlay plots with 0.01 µg/ml of antibody. Black line: detection antibodies only, dashed black: IgG1 isotype control antibody, A line: D11 IgG, B line: B7 IgG, C line: G2 IgG and D line: hHMFG1 IgG.
Figure 21:
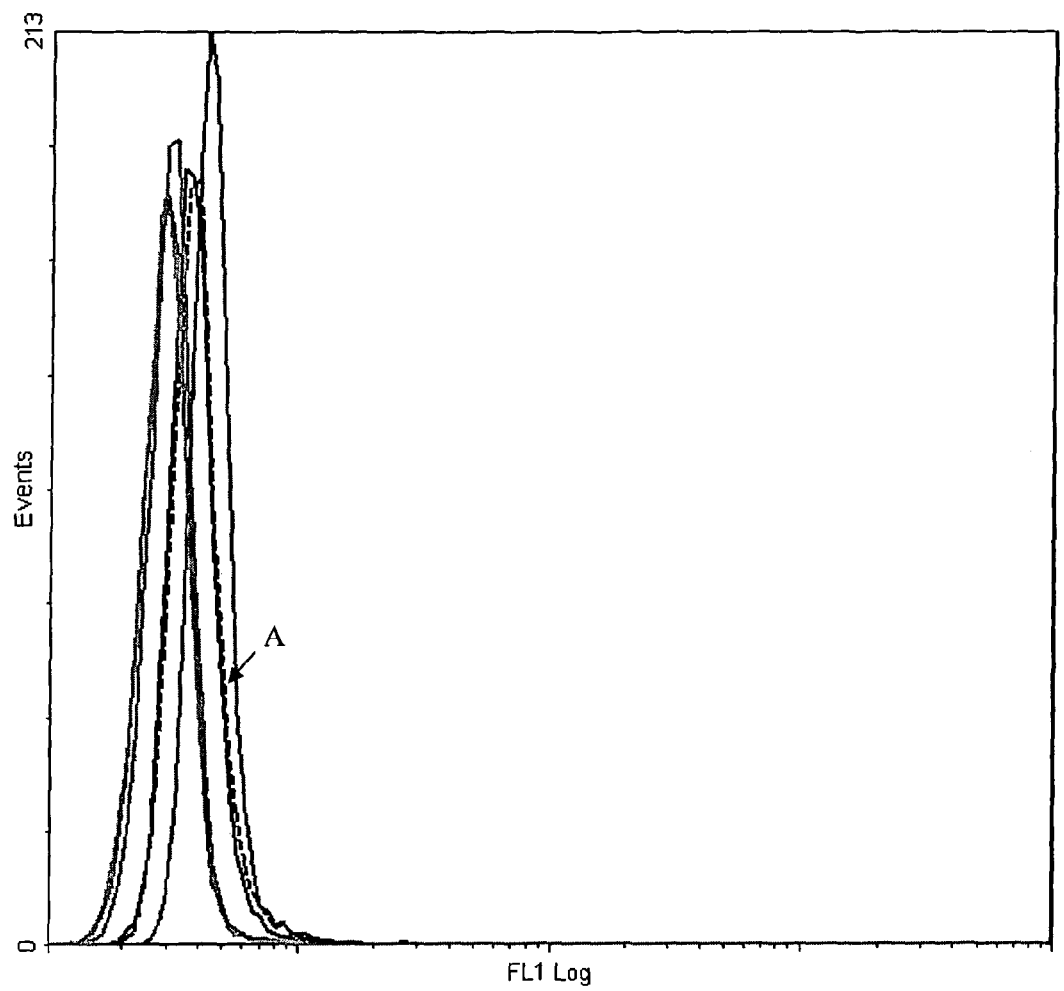
FIG. 21 represents the FACS overlay plots with 0.003 µg/ml of antibody. Black line: detection antibodies only, dashed black: IgG1 isotype control antibody, A line: D11 IgG, B line: B7 IgG, C line: G2 IgG and D line: hHMFG1 IgG.

Calculations performed:
    Mean value and standard deviation of three plates (MUC1) calculated
    BSA value (negative control) subtracted from mean value Plotting:
    Mean values were plotted against antibody concentration, SD is given by vertical error bars Results are presented in FIG. 10

EXAMPLE 4

FACS Analysis of Anti-MUC1 Antibodies on MUC1 Positive Cell Line T47D

Cell Lines
  T47D: ATCC No. HTB-133, MUC-1 Positives
Culture Conditions
  The cells were grown in 10 cm polystrol dishes at 37° C., 5% $CO_2$ in DMEM medium (4.5 g/L glucose) supplemented with 8% FCS and 1% Penicillin/Streptomycin stock solution (100×)
Cell Counting
  Cells were:
  washed with PBS (10 mL)
  solubilized by adding 1 mL trypsin/EDTA to each 10 cm dish
  Incubating for 5-10 min at RT
  resuspended by carefully pipetting up and down
  cells of all four plates were transferred to 5 mL medium
  dilution of cells with brome phenol blue solution
  10 µl of the brome phenol blue-cell mixture were analyzed in an Neubauer counting chamber, 4 big squares (factor $1 \times 10^4$ each) were counted

| Cell line | dilution | $1^{st}$ big square | $2^{nd}$ big square | $3^{rd}$ big square | $4^{th}$ big square | total | conc. cells/mL |
|---|---|---|---|---|---|---|---|
| T47D | 1:2 | 71 | 70 | 69 | 67 | 138 | $1.38 \times 10^6$ |

For each cell staining $1.4 \times 10^5$ cells should be used. Therefore the following volume of the cell suspension is needed:
  T47D: 101.5 µL, (each)
The following antibodies were used for specific MUC1 staining:

| | | amount for 146.2 µL with 100 µg/mL | |
|---|---|---|---|
| antibody | Conc. µg/mL | sample | buffer |
| human IgG1 (kappa) (Sigma, I5154) (iso) | 830 | 17.6 | 128.6 |
| hHMFG1 IgG | 2563 | 5.7 | 140.5 |
| D11 IgG | 2294 | 6.4 | 139.8 |
| B7 IgG | 755 | 19.4 | 126.8 |
| G2 IgG | 2152 | 6.8 | 139.4 |

From these antibody solutions further dilution by a factor of 3.162 were made (in a PP microtiter plate), so following antibody concentrations were used for FACS (µg/mL): 100, 31.62 10; 3.16; 1; 0.316; 0.1, 0.0316, 0.01, 0.003162
bound anti-MUC1 antibodies were detected by:
goat anti-human IgG (H+L) Alexa488 conj. 1:200=10 µg/mL final (Invitrogen resp.
Molecular probes Cat.No. A-11013) in 100 µL FACS buffer
in total: 38.5 µL (stock: 2 mg/mL) were given to 7661.5 µL FACS buffer
Cell Staining
  The above given volumes of cell suspension were given into 5 mL PP tubes (Greiner)
  add 3 mL FACS buffer (PBS+2% FCS+2 mM EDTA, ice cold) each
  centrifuge cells: 300× g, 4 min, 4° C.
  incubate 100 µL anti-MUC1 Abs (30 µg/mL), 1 h on ice
  centrifuge cells: 300×g, 4 min, 4° C.
  wash with 3 mL FACS buffer (ice cold)
  centrifuge cells: 300×g, 4 min, 4° C.
  wash with 3 mL FACS buffer (ice cold)
  incubate 100 µL detection antibody (goat anti-human IgG (H+L) Alexa488 conj.), 1 h on ice
  centrifuge cells: 300×g, 4 min, 4° C.
  wash with 3 mL FACS buffer (ice cold)
  centrifuge cells: 300×g, 4 min, 4° C.
  wash with 3 mL FACS buffer (ice cold)
  resuspend cells in 500 µL FACS buffer—store on ice until measurement
Measurement
  The measurement was performed on a Beckman Coulter Cytomics FC500. Gates were set by analyzing a mock-control of each cell line w/o any antibody incubation. Specific protocol files (.pro) were saved.
  10000 cells were analyzed per run.

| Concentration µg/ml | D11 IgG MFI | B7 IgG MFI | G2 IgG MFI | hHMFG1 IgG MFI |
|---|---|---|---|---|
| 100.0000 | 17.4 | 12.6 | 6.15 | 3.58 |
| 31.6228 | 13.2 | 9.16 | 3.68 | 2.45 |
| 10.0000 | 11.1 | 6.56 | 1.99 | 1.23 |
| 3.1623 | 7.92 | 4.96 | 0.802 | 1.16 |
| 1.0000 | 4.72 | 2.26 | 0.605 | 1.12 |
| 0.3162 | 1.96 | 1.44 | 0.515 | 0.606 |
| 0.1000 | 1.45 | 0.728 | 0.664 | 0.905 |
| 0.0316 | 1.13 | 1.04 | 1.04 | 0.474 |
| 0.0100 | 1.09 | 1.11 | 0.767 | 0.714 |
| 0.0032 | 1.17 | 0.738 | 0.706 | 0.602 |

Results are presented in FIG. 11 to FIG. 21.

EXAMPLE 5

ADCC Using NK Cells as Effector Cells

ADCC (Antibody-Dependent Cellular Cytotoxicity) with or without pre sensitisation consists to contact target cells, effector cells and antibodies (specific of the target cells)

Cytotoxic activity mediated by the used antibodies is revealed by colorimetry:lactate dehydrogenase (LDH) dosage which is released by lysed cells or by measuring the release of another constituent incorporated into target cell (AM calcein)
Protocol
1—Reagents
HBSS 1× for instance Invitrogen ref: 14170-088
Ficoll-Paque™ PLUS for instance GE Healthcare réf: 17-1440-03
DPBS for instance Invitrogen réf: 14190-094
NH4Cl 157 mM, EDTA 0.099 mM, KHCO3 9.99
EMS—5% SVF
NK Cell Isolation Kit—Miltenyi Biotec réef: 130-092-657
AutoMACS™ Running Buffer—Miltenyi Biotec ref: 130-091-221
AutoMACS™ Pro Washing Solution—Miltenyi Biotec réf: 130-092-987
IgG1-PE for instance Beckman Coulter ref: A07796
CD3-PE for instance Beckman Coulter ref: A07747
CD14-PE for instance Beckman Coulter ref: A07764
CD16-PE for instance Beckman Coulter ref: A07766
CD19-PE for instance Beckman Coulter ref: A07769
CD56-PE for instance Beckman Coulter re: A07788

AM calcein 1 mg/ml in DMSO for instance Invitrogen ref: C3099
EMS—5% SVF—4 mM sulfinpyrazone
EMS—5% SVF—2% Triton X100
Cytotoxicity Detection Kit for instance ROCHE ref: 11 644 793 001
HCl 1N
DPBS—1% PFA
2—Procedure
  Effector Cells
  Blood Sample Extraction
  Blood is diluted twice with HBSS 1×.
  Diluted blood is aliquoted in 50 mL tubes containing:
  15 ml of Ficoll-Paque™ PLUS at room temperature
  30 ml of diluted blood,
  Centrifugation 530 g, 20 minutes RT
  Extraction of Monuclear Cells
with a pipette, mononuclear cells are gently collected and transferred to a 50 mL tube containing HBSS 1×
  MNC are washed by centrifugation at 480 g for 10 minutes at RT
  Discard supernatant and pellets are pooled in HBSS 1×.
  Platelet Elimination
  Cells are centrifuged at 190 g, 15 minutes RT
  Red Cells Elimination
  Supernatant is discarded and pellets are resuspended in 50 ml of $NH_4Cl$, and left at RT for 5 min under agitation.
  Cells are centrifuged at 480 g 5 min RT.
  Cells are washed once with HBSS 1× by centrifugation à 480 g 5 minutes RT
  Discard supernatant.
  Counting
  Cells are counted in a Malassez cell.
  NK purification by Negative Selection for $100 \times 10^6$ MNC
  0.4 ml of cold AutoMACS Running Buffer is added and 0.1 ml of the NK Cell Biotin-Antibody Cocktail is added
Leave at 4° C. for 10 min
0.3 ml cold AutoMACS Running Buffer+0.2 ml of NK Cell MicroBead Cocktail are added
Leave at 4° C. for 15 min
Add 1 to 2 ml of cold AutoMACS Running Buffer.
Centrifugation 300 g 10 minutes, +4° C.
Discard supernatant.
Pellet is resuspended with 500 µl of cold AutoMACS Running Buffer for $100 \times 10^6$ cells.
Filtration on 30 µm filter previously incubated with AutoMACS Running Buffer.
Place on AutoMACS Pro and run the ad hoc program:
collect elution containing NK cells
Place cells, after one wash step, on EMS+5% SVF
  Facs NK Phenotyping
  Cell labelling (1 well by dye)
  put 50 µl of NK cell suspension+5 µl of antibody coupled with PE (IgG1; CD3; CD14; CD16; CD19; CD56) in a 96-well plate.
Leave on ice for 10 min
cells are washed twice by centrifugation 330 g 10 min
cells are fixed in 300 µl DPBS containing 1% PFA.
  Preparation of Target Cells
Wash by addition of DPBS and centrifuge at 480 g, at room temperature during 5 minutes
Eliminate the supernatant and put the centrifugation pellet into EMS+5% FBS medium in order to obtain:
  in case of a lactate dehydrogenase (LDH) revelation test: $6 \times 10^5$ cells/mL
  in case of a Calcein-AM revelation test: $3 \times 10^6$ cells/mL To 1 mL of cell suspension containing between 1 and $3 \times 10^6$ cells/mL in EMS+5% FBS medium, add 25 µL of Calcein-AM at 1 mg/mL in DMSO solution.
Incubate at 37° C.—7% $CO_2$ during 20 minutes
Fill the tube with the EMS+5% FBS medium
Centrifuge at 480 g and at room temperature during 5 minutes
Gently resuspend the centrifugation pellet in EMS+5% FBS medium and fill the tube with this medium
Centrifuge at 480 g and at room temperature during 5 minutes
  Discard the supernatant and gently resuspend the centrifugation pellet in order to obtain a solution which has a concentration of $3 \times 10^5$ cells/mL in EMS+5% FBS medium-4 mM sulphinpyrazone, preheated to 37° C.
  Preparation of the Antibodies
  Dilute the antibodies that are in the EMS+5% FBS medium to a concentration of 20 µg/mL. Then dilute from one in ten to one in ten with a new pipette tip for each dilution
  ADCC Test
  1. Put 50 µL/well for each antibody to be tested
  2. Add 50 µL/well of the target cell suspension
  3. Add 50 µL/well of the effector cell suspension
  4. Add EMS+5% FBS medium to obtain a final volume of 200 µL
  One obtain for each well a cell ratio R, with:
  R=effector cells/target cells=X/Y
  The ideal ratio is R=15/1. According to the number of antibodies to be tested and to the number of recovered NK cells, each condition is tested in duplicate or triplicate.
  Control Wells (Duplicate or Triplicate of Wells)
  Standard Reference Range: 100%, 50%, 25% and 0% of Lysis (Duplicate or Triplicate)
  1. 100%: 50 µL of target cells+50 µL of EMS containing 5% of FBS+100 µL of Triton X100 at 2%
  2. 50%: 25 µL of target cells+75 µL of EMS containing 5% of FBS+100 µL of Triton X100 at 2%
  3. 25%: 12.5 µL of target cells+87.5 µL of EMS containing 5% of FBS+100 µL of Triton X100 at 2%
  4. 0%: 100 µL of EMS containing 5% of FBS+100 µL of Triton X100 at 2%
  The Control Cell Targets
  50 µL of target cells+150 µL of EMS containing 5% of FBS
  The Control Effector Cells
  50 µL of effectors cells+150 µL of EMS containing 5% of FBS
  The Control AICC
  50 µL of target cells+50 µL of effectors cells+100 µL EMS containing 5% of FBS
  The Control Antibodies
  50 µL of antibodies at the different target cell concentrations+50 µL of target cells+100 µL of EMS containing 5% of FBS
  After the distribution of all constituents:
  Gently agitate
Centrifuge at 125 g and at room temperature during 1 minute
Incubate the plates at 37° C. and 7% CO2 during 4 hours for a Calcein-AM revelation or during one night for a LDH revelation test.
  A—Colorimetric Method for the LDH Titration
  After incubation at 37° C. and 7% CO2 during one night:
Centrifuge the plates at 125 g at room temperature during 1 minute Gently sample 130 μL of supernatant of every well and transfer them to a 96-well round-bottomed plate with a multichannel pipette Centrifuge these plates again at 125 g and at room temperature during 1 minute Gently sample 50 μL of supernatant of every well and transfer them to a 96-well flat-bottomed plate with a multichannel pipette In these 50 μL of supernatants, gently add (to avoid the formation of air bubbles) 50 μL of the revealing solution of the cytotoxicity detection kit (dilute the first reagent to 1:45 in the second reagent of the kit).

Incubate at room temperature in the dark for 30 minutes

Add 100 μL/well of HCl 1N in order to stop the enzymatic reaction

If necessary, eliminate the air bubbles with a single use needle

Gently agitate, and read the O.D. at 492 nm with help of the BIOLISE software

B—Calcein-AM Method Using a Fluorimeter

After incubation at 37° C. and 7% CO2 during 4 hours:

Centrifuge the plates at 125 g at room temperature during 1 minute

Gently sample 150 μL of supernatant of every well and transfer them to a 96-well round-bottomed plate with a multichannel pipette Centrifuge these plates again at 125 g and at room temperature during 1 minute Sample 100 μL of supernatants and gently transfer them in a black 96-well flat-bottomed plate At this stage, the plates can be stored in a refrigerator for a maximum of 24 hours.

Figure 22:
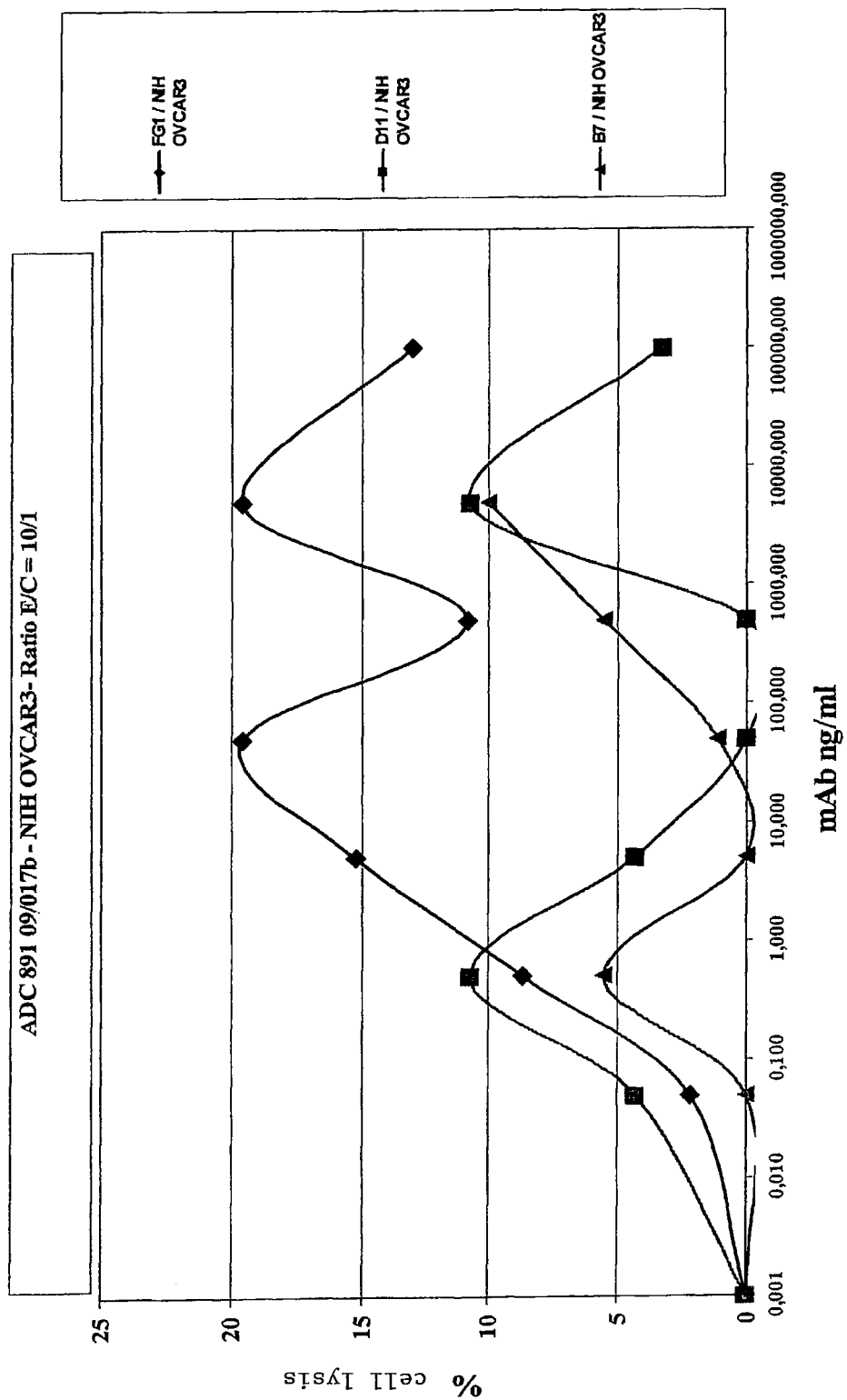
FIG. 22 represents the ADDC. The graph represents the percentage of cell lysis with respect to the concentration of antibodies.

Put the plate in the fluorimeter: excitation at 485 nm and emission at 535 nm. Read with help of the BIOLISE software The results are shown in the FIG. 22.

Annex 1—Preparation of Solutions

A EMS—5% FBS
  95 mL EMS for instance Invitrogen Ref: 041-95181M
  5 mL FBS for instance Invitrogen Ref: 011-90018M 5%
  Can be stored in the refrigerator for 1 month B EMS—5% FBS—Triton X100 2%
  5 μL EMS—5% FBS (Solution A)
  100 μL Triton X100 for instance Sigma Ref: 9002-93-1 2%
  Can be stored in the refrigerator for 1 month C NH4Cl 157 mM, EDTA 0.099 mM, KHCO3 9.99 mM
  See the M.O. No. 623/04635
  Can be stored in the refrigerator for 3 years D HCl 1 N
  1,000 mL of demineralised water
  91 mL of concentrated HCl 37%, for instance Merck Ref: 1.00314.1000 1 N
  Can be stored at room temperature for 1 year E NaOH 1 N
  90 mL of demineralised water
  10 mL of NaOH 30%, for instance Prolabo Ref: 28226293 1 N
  Can be stored at room temperature for 1 year F Sulphinpyrazone 0.1 M
  0.2420 g of sulphinpyrazone for instance Sigma Ref: S9509 0.1 M
  Q.S. 6 ml NaOH 1 N (Solution E) 1 N
  Can be stored in the refrigerator for 2 months G EMS—5% SVF—4 mM Sulphinpyrazone
  48 ml EMS—5% FBS (Solution A)
  2 ml sulphinpyrazone 0.1 M (Solution F) 4 mM
  150 μl of concentrated HCl 37%, for instance Merck Ref: 1.00314.1000 pH 7.5
  Filter on a 0.2 μm.
  Can be stored in the refrigerator for 1 month Remark: The sulphinpyrazone is a blocker of the calcium channels. It is used to avoid the spontaneous release of the Calcein-AM H DPBS—4% PFA
  4 g of paraformaldehyde for instance Sigma P6148 4%
  Q.S. 100 ml DPBS for instance Invitrogen Ref: 14190-094
  Make aliquots of 1 mL
  Can be stored in the freezer for 1 month I DPBS—1% PFA
  1 ml of DPBS—4% PFA (Solution H) 1%
  3 ml of DPBS for instance Invitrogen Ref: 14190-094
  Can be stored in the refrigerator for 1 month

EXAMPLE 5

Determination of In Vitro Serum Stabilites of Anti-MUC1 IgG or Anti-MUC1 scFv-Fc Fusion Proteins Used Antibodies
  632 09 143 R764 huHMFG1 785 μl 2563 μg/ml
  632 09 144(2) R764 HT186-D11 875 μl 2294 μg/ml
  D11 scFv-Fc (HT351) 0.62 mg/ml Preparation
  5 ml antibody solution (in PBS) were prepared each, conc. 20 μg/ml
  hHMFG1: 39 μl+4961 μl
  D11 IgG: 43.6 μl+4956.4 μl
  D11 scFv-Fc: 161.3 μl+4839 μl Each dilution was prepared 3× to have material for triplicates.

100 μl of these solutions were mixed with either 100 μl PBS (incl. 1% Pen/Strep, PAA laboratories) or human serum (off the clot, PAA laboratories Cat. No. C11-020, Lot. 002007-0863 suppl. with 1% Pen/Strep and 0.1% Sodium azide) and human serum inactivated for 30 min at 56° C.

The mixtures were put into tubes and freezed at −80° C.

On specific time point aliquots were incubated at 37° C. 20.5.|27.5.|30.5.|3.6.|5.6.|9.6.|12.6.|16.6.|17.6.

Figure 23:
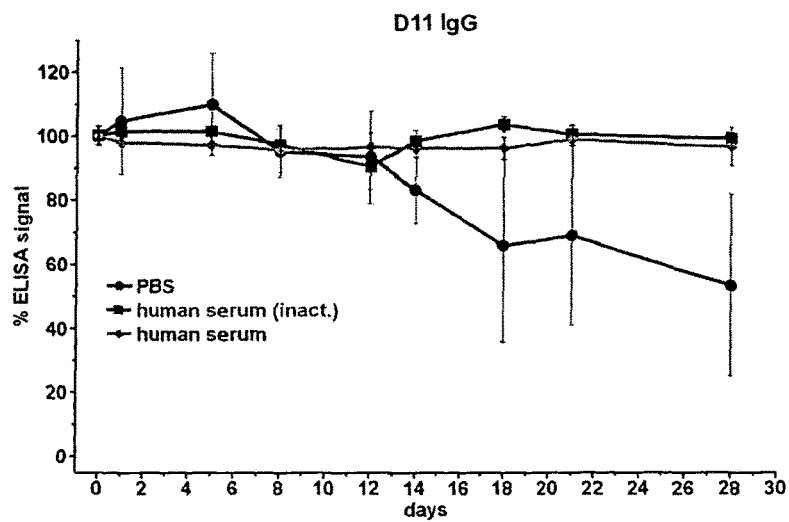
FIG. 23 represents the D11 IgG antibody stability in PBS, human inactivated serum or human serum. The stability is measured by ELISA during 28 days.
Figure 24:
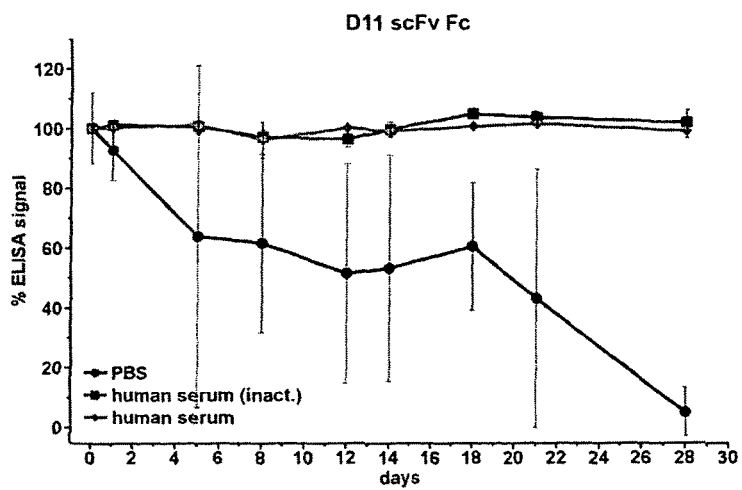
FIG. 24 represents the D11 scFv Fc fragment stability in PBS, human inactivated serum or human serum. The stability is measured by ELISA during 28 days.
Figure 25:
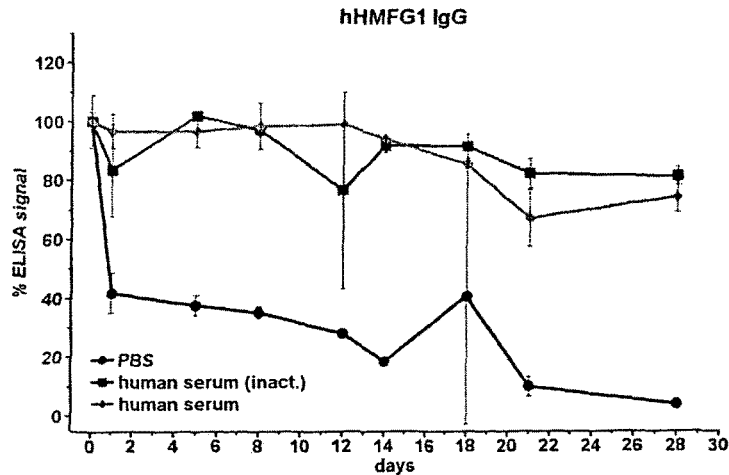
FIG. 25 represents the D11 hHMFG1 IgG antibody stability in PBS, human inactivated serum or human serum. The stability is measured by ELISA during 28 days.

Elisa
  MUC1 peptide (32 mer cys) was coated with 50 ng per well in microtiter plates. Wells were blocked with 2% skim-milk powder in PBS-T (0.1% Tween20). (BSA 100 ng/well as negative control).
  50 μl of each aliquot were mixed with 50 μl blocking solution and incubated for 1 h at RT.
  A goat anti-human IgG (Fc spec. HRP conj.) was used as detection antibody.
  TMB development was done for 9 min.
  Results for D11 IgG, D11 scFv FC and D11 hHMFG1 IgG are presented respectively in FIGS. 23, 24 and 25

EXAMPLE 6

Antibody Internalisation

Cells: MCF-7 cell lines expressing MUC-1
Antibody is added to target cell
Antibodies and cells are incubated at 37° C. for 1 hour, or 4° C. for the control
Cells are washed for removing free antibodies.
Secondary antibody is added for 1 hour at 4° C.

Cells are washed for removing free antibodies.
Fluorescence is measured by using FACS.
Results are shown in FIG. 26.

The results show that about 70% of the antibodies (D11 or control antibody FG1) are internalized after 1 hour of incubation at 37° C. on MCF7 cells.

The invention claimed is:

1. A binding peptide having an affinity for the epitope formed by amino acid sequence RPAP (SEQ ID NO: 137) of a peptide, the binding peptide comprising a heavy chain variable region amino acid sequence
   FR1-CDR1-FR2-CDR2-FR3-CDR3-FR4
wherein CDR1 is SEQ ID NO: 1;
   CDR2 is SEQ ID NO: 7; and
   CDR3 is SEQ ID NO: 13;
said binding peptide further comprising, in association with the heavy chain amino acid sequence, a light chain variable amino acid sequence
   FR1-CDR1-FR2-CDR2-FR3-CDR3-FR4
wherein CDR1 is SEQ ID NO: 19;
   CDR2 is SEQ ID NO: 25; and
   CDR3 is SEQ ID NO: 31.

2. The binding peptide of claim 1, wherein the heavy chain FR1 is SEQ ID NO: 37;
   FR2 is SEQ ID NO: 43;
   FR3 is SEQ ID NO: 49;
   FR4 is SEQ ID NO: 55;
   and wherein the light chain FR1 is SEQ ID NO: 61;
   FR2 is SEQ ID NO: 67;
   FR3 is SEQ ID NO: 73;
   FR4 is SEQ ID NO: 79.

3. The binding peptide of claim 1, wherein the heavy chain variable amino acid sequence is SEQ ID NO: 85; and the light chain variable amino acid sequence is SEQ ID NO: 91.

4. The binding peptide of claim 1, wherein each variable amino acid sequence is directly linked to at least one C-terminal constant region.

5. The binding peptide of claim 4, wherein the heavy chain variable amino acid sequence is directly linked to a C-terminal constant region with SEQ ID NO: 97 and wherein the light chain variable amino acid sequence is directly linked to a C-terminal constant with SEQ ID NO: 109.

6. The binding peptide of claim 1, wherein the binding peptide is as single chain peptide with SEQ ID NO: 123.

7. The binding peptide of claim 1, wherein the light chain variable amino acid sequence is comprised on a first peptide and the heavy chain variable amino acid sequence is comprised on a second peptide, preferably said first peptide is SEQ ID NO: 128, and said second peptide is SEQ ID NO: 136.

8. The binding peptide of claim 1, wherein at least one of the heavy chain amino acid sequence and the light chain amino acid sequence is linked to an effector that is detectable label selected from the group consisting of a dye, a radionucleotide, a toxin, and a cytotoxic enzyme.

9. A pharmaceutical composition for use in medical treatment of adenocarcinoma, comprising a binding peptide according to claim 1.

10. Process for analysis comprising the steps of contacting a sample suspected of containing a component comprising MUC1 epitope with a binding peptide according to claim 1 and detecting binding peptide bound to a component of the sample.

11. The process of claim 10, wherein the sample is a biopsy of human origin.

12. A process for production of a peptide specifically binding to MUC1, comprising expressing the binding peptide from a nucleic acid sequence encoding the binding peptide in an expression cassette producing the peptide, wherein the peptide is a binding peptide according to claim 1.

13. A process for production of a binding peptide of claim 1, comprising expressing the binding peptide in a cultivated cell containing a nucleic acid sequence encoding the binding peptide in an expression cassette.

14. The process of claim 13, wherein the cultivated cell is selected from the group consisting of a mammalian cell, a fungal cell, a yeast cell and a bacterial cell.

15. The process of claim 13, wherein the sequence encoding the binding peptide contains a sequence encoding a signal peptide for export of the binding peptide out of the cultivated cell's cytoplasm.

* * * * *